US010513559B2

(12) United States Patent
Faulstich et al.

(10) Patent No.: US 10,513,559 B2
(45) Date of Patent: Dec. 24, 2019

(54) AMATOXIN-ARMED THERAPEUTIC CELL SURFACE BINDING COMPONENTS DESIGNED FOR TUMOUR THERAPY

(71) Applicant: Deutsches Krebsforschungszentrum, Heidelberg (DE)

(72) Inventors: Heinz Faulstich, Heidelberg (DE); Gerhard Moldenhauer, Heidelberg (DE)

(73) Assignees: DEUTSCHES KREBSFORSCHUNGSZENTRUM, Heidelberg (DE); Heinz Faulstich, Heidelberg (DE)

(*) Notice: Subject to any disclaimer, the term of this patent is extended or adjusted under 35 U.S.C. 154(b) by 0 days.

(21) Appl. No.: 14/954,266

(22) Filed: Nov. 30, 2015

(65) Prior Publication Data

US 2016/0089450 A1 Mar. 31, 2016

Related U.S. Application Data

(63) Continuation of application No. 13/263,287, filed as application No. PCT/EP2010/002205 on Apr. 8, 2010, now Pat. No. 9,233,173.

(60) Provisional application No. 61/167,690, filed on Apr. 8, 2009, provisional application No. 61/222,227, filed on Jul. 1, 2009.

(51) Int. Cl.

| | |
|---|---|
| ***C07K 16/32*** | (2006.01) |
| ***C07K 16/30*** | (2006.01) |
| ***A61K 47/68*** | (2017.01) |

(52) U.S. Cl.

CPC .......... *C07K 16/32* (2013.01); *A61K 47/6831* (2017.08); *A61K 47/6849* (2017.08); *A61K 47/6851* (2017.08); *A61K 47/6855* (2017.08); *C07K 16/30* (2013.01); *C07K 2317/24* (2013.01); *C07K 2317/56* (2013.01); *C07K 2317/73* (2013.01); *C07K 2317/92* (2013.01)

(58) Field of Classification Search

CPC .................................................. A61K 47/6831

See application file for complete search history.

(56) References Cited

U.S. PATENT DOCUMENTS

| | | | | |
|---|---|---|---|---|
| 6,890,765 | B2 | 5/2005 | Lawrence et al. | |
| 9,399,681 | B2 * | 7/2016 | Anderl | A61K 47/48415 |
| 2003/0012734 | A1 | 1/2003 | Pathak et al. | |
| 2003/0105000 | A1 | 6/2003 | Pero et al. | |
| 2005/0059082 | A1 | 3/2005 | Breitling et al. | |
| 2013/0259880 | A1 | 10/2013 | Anderl et al. | |

FOREIGN PATENT DOCUMENTS

| | | | |
|---|---|---|---|
| EP | 1 661 584 | A1 | 11/2004 |
| EP | 1 859 811 | A1 | 11/2007 |
| WO | 2007121326 | A2 | 10/2007 |

OTHER PUBLICATIONS

"Carbodiimide Crosslinker Chemistry," Thermo Scientific: Pierce Protein Biology Products, 2013, pp. 1-3.

alpha-amanitin (PubChem Compound, CID 9543442, NIH, US Nat. Library Med. NCBI, Aug. 16, 2006).

Bera, Tapan K. et al., "Pharmacokinetics and Antitumor Activity of a Bivalent Disulfide-stabilized Fv Immunotoxin with Improved Antigen Binding to erbB2," *Cancer Res*, 1999, 59:4018-4022.

Bermbach, Ute et al., "Epidermal Growth Factor Labeled β-Amanitin-Poly-L-ornithine: Preparation and Evidence for Specific Cytotoxicity," *Biochemistry*, 1990, 29:6839-6845.

beta-amanitine (PubChem Compound, CID 2276, NIH, US Nat. Library Med. NCBI, Mar. 25, 2005).

Colman, P.M. "Effects of amino acid sequence changes on antibody-antigen interactions," $55^{th}$ Forum in Immunology, 1994, 145(1):33-36.

epsilon-amanitine (PubChem Compound, CID 30508, NIH, US Nat. Library Med. NCBI, Aug. 8, 2005).

Faulstich, H. et al., "Amanita Toxins Bound to Biopolymers," *Peptides, Proceedings of the European Peptide Symposium*, Jan. 1975, pp. 333-338, Heidelberg, Germany.

Faulstich, H. et al., "Ether Derivatives of α-Amanitin. Introduction of Spacer Moieties, Lipophilic Residues, and Radioactive Labels," *Biochemistry*, 1981, 20(22):6498-6504.

Faulstich, Heinz et al., "Protein Conjugates of Fungal Toxins," *Methods in Enzymology*, 1985, 112:225-237, Academic Press, Inc., San Diego, California, US.

Güssow, Detlef et al., "Humanization of Monoclonal Antibodies," *Methods in Enzymology*, 1991, 203:99-121.

Ibragimova, Gulshat T. et al., "Stability of the β-Sheet of the WW Domain: A Molecular Dynamics Simulation Study," *Biophysical Journal*, Oct. 1999, 77:2191-2198.

Rudikoff, Stuart et al., "Single amino acid substitution altering antigen-binding specificity," *Proc Natl Acad Sci USA, Immunology*, Mar. 1982, 79:1979-1983.

(Continued)

*Primary Examiner* — Peter J Reddig

(74) *Attorney, Agent, or Firm* — Saliwanchik, Lloyd & Eisenschenk

(57) ABSTRACT

The invention relates to tumour therapy. In one aspect, the present invention relates to conjugates of a toxin and a target-binding moiety, e.g. an antibody, which are useful in the treatment of cancer. In particular, the toxin is an amatoxin, and the target-binding moiety is preferably directed against tumour-associated antigens. In particular, the amatoxin is conjugated to the antibody by linker moieties. In particular the linker moieties are covalently bound to functional groups located in positions of the amatoxin proved as preferred positions for the attachment of linkers with respect to optimum antitumor activity. In a further aspect the invention relates to pharmaceutical compositions comprising such target-binding moiety toxin conjugates and to the use of such target-binding moiety toxin conjugates for the preparation of such pharmaceutical compositions. The target-binding moiety toxin conjugates and pharmaceutical compositions of the invention are useful for the treatment of cancer.

18 Claims, 15 Drawing Sheets

Specification includes a Sequence Listing.

(56) References Cited

OTHER PUBLICATIONS

Skolnick, Jeffrey et al., "From genes to protein structure and function: novel applications of computational approaches in the genomic era," *Tibtech*, Jan. 2000, 18:34-39.
Zhelev, Zhivko et al., "Cytotoxicity on L1210 Leukemic Cells of Beta-Amanitin-Concanavalin A and Phallacidin-Concanavalin A Conjugates," *Toxicon*, 1990, 28(11):1360-1363.
Zhelev, Zhivko et al., "Preparation of a β-Amanitin-Concanavalin A Conjugate of Low Toxicity," *Toxicon*, 1987, 25(9):981-987.
Chen, N., et al., "Polyclonal amanitin-specific antibodies: production and cytoprotective properties in vitro." Biochemical Pharmacology, Jul. 1993, 46(2): 327-329.
Faulstich, H., et al., "A rapid radioimmunoassay, using a nylon support, for amatoxins from Amanita mushrooms." Toxicon, Jan. 1982, 20(5): 913-924.
Barbanti-Brodano, G. et al., "Selective Killing of Macrophages by Amanitin-Albumin Conjugates," Nature New Biology, Jun. 27, 1973, vol. 243, No. 130, pp. 281-283.
Cessi, C. et al., "Increased toxicity of beta-amanitin when bound to a protein," Toxicon, May 1, 1969, vol. 6, No. 4, pp. 309-310.

* cited by examiner

| | $R_1$ | $R_2$ | $R_3$ | $R_4$ |
|---|---|---|---|---|
| α-amanitin | OH | OH | $NH_2$ | OH |
| β-amanitin | OH | OH | OH | OH |
| γ-amanitin | H | OH | $NH_2$ | OH |
| ε-amanitin | H | OH | OH | OH |
| amanin | OH | OH | OH | H |
| amaninamide | OH | OH | $NH_2$ | H |
| amanullin | H | H | $NH_2$ | OH |
| amanullinic acid | H | H | OH | OH |

SEQUENCE LISTING

```
<160> NUMBER OF SEQ ID NOS: 28

<210> SEQ ID NO 1
<211> LENGTH: 514
<212> TYPE: PRT
<213> ORGANISM: Artificial
<220> FEATURE:
<223> OTHER INFORMATION: chimeric antibody huHEA125, heavy chain,
      membrane-bound form

<400> SEQUENCE: 1

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Phe
            20                  25                  30

Trp Met Thr Trp Val Arg Gln Ala Pro Gly Lys Gly Leu Glu Trp Ile
        35                  40                  45

Gly Glu Ile Asn Leu Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Phe
65                  70                  75                  80

Leu Gln Met Ser Lys Val Arg Ser Glu Asp Thr Ala Leu Tyr Tyr Cys
                85                  90                  95

Ser Arg Gly Ile Ser Met Asp Tyr Trp Gly Gln Gly Thr Ser Val Thr
```

-continued

```
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Leu Gln Leu Asp
        435                 440                 445

Glu Thr Cys Ala Glu Ala Gln Asp Gly Glu Leu Asp Gly Leu Trp Thr
    450                 455                 460

Thr Ile Thr Ile Phe Ile Ser Leu Phe Leu Leu Ser Val Cys Tyr Ser
465                 470                 475                 480

Ala Ala Val Thr Leu Phe Lys Val Lys Trp Ile Phe Ser Ser Val Val
                485                 490                 495

Glu Leu Lys Gln Thr Leu Val Pro Glu Tyr Lys Asn Met Ile Gly Gln
            500                 505                 510

Ala Pro
```

<210> SEQ ID NO 2
<211> LENGTH: 445
<212> TYPE: PRT
<213> ORGANISM: Artificial
<220> FEATURE:
<223> OTHER INFORMATION: chimeric antibody huHEA125, heavy chain, secreted form

<400> SEQUENCE: 2

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Phe
            20                  25                  30

Trp Met Thr Trp Val Arg Gln Ala Pro Gly Lys Gly Leu Glu Trp Ile
        35                  40                  45

Gly Glu Ile Asn Leu Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Phe
65                  70                  75                  80

Leu Gln Met Ser Lys Val Arg Ser Glu Asp Thr Ala Leu Tyr Tyr Cys
                85                  90                  95

Ser Arg Gly Ile Ser Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365
```

```
Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 3
<211> LENGTH: 115
<212> TYPE: PRT
<213> ORGANISM: Artificial
<220> FEATURE:
<223> OTHER INFORMATION: chimeric antibody huHEA125, heavy chain, VH
      domain

<400> SEQUENCE: 3

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Phe
            20                  25                  30

Trp Met Thr Trp Val Arg Gln Ala Pro Gly Lys Gly Leu Glu Trp Ile
        35                  40                  45

Gly Glu Ile Asn Leu Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Phe
65                  70                  75                  80

Leu Gln Met Ser Lys Val Arg Ser Glu Asp Thr Ala Leu Tyr Tyr Cys
                85                  90                  95

Ser Arg Gly Ile Ser Met Asp Tyr Trp Gly Gln Gly Thr Ser Val Thr
            100                 105                 110

Val Ser Ser
        115


<210> SEQ ID NO 4
<211> LENGTH: 75
<212> TYPE: DNA
<213> ORGANISM: Artificial
<220> FEATURE:
<223> OTHER INFORMATION: chimeric antibody huHEA125, heavy chain, FR1
      segment

<400> SEQUENCE: 4

gaagtgaagc ttctcgagtc tggaggtggc ctggtgcagc ctggaggatc cctgaaactc      60

tcctgtgcag cctca                                                       75


<210> SEQ ID NO 5
<211> LENGTH: 24
<212> TYPE: DNA
<213> ORGANISM: Artificial
<220> FEATURE:
<223> OTHER INFORMATION: chimeric antibody huHEA125, heavy chain, CDR1
      segment

<400> SEQUENCE: 5

ggattcgatt ttagtagatt ctgg                                             24
```

<210> SEQ ID NO 6
<211> LENGTH: 51
<212> TYPE: DNA
<213> ORGANISM: Artificial
<220> FEATURE:
<223> OTHER INFORMATION: chimeric antibody huHEA125, heavy chain, FR2 segment

<400> SEQUENCE: 6
atgacttggg tccggcaggc tccagggaaa gggctagaat ggattggaga a 51

<210> SEQ ID NO 7
<211> LENGTH: 24
<212> TYPE: DNA
<213> ORGANISM: Artificial
<220> FEATURE:
<223> OTHER INFORMATION: chimeric antibody huHEA125, heavy chain, CDR2 segment

<400> SEQUENCE: 7
attaatctag atagcagtac gata 24

<210> SEQ ID NO 8
<211> LENGTH: 114
<212> TYPE: DNA
<213> ORGANISM: Artificial
<220> FEATURE:
<223> OTHER INFORMATION: chimeric antibody huHEA125, heavy chain, FR3 segment

<400> SEQUENCE: 8
aactatacgc catctctaaa ggataaattc atcatctcca gggacaacgc caaaaatacg 60
ctgttcctgc aaatgagcaa agtgagatct gaggacacag ccctttatta ctgt 114

<210> SEQ ID NO 9
<211> LENGTH: 24
<212> TYPE: DNA
<213> ORGANISM: Artificial
<220> FEATURE:
<223> OTHER INFORMATION: chimeric antibody huHEA125, heavy chain, CDR3 segment

<400> SEQUENCE: 9
tcaagaggta tttctatgga ctac 24

<210> SEQ ID NO 10
<211> LENGTH: 33
<212> TYPE: DNA
<213> ORGANISM: Artificial
<220> FEATURE:
<223> OTHER INFORMATION: chimeric antibody huHEA125, heavy chain, FR4 segment

<400> SEQUENCE: 10
tggggtcagg gaacctcagt caccgtctcc tca 33

<210> SEQ ID NO 11
<211> LENGTH: 214
<212> TYPE: PRT
<213> ORGANISM: Artificial
<220> FEATURE:
<223> OTHER INFORMATION: chimeric antibody huHEA125, light chain

<400> SEQUENCE: 11

Asp Ile Leu Leu Thr Gln Ser Pro Ala Ile Leu Ser Val Ser Pro Gly
1 5 10 15

```
Glu Arg Val Ser Phe Ser Cys Arg Ala Ser Gln Ser Ile Gly Ile Ser
            20                  25                  30

Leu His Trp Tyr Gln Gln Arg Pro Ser Asp Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ile Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 12
<211> LENGTH: 107
<212> TYPE: PRT
<213> ORGANISM: Artificial
<220> FEATURE:
<223> OTHER INFORMATION: chimeric antibody huHEA125, light chain, VL
      domain

<400> SEQUENCE: 12

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Ile Ser
            20                  25                  30

Leu His Trp Tyr Gln Gln Arg Pro Ser Asp Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ile Trp Pro Thr
                85                  90                  95

Thr Phe Gly Ala Gly Thr Lys Leu Glu Leu Lys
            100                 105


<210> SEQ ID NO 13
<211> LENGTH: 78
<212> TYPE: DNA
<213> ORGANISM: Artificial
<220> FEATURE:
<223> OTHER INFORMATION: chimeric antibody huHEA125, light chain, FR1
```

segment

<400> SEQUENCE: 13
gacatcttgc tgactcagtc tccagccatc ctgtctgtga gtccaggaga aagagtcagt 60
ttctcctgca gggccagt 78

<210> SEQ ID NO 14
<211> LENGTH: 18
<212> TYPE: DNA
<213> ORGANISM: Artificial
<220> FEATURE:
<223> OTHER INFORMATION: chimeric antibody huHEA125, light chain, CDR1 segment

<400> SEQUENCE: 14
cagagcattg gcataagt 18

<210> SEQ ID NO 15
<211> LENGTH: 51
<212> TYPE: DNA
<213> ORGANISM: Artificial
<220> FEATURE:
<223> OTHER INFORMATION: chimeric antibody huHEA125, light chain, FR2 segment

<400> SEQUENCE: 15
ttacactggt atcagcaaag accaagtgat tctccaaggc ttctcataaa g 51

<210> SEQ ID NO 16
<211> LENGTH: 9
<212> TYPE: DNA
<213> ORGANISM: Artificial
<220> FEATURE:
<223> OTHER INFORMATION: chimeric antibody huHEA125, light chain, CDR2 segment

<400> SEQUENCE: 16 tatgcttct 9

<210> SEQ ID NO 17
<211> LENGTH: 108
<212> TYPE: DNA
<213> ORGANISM: Artificial
<220> FEATURE:
<223> OTHER INFORMATION: chimeric antibody huHEA125, light chain, FR3 segment

<400> SEQUENCE: 17
gagtcaatct ctgggatccc ttccaggttt agtggcagtg gatcagggac agattttact 60
cttagcatca acagtgtgga gtctgaagat attgcagatt attactgt 108

<210> SEQ ID NO 18
<211> LENGTH: 27
<212> TYPE: DNA
<213> ORGANISM: Artificial
<220> FEATURE:
<223> OTHER INFORMATION: chimeric antibody huHEA125, light chain, CDR3 segment

<400> SEQUENCE: 18
caacaaagta atatctggcc aaccacg 27

<210> SEQ ID NO 19
<211> LENGTH: 30
<212> TYPE: DNA

<213> ORGANISM: Artificial
<220> FEATURE:
<223> OTHER INFORMATION: chimeric antibody huHEA125, light chain, FR4 segment

<400> SEQUENCE: 19
ttcggtgctg ggaccaagct ggagctgaaa 30

<210> SEQ ID NO 20
<211> LENGTH: 8
<212> TYPE: PRT
<213> ORGANISM: Artificial
<220> FEATURE:
<223> OTHER INFORMATION: chimeric antibody huHEA125, heavy chain, CDR1 domain

<400> SEQUENCE: 20

Gly Phe Asp Phe Ser Arg Phe Trp
1 5

<210> SEQ ID NO 21
<211> LENGTH: 8
<212> TYPE: PRT
<213> ORGANISM: Artificial
<220> FEATURE:
<223> OTHER INFORMATION: chimeric antibody huHEA125, heavy chain, CDR2 domain

<400> SEQUENCE: 21

Ile Asn Leu Asp Ser Ser Thr Ile
1 5

<210> SEQ ID NO 22
<211> LENGTH: 8
<212> TYPE: PRT
<213> ORGANISM: Artificial
<220> FEATURE:
<223> OTHER INFORMATION: chimeric antibody huHEA125, heavy chain, CDR3 domain

<400> SEQUENCE: 22

Ser Arg Gly Ile Ser Met Asp Tyr
1 5

<210> SEQ ID NO 23
<211> LENGTH: 6
<212> TYPE: PRT
<213> ORGANISM: Artificial
<220> FEATURE:
<223> OTHER INFORMATION: chimeric antibody huHEA125, light chain, CDR1 domain

<400> SEQUENCE: 23

Gln Ser Ile Gly Ile Ser
1 5

<210> SEQ ID NO 24
<211> LENGTH: 3
<212> TYPE: PRT
<213> ORGANISM: Artificial
<220> FEATURE:
<223> OTHER INFORMATION: chimeric antibody huHEA125, light chain, CDR2 domain

<400> SEQUENCE: 24

Tyr Ala Ser
1

<210> SEQ ID NO 25
<211> LENGTH: 9
<212> TYPE: PRT
<213> ORGANISM: Artificial
<220> FEATURE:
<223> OTHER INFORMATION: chimeric antibody huHEA125, light chain, CDR3 domain

<400> SEQUENCE: 25

```
Gln Gln Ser Asn Ile Trp Pro Thr Thr
1               5
```

<210> SEQ ID NO 26
<211> LENGTH: 399
<212> TYPE: PRT
<213> ORGANISM: Artificial
<220> FEATURE:
<223> OTHER INFORMATION: chimeric antibody huHEA125, heavy chain, constant domain, membrane-bound form

<400> SEQUENCE: 26

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Leu Gln Leu Asp Glu Thr Cys
                325                 330                 335

Ala Glu Ala Gln Asp Gly Glu Leu Asp Gly Leu Trp Thr Thr Ile Thr
            340                 345                 350

Ile Phe Ile Ser Leu Phe Leu Leu Ser Val Cys Tyr Ser Ala Ala Val
        355                 360                 365

Thr Leu Phe Lys Val Lys Trp Ile Phe Ser Ser Val Val Glu Leu Lys
    370                 375                 380

Gln Thr Leu Val Pro Glu Tyr Lys Asn Met Ile Gly Gln Ala Pro
385                 390                 395


<210> SEQ ID NO 27
<211> LENGTH: 330
<212> TYPE: PRT
<213> ORGANISM: Artificial
<220> FEATURE:
<223> OTHER INFORMATION: chimeric antibody huHEA125, heavy chain,
      constant domain, secreted form

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

-continued

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 28
<211> LENGTH: 107
<212> TYPE: PRT
<213> ORGANISM: Artificial
<220> FEATURE:
<223> OTHER INFORMATION: chimeric antibody huHEA125, light chain,
      constant domain

<400> SEQUENCE: 28

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

AMATOXIN-ARMED THERAPEUTIC CELL SURFACE BINDING COMPONENTS DESIGNED FOR TUMOUR THERAPY

CROSS-REFERENCE TO RELATED APPLICATIONS

This application is a continuation application of application Ser. No. 13/263,287, filed Dec. 28, 2011; issued as U.S. Pat. No. 9,233,173, which is a National Stage Application of International Application Number PCT/EP2010/002205, filed Apr. 8, 2010; which claims the benefit of U.S. Provisional Application Ser. No. 61/167,690, filed Apr. 8, 2009; and U.S. Provisional Application Ser. No. 61/222,227, filed Jul. 1, 2009; all of which are incorporated herein by reference in their entirety.

The Sequence Listing for this application is labeled "SeqList-28Dec2011.txt", which was created on Dec. 28, 2011, and is 25 KB. The entire content is incorporated herein by reference in its entirety.

FIELD OF THE INVENTION

The invention relates to tumour therapy. In one aspect, the present invention relates to conjugates of a toxin and a target-binding moiety, e.g. an antibody, which are useful in the treatment of cancer. In particular, the toxin is an amatoxin, and the target-binding moiety is preferably directed against tumour-associated antigens. In particular, the amatoxin is conjugated to the antibody by linker moieties. In particular the linker moieties are covalently bound to functional groups located in positions of the amatoxin proved as preferred positions for the attachment of linkers with respect to optimum antitumor activity. In a further aspect the invention relates to pharmaceutical compositions comprising such target-binding moiety toxin conjugates and to the use of such target-binding moiety toxin conjugates for the preparation of such pharmaceutical compositions. The target-binding moiety toxin conjugates and pharmaceutical compositions of the invention are useful for the treatment of cancer.

BACKGROUND OF THE INVENTION AND STATE OF THE ART

Antibody therapy has been established for the targeted treatment of patients with cancer, immunological and angiogenic disorders. The use of antibody-drug conjugates (ADC), i.e. immunoconjugates, for the local delivery of cytotoxic or cytostatic agents, i.e. drugs to kill or inhibit tumor cells in the treatment of cancer theoretically allows targeted delivery of the drug moiety to tumors, and intracellular accumulation therein, where systemic administration of these unconjugated drug agents may result in unacceptable levels of toxicity to normal cells as well as the tumor cells sought to be. Maximal efficacy with minimal toxicity is sought thereby. Efforts to design and refine ADC have focused on the selectivity of monoclonal antibodies (mAbs) as well as drug-linking and drug-releasing properties. Both polyclonal antibodies and monoclonal antibodies have been reported as useful in these strategies.

Amatoxins

Amatoxins are cyclic peptides composed of 8 amino acids. They can be isolated from *Amanita phalloides* mushrooms or prepared from the building blocks by synthesis. Amatoxins specifically inhibit the DNA-dependent RNA polymerase II of mammalian cells, and thereby also the transcription and protein biosynthesis of the affected cells.

Inhibition of transcription in a cell causes stop of growth and proliferation. Though not covalently bound, the complex between amanitin and RNA-polymerase II is very tight ($K_D$=3 nM). Dissociation of amanitin from the enzyme is a very slow process what makes recovery of an affected cell unlikely. When the inhibition of transcription lasts too long, the cell will undergo programmed cell death (apoptosis).

Conjugates of Amatoxins and Target-binding Moieties

Earlier patent application EP 1 859 811 A1 (published Nov. 28, 2007) by the inventors describes conjugates, in which β-amanitin is coupled to albumin or to the monoclonal antibodies HEA125, OKT3, and PA-1. Furthermore, the inhibitory effect of these conjugates on the proliferation of breast cancer cells (MCF-7), Burkitt's lymphoma cells (Raji), and T-lymphoma cells (Jurkat) was studied.

Epithelial Cell Adhesion Molecule (EpCAM) Antigen

Epithelial cell adhesion molecule (EpCAM, CD326) is one of the best-studied target antigens on human tumors (Trzpis et al., 2007; Baeuerle and Gires, 2007). It represents a type I membrane glycoprotein of 314 amino acids with an apparent molecular weight of 40 kDa (Balzar et al., 1999). It is overexpressed in the majority of adenocarcinomas (Winter et al., 2003; Went et al., 2004). In particular, EpCAM expression is enhanced in node-positive breast cancer, epithelial ovarian cancer, cholangiocarcinoma, pancreatic adenocarcinoma and squamous cell head and neck cancer. Increased EpCAM expression is indicative for a poor prognosis in breast and gallbladder carcinomas (Gastl et al., 2000; Varga et al., 2004; Spizzo et al., 2002; Spizzo et al., 2004). Importantly, EpCAM is expressed by tumor initiating or cancer stem cells in mammary, colorectal and pancreatic carcinomas (Al-Hajj et al., 2003; Dalerba et al., 2007; Li et al., 2007).

EpCAM-specific monoclonal antibodies have been used as a diagnostic tool for the detection of rare circulating tumor cells in cancer patients (Allard et al., 2004; Nagrath et al., 2007). A couple of engineered anti-EpCAM antibodies are currently investigated in clinical studies.

HER2 Antigen

HER2 (Her2/neu; ErbB2), a receptor tyrosine kinase with an apparent molecular weight of 185 kDa is overexpressed in about 25-30% of human breast cancers and gastric cancers. This overexpression, which is often due to amplification of the receptor-encoding gene, generally represents a poor prognosis, often involving progressive disease in the years after the initial diagnosis is made.

Monoclonal antibody therapy has been established for the targeted treatment of patients with Her2/neu-positive cancers. HERCEPTIN® (trastuzumab) is a recombinant DNA-derived humanized monoclonal antibody that selectively binds with high affinity in a cell-based assay (Kd=5 nM) to the extracellular domain of the human epidermal growth factor receptor 2 protein, HER2 (ErbB2). Trastuzumab is an IgG1 kappa antibody that contains human framework regions with the complementarity-determining regions of a murine antibody (4D5) that binds to HER2. Trastuzumab binds to the HER2 antigen and thus inhibits the growth of cancerous cells. Because trastuzumab is a humanized antibody, it minimizes any HAMA response in patients. Trastuzumab has been shown, in both in vitro assays and in animals, to inhibit the proliferation of human tumor cells that overexpress HER2. Trastuzumab is a mediator of antibody-dependent cellular cytotoxicity, ADCC. HERCEPTIN® is clinically active in patients with ErbB2-overexpressing metastatic breast cancers that have received extensive prior anti-cancer therapy. Although HERCEPTIN® is a breakthrough in treating patients with ErbB2- overexpressing breast cancers that have received extensive prior anti-cancer therapy, the majority of the patients in this population fail to respond or respond only poorly to HERCEPTIN® treatment. Therefore, there is a significant clinical need for developing further HER2-directed cancer therapies for those patients with HER2-overexpressing tumors or other diseases associated with HER2 expression that do not respond, or respond poorly, to HERCEPTIN® treatment.

Technical Problems Underlying the Present Invention

There was a need in the prior art for target-binding moiety toxin conjugates that exert their toxic effects to target cells or tissues at much lower concentration so that the conjugates may be administered at lower concentrations and harmful side effects to non-target cells are minimized. Furthermore, there was a need in the prior art for the treatment of other types of cancer, particularly those being therapy resistant, or poorly responding to actual tumour therapies.

The present invention fulfils these and other needs. For example, the inventors found out in the experiments underlying the present invention that very effective target-binding moiety toxin conjugates, in particular antibody amatoxin conjugates, can be constructed by choosing particular linkage points in the amatoxin part of the conjugate and by choosing particular linker compounds. Such target-binding moiety toxin conjugates are very effective in that they exert their toxic activity to the target cells at very low concentrations ($IC_{50}$ of about $5\times10^{-12}$ M) as well as by being highly specific for their target cells. Without wishing to be bound by a particular theory, these advantages might be explained in that the linkage between the target-binding moiety and the amatoxin or, if present, between the linker and the amatoxin is efficiently cleaved inside the target cell and to a much lesser degree outside the cell.

The above overview does not necessarily describe all problems solved by the present invention.

SUMMARY OF THE INVENTION

In a first aspect the present invention relates to a target-binding moiety toxin conjugate comprising: (i) a target-binding moiety; (ii) at least one amatoxin; and (iii) optionally a linker L2; wherein the at least one amatoxin is connected to the target-binding moiety or, if present, to the linker L2 via the 6' C-atom of amatoxin amino acid 4.

In a second aspect the present invention relates to a target-binding moiety toxin conjugate comprising: (i) a target-binding moiety; (ii) at least one amatoxin; and (iii) optionally a linker L3; wherein the at least one amatoxin is connected to the target-binding moiety or, if present, to the linker L3 via the δ C-atom of amatoxin amino acid 3.

In a third aspect the present invention relates to a target-binding moiety toxin conjugate comprising: (i) a target-binding moiety; (ii) at least one amatoxin; and (iii) optionally a linker L1; wherein the at least one amatoxin is connected to the target-binding moiety or, if present, to the linker L1 via the γ C-atom of amatoxin amino acid 1.

In a fourth aspect the present invention relates to the target-binding moiety toxin conjugate according to the first, the second, or the third aspect for use in medicine.

In a fifth aspect the present invention relates to the target-binding moiety toxin conjugate according to the first, the second, the third or the fourth aspect for the treatment of cancer or of an autoimmune disease in a patient, wherein the cancer is preferably selected from the group consisting of pancreatic cancer, cholangiocarcinoma, breast cancer, colorectal cancer, lung cancer, prostate cancer, ovarian cancer, stomach cancer, kidney cancer, head and neck cancer, brain tumors, childhood neoplasms, soft tissue sarcomas, epithelial skin cancer, malignant melanoma, leukemia, and malignant lymphoma and wherein the autoimmune disease is preferably selected from the group consisting of Ankylosing Spondylitis, Chagas disease, Crohns Disease, Dermatomyositis, Diabetes mellitus type 1, Goodpasture's syndrome, Graves' disease, Guillain-Barré syndrome (GBS), Hashimoto's disease, Hidradenitis suppurativa, Idiopathic thrombocytopenic purpura, Lupus erythematosus, Mixed Connective Tissue Disease, Myasthenia gravis, Narcolepsy, Pemphigus vulgaris, Pernicious anaemia, Psoriasis, Psoriatic Arthritis, Polymyositis, Primary biliary cirrhosis, Relapsing polychondritis, Rheumatoid arthritis, Schizophrenia, Sjögren's syndrome, Temporal arteritis, Ulcerative Colitis, Vasculitis Wegener's granulomatosis, in particular Rheumatoid arthritis.

In a sixth aspect the present invention relates to a pharmaceutical composition comprising at least one type of target-binding moiety toxin conjugate according to the first, the second, and/or the third aspect and further comprising one or more pharmaceutically acceptable diluents, carriers, excipients, fillers, binders, lubricants, glidants, disintegrants, adsorbents; and/or preservatives.

This summary of the invention does not necessarily describe all features of the invention.

BRIEF DESCRIPTION OF THE DRAWINGS

FIG. 3A Capan-1; FIG. 3B Colo205; FIG. 3C OZ; and FIG. 3D MCF-7. The grey-shaded histograms on the left side of each diagram show the results obtained with control antibody Xolair®; the histograms having a white area on the right side of each diagram show the results obtained with antibody huHEA125. The abbreviation FL1-H stands for "fluorescence 1 height" which means the intensity of fluorescence 1, i.e. the green channel for FITC.

A: bold histogram, huHEA125-Amanitin1; shaded histogram, huHEA125; dotted histogram, Xolair (negative control);

B: bold histogram, huHEA125-Amanitin4; shaded histogram, huHEA125; dotted histogram, Xolair (negative control);

C: bold histogram, huHEA125-α-Phalloidin; shaded histogram, huHEA125; dotted histogram, Xolair (negative control).

Figure 5:
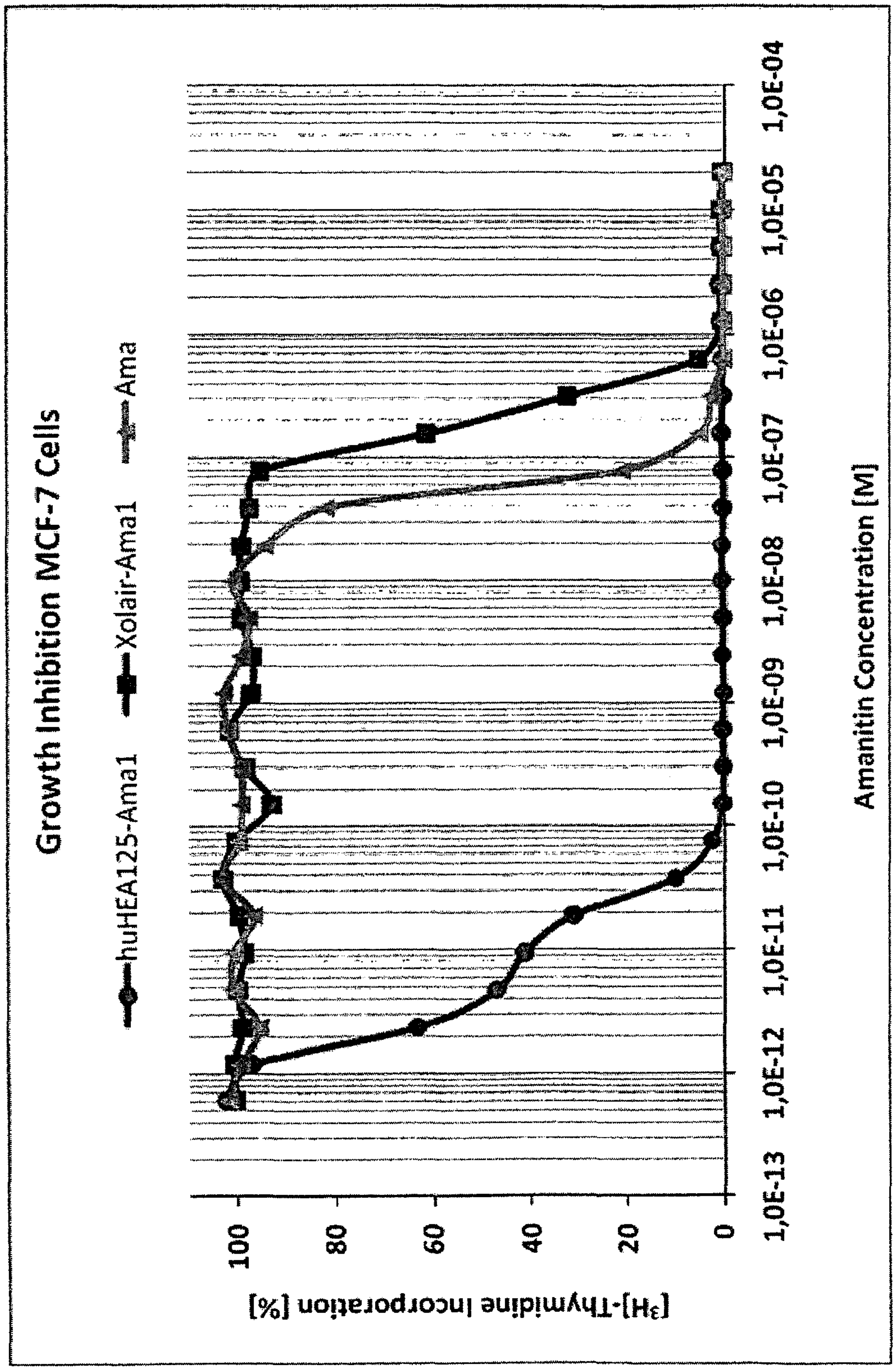

FIG. 5 shows a comparison of the inhibition of MCF-7 cell proliferation caused by the conjugate huHEA125-Amanitin1, the non-binding control conjugate Xolair-Amanitin1, and free Amanitin.

Figure 6:
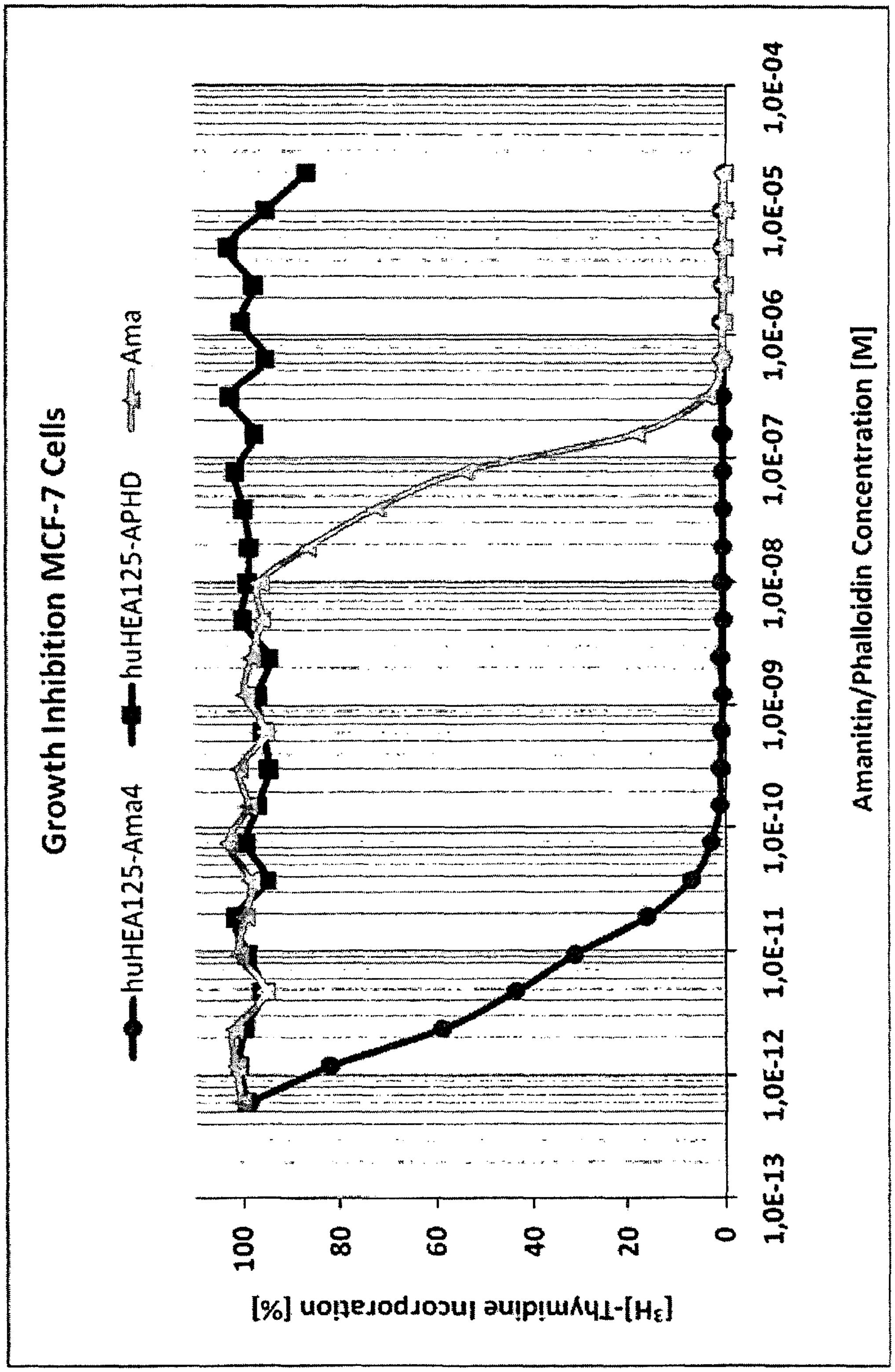

FIG. 6 shows a comparison of the inhibition of MCF-7 cell proliferation caused by the conjugate huHEA125-Amanitin4, the conjugate alpha-phalloidin-huHEA125, and free Amanitin.

Figure 7:
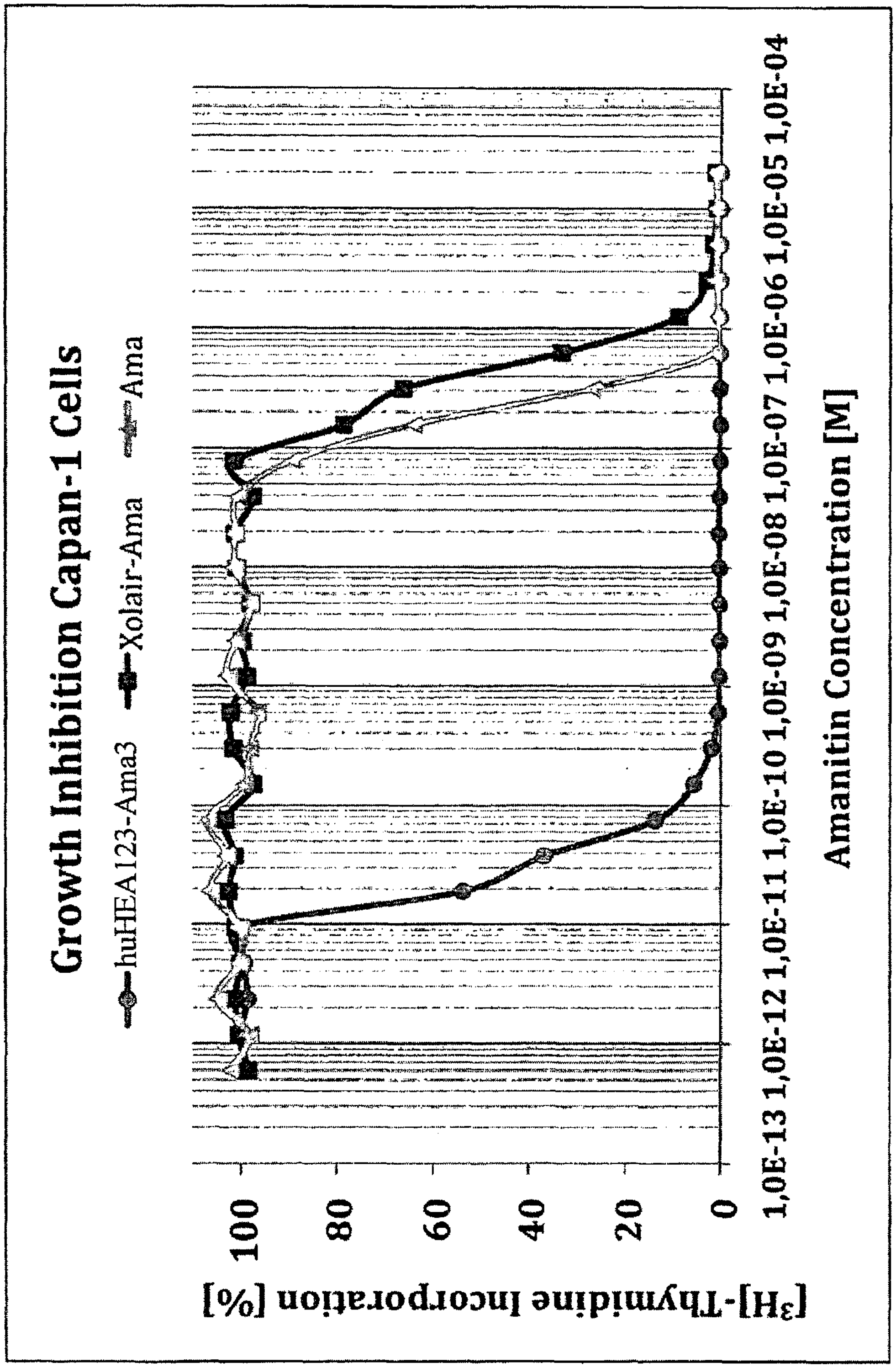

FIG. 7 shows a comparison of the inhibition of Capan-1 cell proliferation caused by conjugate huHEA125-Amanitin3, Amanitin-armed control antibody Xolair®, and free Amanitin.

Figure 8:
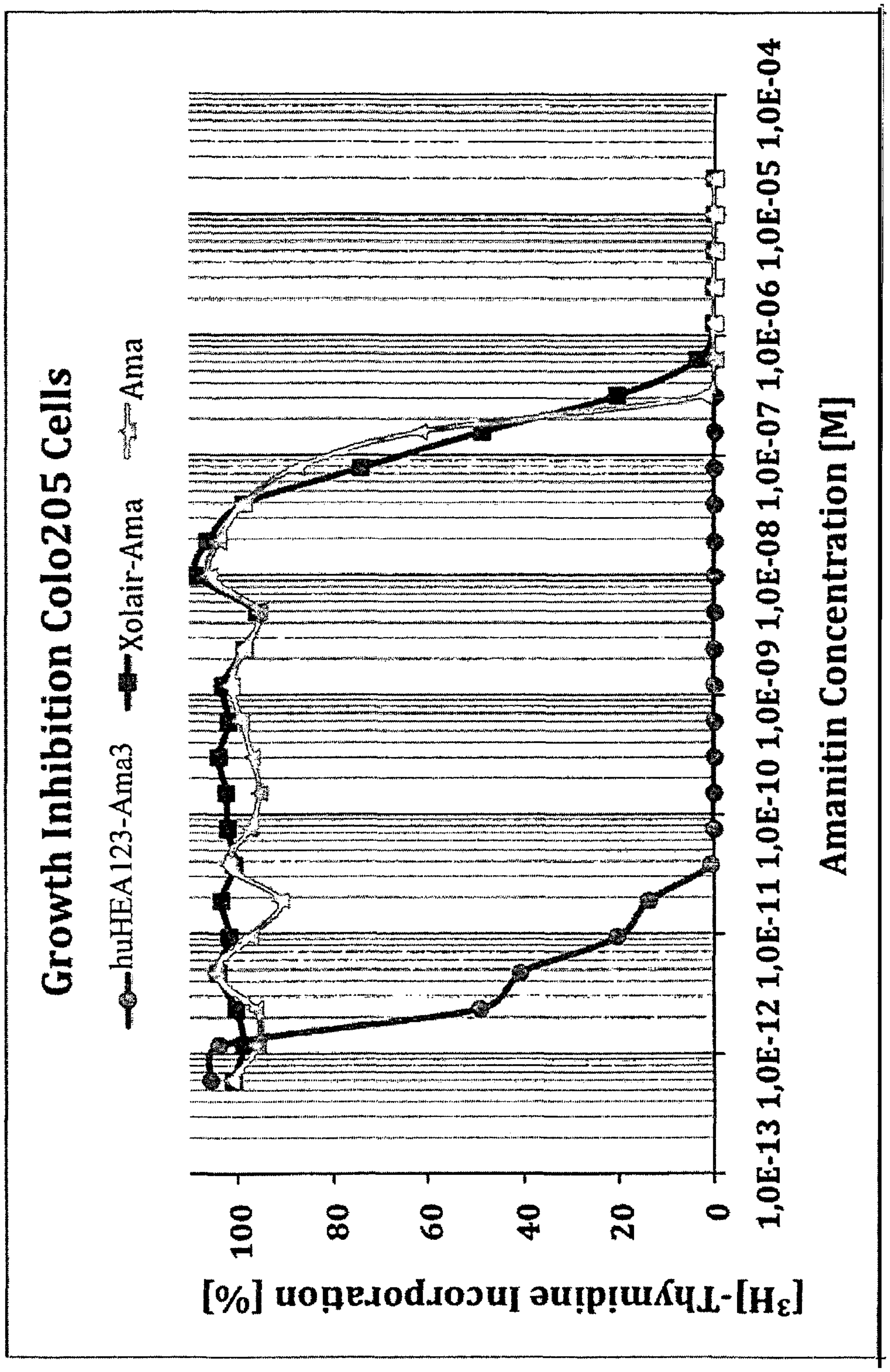

FIG. 8 shows a comparison of the inhibition of Colo205 cell proliferation caused by conjugate huHEA125-Amanitin3, Amanitin-armed control antibody Xolair®, and free Amanitin.

Figure 9:
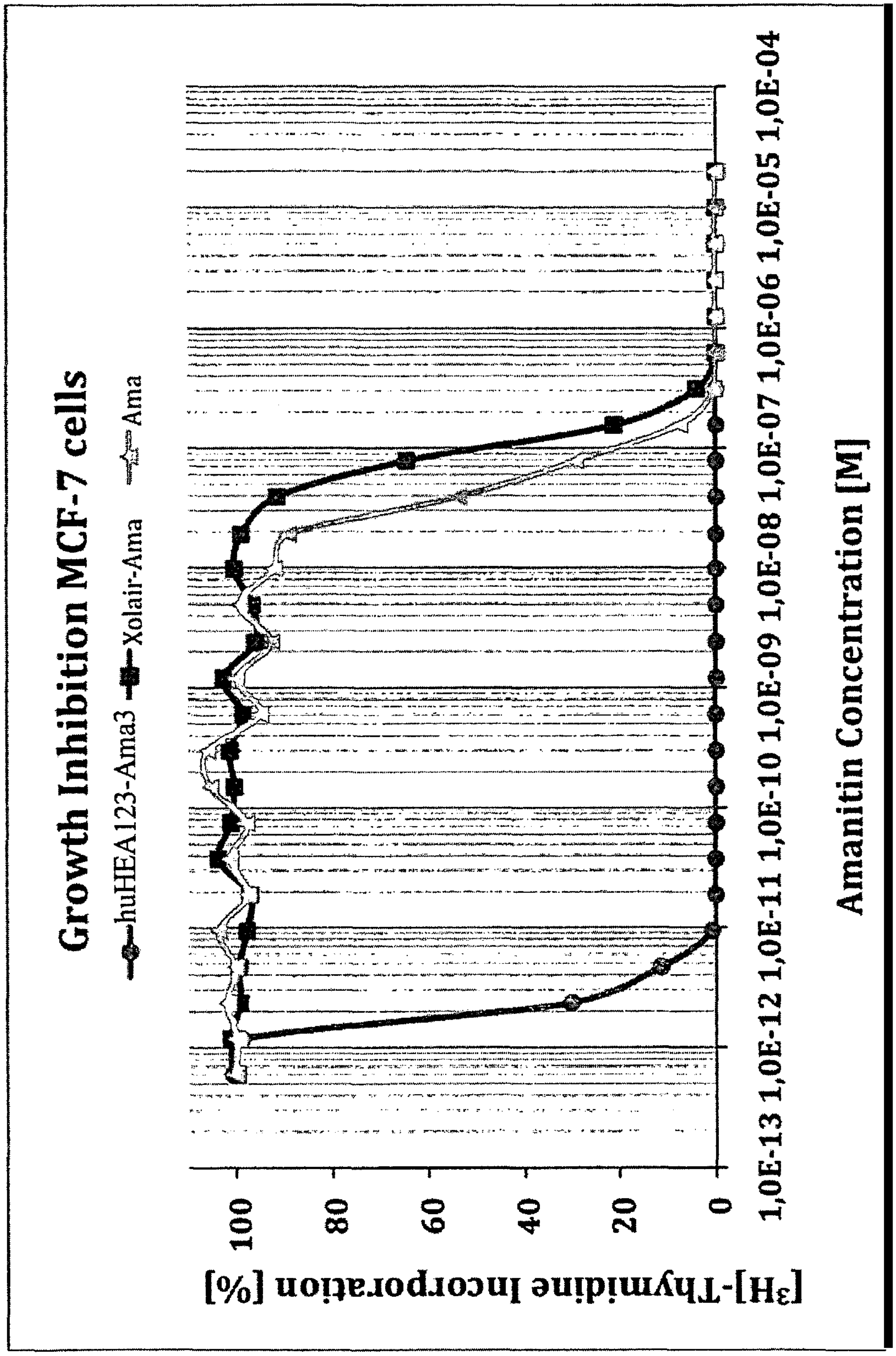

FIG. 9 shows a comparison of the inhibition of MCF-7 cell proliferation caused by conjugate huHEA125-Amanitin3, Amanitin-armed control antibody Xolair®, and free Amanitin.

Figure 10:
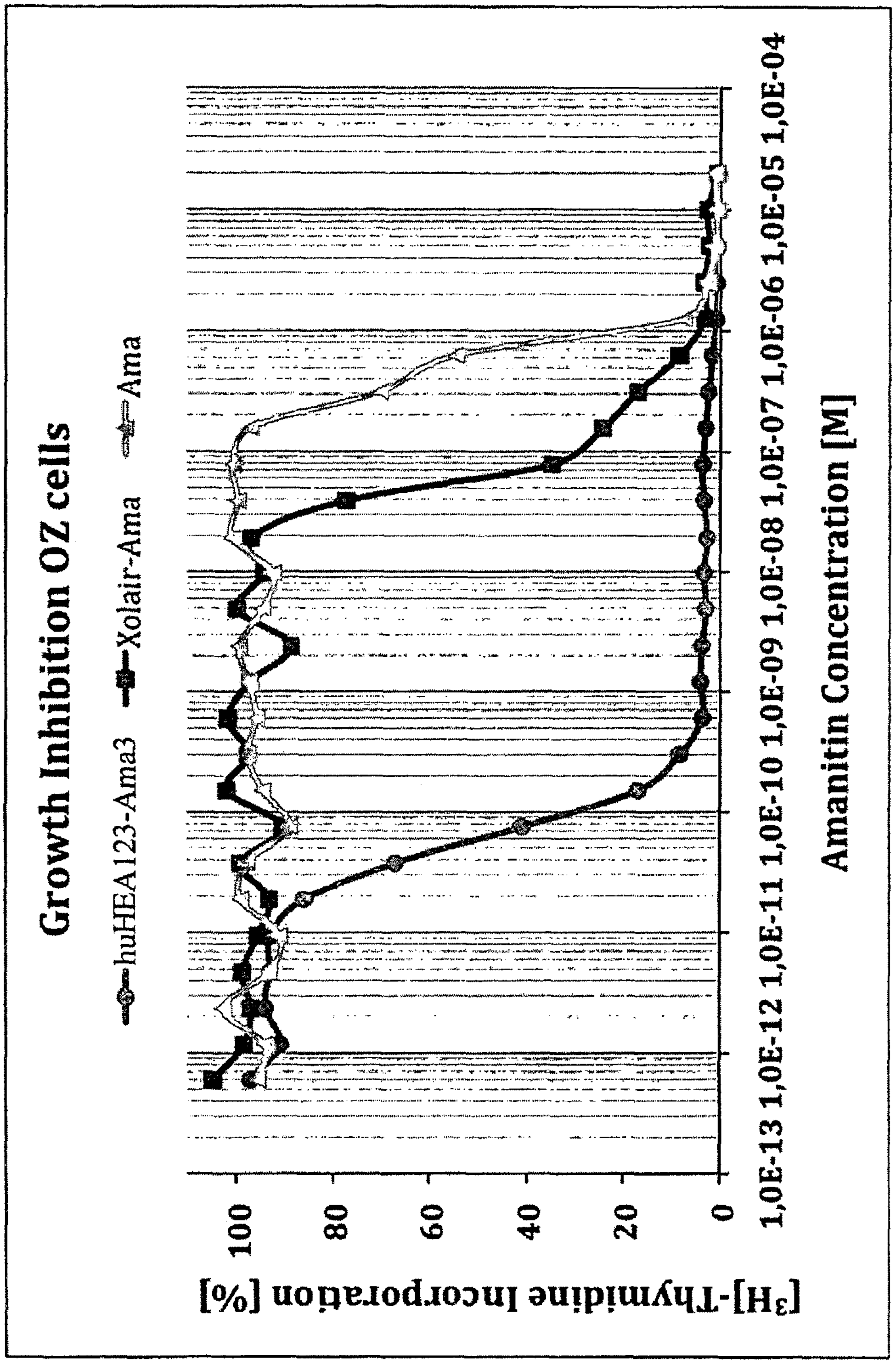
Figure 11A:
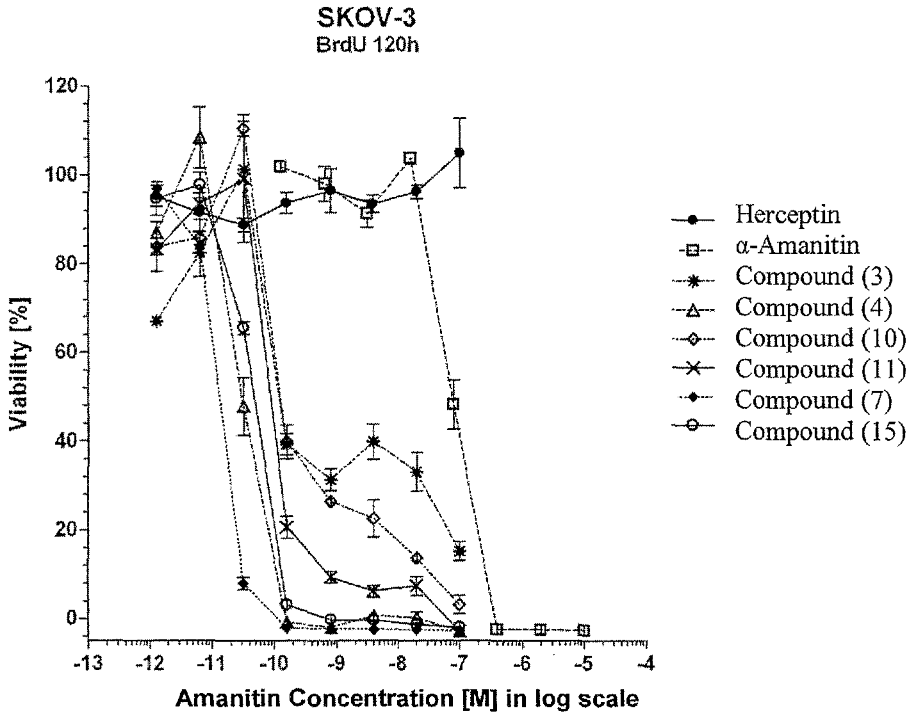
Figure 11B:
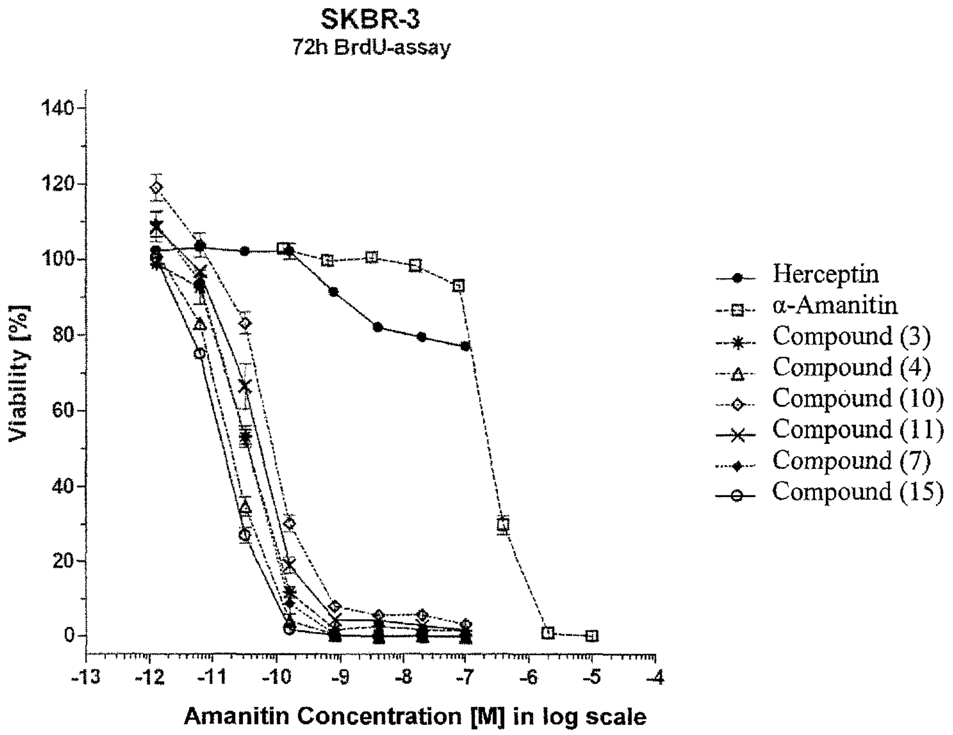
Figure 11C:
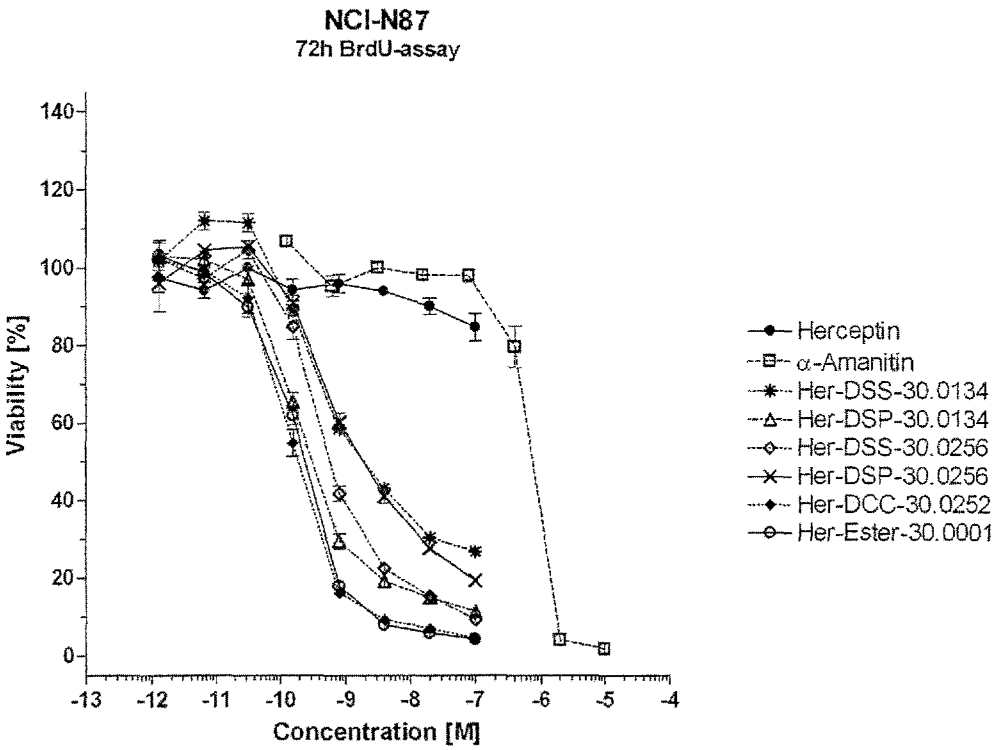
Figure 11D:
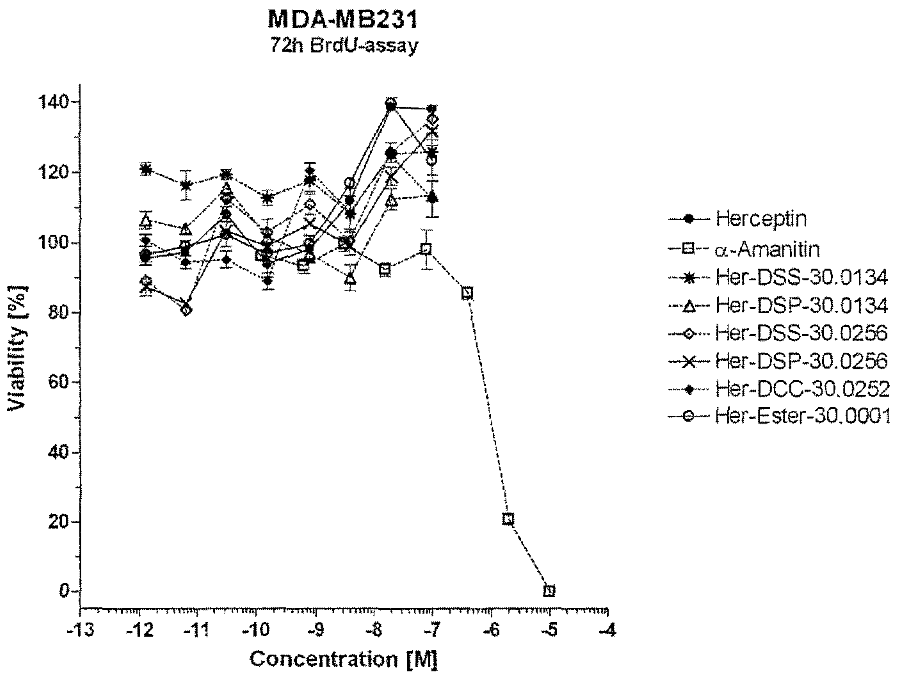

FIG. 10 shows a comparison of the inhibition of OZ cell proliferation caused by conjugate huHEA125-Amanitin3, Amanitin-armed control antibody Xolair®, and free Amanitin.

FIGS. 11A-11D show a comparison of the inhibition on cell proliferation exerted by various α-amanitin conjugates at different amanitin concentrations using the Her2/neu positive cell lines SKOV-3, SKBR-3 and NCI-N87 as well as the Her2/neu negative cell line MDA-MB231.

Figure 12A:
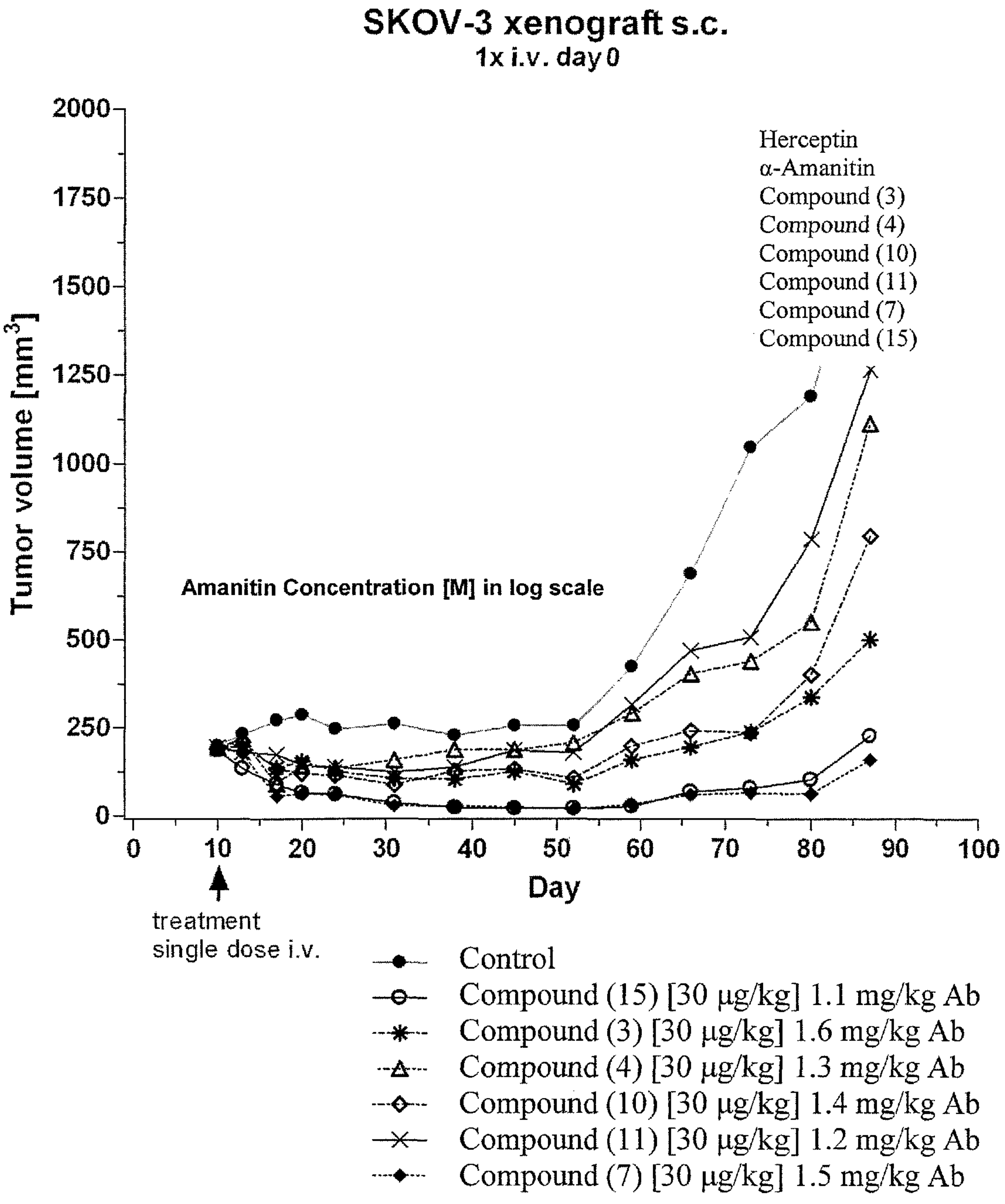
Figure 12B:
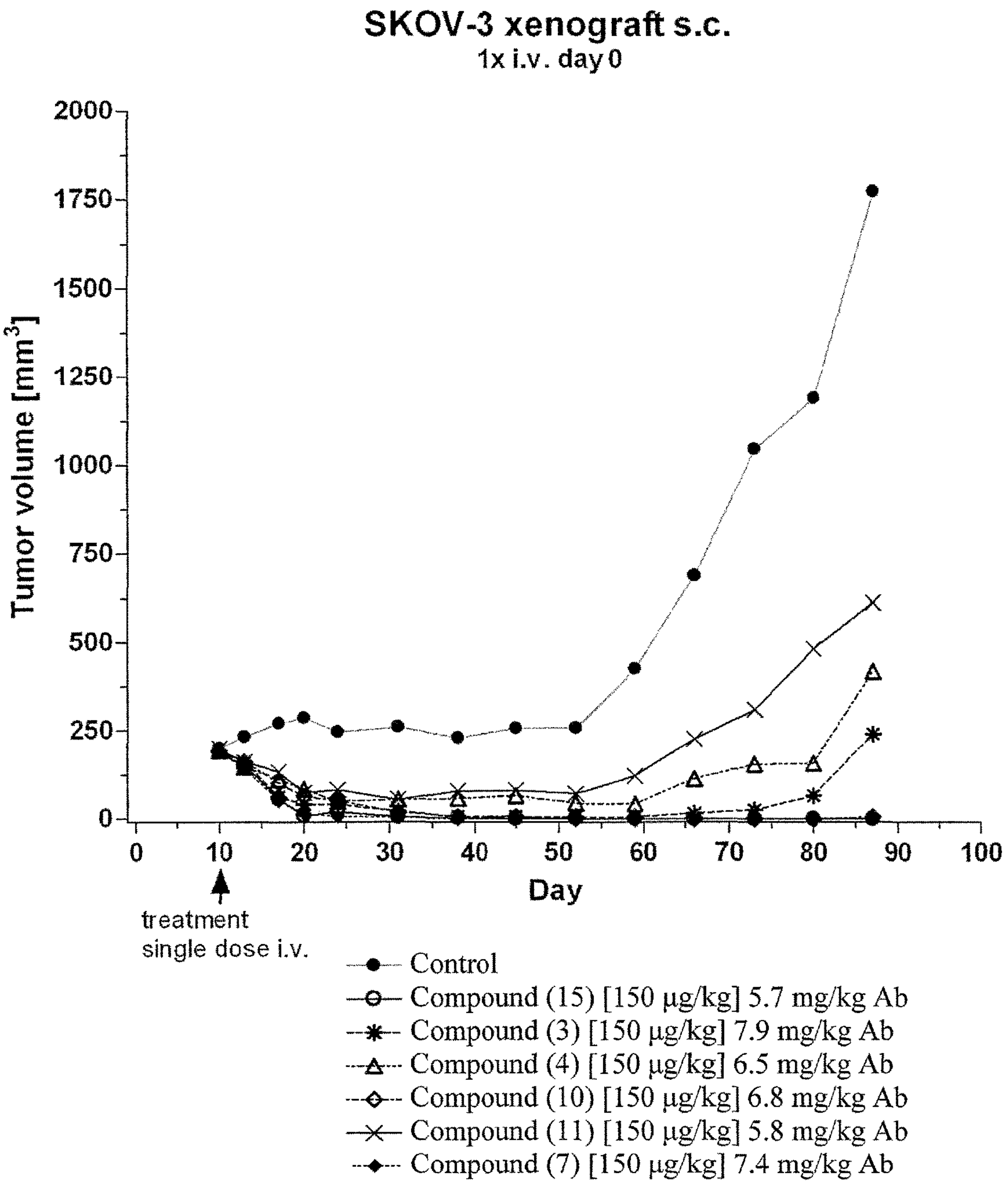

FIGS. 12A-12B show the antitumor activity of various α-amanitin conjugates at two different concentrations (A: 30 μg/kg and B: 150 μg/kg body weight) in an in vivo SKOV-3 xenograft tumor model.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

The term "target-binding moiety", as used herein, refers to any molecule or part of a molecule that can specifically bind to a target molecule or target epitope. Preferred target-binding moieties in the context of the present application are (i) antibodies or antigen-binding fragments thereof; (ii) antibody-like proteins; and (iii) nucleic acid aptamers. "Target-binding moieties" suitable for use in the present invention typically have a molecular mass of at least 15 kDa, at least 20 kDa, at least 30 kDa or of at least 40 kDa or more.

As used herein, an "antibody toxin conjugate" refers to a target-binding moiety toxin conjugate in which the target-binding moiety is an antibody or antigen-binding fragment thereof according to above alternative (i).

As used herein, an "antibody-like protein toxin conjugate" refers to a target-binding moiety toxin conjugate in which the target-binding moiety is an antibody-like protein according to above alternative (ii).

As used herein, an "aptamer conjugate" refers to a target-binding moiety toxin conjugate in which the target-binding moiety is a nucleic acid aptamer according to above alternative (iii).

In the context of the present application the terms "target molecule" and "target epitope", respectively, refers to an antigen and an epitope of an antigen, respectively, that is specifically bound by a target-binding moiety, preferably the target molecule is a tumour-associated antigen, in particular an antigen or an epitope which is present on the surface of one or more tumour cell types in an increased concentration and/or in a different steric configuration as compared to the surface of non-tumour cells or an antigen preferentially expressed on cells involved in autoimmune diseases, examples of such antigens are Immunoglobulin G Fc-part, Thyreotropin-receptor, Type IV Collagen, Proteinase 3, DNA Topoisomerase I, Placoglobin. Preferably, said antigen or epitope is present on the surface of one or more tumour cell types but not on the surface of non-tumour cells.

Preferably the term "tumour associated antigen" comprises all substances, which elicit an immune response against a tumour. Particular suitable substances are those which are enriched in a tumour cell in comparison to a healthy cell. These substances are preferably present within and/or are accessible on the outside of the tumour cell. If the tumour antigen is only present within a tumour cell, it will still be accessible for the immune system, since the antigen or fragments thereof will be presented by the MHC system at the surface of the cell. In a preferred aspect tumour antigen is almost exclusively present on and/or in the tumour cell and not in a healthy cell of the same cell type.

Suitable tumour antigens can be identified, for example, by analyzing the differential expression of proteins between tumour and healthy cells of the same cell type using a microarray-based approach (Russo et al., Oncogene. 2003, 22: 6497-507), by PCR- or microarray-based screening for tumor specific mutated cellular genes (Heller, Annu. Rev. Biomed. Eng. 2002, 4: 129-53) or by serological identification of antigens by recombinant expression cloning (SEREX; Tureci et al., Mol Med Today. 1997, 3: 342-349). The skilled artisan is aware of a large number of substances which are preferentially or exclusively present on and/or in tumor cell, which include for example, oncogenes like, for example truncated epidermal growth factor, folate binding protein, melanoferrin, carcinoembryonic antigen, prostate-specific membrane antigen, HER2-neu and certain sugar chains like, for example, epithelial mucins.

It is preferred that tumour antigens are selected, which elicit a strong immune response, preferentially a MHC class I immune response. Antigens eliciting a strong immune response will induce at least 1%, preferably at least 5%, more preferably at least 10% and most preferably at least 15% IFN-γ-producing $CD8^+$ T or $CD4^+$ T cells isolated from mice previously immunized with the antigen, upon challenge with the antigen and/or will induce preferably at least 5%, and most preferably at least 15% of B-cells cells isolated from mice previously immunized with the antigen, upon challenge with the antigen to proliferate. Antigens fulfilling these criterions are candidates for use in therapeutic and/or prophylactic cancer vaccines.

In a particular preferred embodiment the tumour antigen is selected from the group consisting of T-cell or B-cell-defined cancer-associated antigens belonging to unique gene products of mutated or recombined cellular genes, in particular cyclin-dependent kinases (e.g. CDC2, CDK2, CDK4), $p15^{Ink4b}$, p53, AFP, β-catenin, caspase 8, p53, Bcr-abl fusion product, MUM-1 MUM-2, MUM-3, ELF2M, HSP70-2M, HST-2, KIAA0205, RAGE, myosin/m, 707-AP, CDC27/m, ETV6/AML, TEL/Amll, Dekcain, LDLR/FUT, Pml-RARa, TEL/AMLI; Cancer-testis (CT) antigens, in particular NY-ESO-1, members of the MAGE-family (MAGE-A1, MAGE-A2, MAGE-A3, MAGE-A4, MAGE-A6, MAGE-10, MAGE-12), BAGE, DAM-6, DAM-10, members of the GAGE-family (GAGE-1, GAGE-2, GAGE-3, GAGE-4, GAGE-5, GAGE-6, GAGE-7B, GAGE-8), NY-ESO-1, NA-88A, CAG-3, RCC-associated antigen G250; Tumour virus antigens, in particular human papilloma virus (HPV)-derived E6 or E7 oncoproteins, Epstein Barr virus EBNA2-6, LMP-1, LMP-2; overexpressed or tissue-specific differentiation antigens, in particular gp77, gp100, MART-1/Melan-A, p53, tyrosinase, tyrosinase-related protein (TRP-1 and TPR-2), PSA, PSM, MC1R; widely expressed antigens, in particular ART4, CAMEL, CEA, CypB, EpCAM, HER2/neu, hTERT, hTRT, ICE, Muc1, Muc2, PRAME RU1, RU2, SART-1, SART-2, SART-3, and WT1; and fragments and derivatives thereof. Particular preferred tumour antigens are antigens derived from HER-2 and EpCAM. In the context of this section the term fragment refers to C-terminally and/or N-terminally deleted proteins, which comprise at least one epitope which can be specifically bound by a target-binding moiety.

The term "antibody or antigen binding fragment thereof", as used herein, refers to immunoglobulin molecules and immunologically active portions of immunoglobulin molecules, i.e. molecules that contain an antigen binding site that immunospecifically binds an antigen. Also comprised are immunoglobulin-like proteins that are selected through techniques including, for example, phage display to specifically bind to a target molecule, e.g. to the target protein EpCAM or Her2. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. "Antibodies and antigen-binding fragments thereof" suitable for use in the present invention include, but are not limited to, polyclonal, monoclonal, monovalent, bispecific, heteroconjugate, multispecific, human, humanized (in particular CDR-grafted), deimmunized, or chimeric antibodies, single chain antibodies (e.g. scFv), Fab fragments, $F(ab')_2$ fragments, fragments produced by a Fab expression library, diabodies or tetrabodies (Holliger P. et al., 1993), nanobodies, anti-idiotypic (anti-Id) antibodies (including, e.g., anti-Id antibodies to antibodies of the invention), and epitope-binding fragments of any of the above.

In some embodiments the antigen-binding fragments are human antigen-binding antibody fragments of the present invention and include, but are not limited to, Fab, Fab' and $F(ab')_2$, Fd, single-chain Fvs (scFv), single-chain antibodies, disulfide-linked Fvs (dsFv) and fragments comprising either a VL or VH domain. Antigen-binding antibody fragments, including single-chain antibodies, may comprise the variable domain(s) alone or in combination with the entirety or a portion of the following: hinge region, CL, CH1, CH2, and CH3 domains. Also included in the invention are antigen-binding fragments also comprising any combination of variable domain(s) with a hinge region, CL, CH1, CH2, and CH3 domains.

Antibodies usable in the invention may be from any animal origin including birds and mammals. Preferably, the antibodies are from human, rodent (e.g. mouse, rat, guinea pig, or rabbit), chicken, pig, sheep, goat, camel, cow, horse, donkey, cat, or dog origin. It is particularly preferred that the antibodies are of human or murine origin. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, anticalins, designed ankyrin repeat proteins (for review see: Binz et al. 2005) and proteins with ubiquitine based scaffolds. Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins.

The term "nucleic acid aptamer" refers to a nucleic acid molecule that has been engineered through repeated rounds of in vitro selection or SELEX (systematic evolution of ligands by exponential enrichment) to bind to a target molecule (for a review see: Brody and Gold, 2000). The nucleic acid aptamer may be a DNA or RNA molecule. The aptamers may contain modifications, e.g. modified nucleotides such as 2'-fluorine-substituted pyrimidines.

The term "amatoxin" includes all cyclic peptides composed of 8 amino acids as isolated from the genus *Amanita* and described in ref. (Wieland, T. and Faulstich H., 1978); further all chemical derivatives thereof; further all semisynthetic analogs thereof; further all synthetic analogs thereof built from building blocks according to the master structure of the natural compounds (cyclic, 8 amino acids), further all synthetic or semisynthetic analogs containing non-hydroxylated amino acids instead of the hydroxylated amino acids, further all synthetic or semisynthetic analogs, in which the thioether sulfoxide moiety is replaced by a sulfide, sulfone, or by atoms different from sulfur, e.g. a carbon atom as in a carbaanalog of amanitin.

Figure 1:
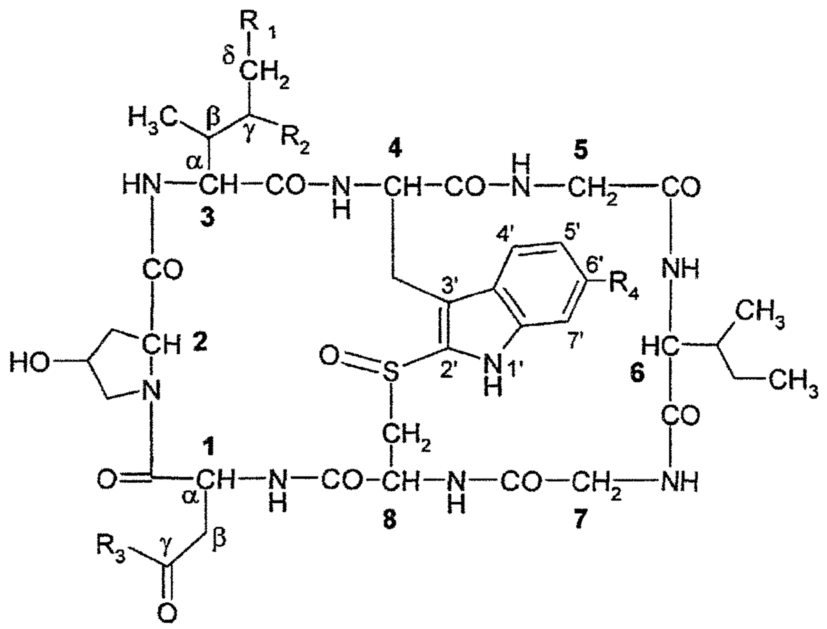
FIG. 1 shows the structural formulae of different amatoxins. The numbers in bold type (1 to 8) designate the standard numbering of the eight amino acids forming the amatoxin. The standard designations of the atoms in amino acids 1, 3 and 4 are also shown (Greek letters α to γ, Greek letters α to δ, and numbers from 1' to 7', respectively).

Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or target-binding moieties as defined above. Amatoxins which are particularly suitable for the conjugates of the present invention are α-amanitin, β-amanitin, γ-amanitin, ε-amanitin, amanin, amaninamide, amanullin, and amanullinic acid as shown in FIG. 1 as well as salts, chemical derivatives, semisynthetic analogs, and synthetic analogs thereof. Particularly preferred amatoxins for use in the present invention are α-amanitin, β-amanitin, and amaninamide.

As used herein, a "chemical derivative" (or short: a "derivative") of a compound refers to a species having a chemical structure that is similar to the compound, yet containing at least one chemical group not present in the compound and/or deficient of at least one chemical group that is present in the compound. The compound to which the derivative is compared is known as the "parent" compound. Typically, a "derivative" may be produced from the parent compound in one or more chemical reaction steps.

As used herein, an "analog" of a compound is structurally related but not identical to the compound and exhibits at least one activity of the compound. The compound to which the analog is compared is known as the "parent" compound. The afore-mentioned activities include, without limitation: binding activity to another compound; inhibitory activity, e.g. enzyme inhibitory activity; toxic effects; activating activity, e.g. enzyme-activating activity. It is not required that the analog exhibits such an activity to the same extent as the parent compound. A compound is regarded as an analog within the context of the present application, if it exhibits the relevant activity to a degree of at least 1% (more preferably at least 5%, more preferably at least 10%, more preferably at least 20%, more preferably at least 30%, more preferably at least 40%, and more preferably at least 50%) of the activity of the parent compound. Thus, an "analog of an amatoxin", as it is used herein, refers to a compound that is structurally related to any one of α-amanitin, β-amanitin, γ-amanitin, ε-amanitin, amanin, amaninamide, amanullin, and amanullinic acid as shown in FIG. 1 and that exhibits at least 1% (more preferably at least 5%, more preferably at least 10%, more preferably at least 20%, more preferably at least 30%, more preferably at least 40%, and more preferably at least 50%) of the inhibitory activity against mammalian RNA polymerase II as compared to at least one of α-amanitin, β-amanitin, γ-amanitin, ε-amanitin, amanin, amaninamide, amanullin, and amanullinic acid. An "analog of an amatoxin" suitable for use in the present invention may even exhibit a greater inhibitory activity against mammalian RNA polymerase II than any one of α-amanitin, β-amanitin, γ-amanitin, ε-amanitin, amanin, amaninamide, amanullin, or amanullinic acid. The inhibitory activity might be measured by determining the concentration at which 50% inhibition occurs ($IC_{50}$ value). The inhibitory activity against mammalian RNA polymerase II can be determined indirectly by measuring the inhibitory activity on cell proliferation. A suitable assay for measuring inhibition of cell proliferation is described in Example 3.

A "semisynthetic analog" refers to an analog that has been obtained by chemical synthesis using compounds from natural sources (e.g. plant materials, bacterial cultures, or cell cultures) as starting material. Typically, a "semisynthetic analog" of the present invention has been synthesized starting from a compound isolated from a mushroom of the *Amanita* family. In contrast, a "synthetic analog" refers to an analog synthesized by so-called total synthesis from small (typically petrochemical) building blocks. Usually, this total synthesis is carried out without the aid of biological processes.

A "linker" in the context of the present application refers to a molecule that increases the distance between two components, e.g. to alleviate steric interference between the target-binding moiety and the amatoxin, which may otherwise decrease the ability of the amatoxin to interact with RNA polymerase II. The linker may serve another purpose as it may facilitate the release of the amatoxin specifically in the cell being targeted by the target binding moiety. It is preferred that the linker and preferably the bond between the linker and the amatoxin on one side and the bond between the linker and the antibody on the other side is stable under the physiological conditions outside the cell, e.g. the blood, while it can be cleaved inside the cell, in particular inside the target cell, e.g. cancer cell or immune cell. To provide this selective stability the linker may comprise functionalities that are preferably pH-sensitive to generate pH-sensitive linkers as described, e.g. in S. Fletcher, M. R. Jorgensens and A. D. Miller; Org. Lett. 2004, 6(23), pp 4245-4248, or protease sensitive to generate protease sensitive linkers as described, e.g. in L. D A Ibsen, Blood 2003, 102, 1458-65 or Francisco J A, Cerreny C G, Meyer D L, Nat. Biotechnol 2003, 21, 778-84. Alternatively, the bond linking the linker to the target binding moiety may provide the selective stability. Preferably a linker has a length of at least 1, preferably of 1-20 atoms length (e.g. 1, 2, 3, 4, 5, 6, 7, 8, 9, 10, 11, 12, 13, 14, 15, 16, 17, 18, 19, or 20 atoms) wherein one side of the linker has been reacted with the amatoxin and, the other side with a target-binding moiety. In the context of the present invention, a linker preferably is a $C_{1-20}$-alkyl, $C_{1-20}$-heteroalkyl, $C_{2-20}$-alkenyl, $C_{2-20}$-heteroalkenyl, $C_{2-20}$-alkynyl, $C_{2-20}$-heteroalkynyl, cycloalkyl, heterocycloalkyl, aryl, heteroaryl, aralkyl, or a heteroaralkyl group, optionally substituted. The linker may contain one or more structural elements such as amide, ester, ether, thioether, disulfide, hydrocarbon moieties and the like. The linker may also contain combinations of two or more of these structural elements. Each one of these structural elements may be present in the linker more than once, e.g. twice, three times, four times, five times, or six times. In some embodiments the linker may comprise a disulfide bond. It is understood that the linker has to be attached either in a single step or in two or more subsequent steps to the amatoxin and the target binding moiety. To that end the linker to be will carry two groups, preferably at a proximal and distal end, which can (i) form a covalent bond to a group, preferably an activated group on an amatoxin or the target binding-peptide or (ii) which is or can be activated to form a covalent bond with a group on an amatoxin. Accordingly, if the linker is present, it is preferred that chemical groups are at the distal and proximal end of the linker, which are the result of such a coupling reaction, e.g. an ester, an ether, a urethane, a peptide bond etc. The presence of a "linker" is optional, i.e. the toxin may be directly linked to a residue of the target-binding moiety in some embodiments of the target-binding moiety toxin conjugate of the present invention. It is preferred that the linker is connected directly via a bond to the targeting moiety, preferably at its terminus. If the target-binding moiety comprises free amino, carboxy or sulfhydryl groups, e.g. in the form of Asp, Glu, Arg, Lys, Cys residues, which may be comprised in a polypeptide, then it is preferred that the linker is coupled to such a group.

As used herein, a first compound (e.g. an antibody) is considered to "specifically bind" to a second compound (e.g. an antigen, such as a target protein), if it has a dissociation constant $K_D$ to said second compound of 100 μM or less, preferably 50 μM or less, preferably 30 μM or less, preferably 20 μM or less, preferably 10 μM or less, preferably 5 μM or less, more preferably 1 μM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

As used herein, a "patient" means any mammal or bird who may benefit from a treatment with the target-binding moiety toxin conjugates described herein. Preferably, a "patient" is selected from the group consisting of laboratory animals (e.g. mouse or rat), domestic animals (including e.g. guinea pig, rabbit, chicken, pig, sheep, goat, camel, cow, horse, donkey, cat, or dog), or primates including human beings. It is particularly preferred that the "patient" is a human being.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "administering" includes in vivo administration, as well as administration directly to tissue ex vivo, such as vein grafts.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

"Pharmaceutically acceptable" means approved by a regulatory agency of the Federal or a state government or listed in the U.S. Pharmacopeia or other generally recognized pharmacopeia for use in animals, and more particularly in humans.

Embodiments of the Invention

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first aspect the present invention is directed to a target-binding moiety toxin conjugate comprising: (i) a target-binding moiety; (ii) an amatoxin; and (iii) optionally a linker L2; wherein the amatoxin is connected to the target-binding moiety or, if present, to the linker L2 via the 6' C-atom of amatoxin amino acid 4 (see FIG. 1). In preferred amatoxins usable in the first aspect said amino acid 4 is 2'-sulfur-substituted tryptophan or 2'-sulfur-substituted 6'-hydroxy-tryptophan.

In a preferred embodiment of the first aspect the amatoxin is connected to the target-binding moiety or, if present, to the linker L2 via an oxygen atom bound to the 6' C-atom of amatoxin amino acid 4. It is further preferred that the amatoxin is connected to the target-binding moiety or, if present, to the linker L2 via an ether linkage (i.e. amatoxin-O-L2 or amatoxin-O-target-binding moiety). In these embodiments, it is preferred that amino acid 4 is 6'-hydroxy-tryptophan.

In preferred embodiments of the first aspect the linker L2 is present and the conjugate has the following structure: amatoxin-6'C—O-L2-C(O)—NH-target-binding moiety.

In a second aspect the present invention is directed to a target-binding moiety toxin conjugate comprising: (i) a target-binding moiety; (ii) an amatoxin; and (iii) optionally a linker L3; wherein the amatoxin is connected to the target-binding moiety or, if present, to the linker L3 via the δ C-atom of amatoxin amino acid 3 (see FIG. 1). In preferred amatoxins usable in the second aspect said amino acid 3 is isoleucine, γ-hydroxy-isoleucine or γ,δ-dihydroxy-isoleucine.

In a preferred embodiment of the second aspect the amatoxin is connected to the target-binding moiety or, if present, to the linker L3 via an oxygen atom bound to the δ C-atom of amatoxin amino acid 3. It is further preferred that the amatoxin is connected to the target-binding moiety or, if present, to the linker L3 via an ester linkage preferably in the form of an amatoxin-O—C(O)-L3-target binding moiety or an amatoxin-O—C(O)-target-binding moiety, more preferably an amatoxin-δC—O—C(O)-L3-target-binding moiety or an amatoxin-δC—O—C(O)-target-binding moiety, i.e. an amatoxin-δ$CH_2$—O—C(O)-L3-target-binding moiety or an amatoxin-δ$CH_2$—O—C(O)-target-binding moiety; an ether linkage preferably in the form of an amatoxin-O-L3 or an amatoxin-O-target-binding moiety preferably an amatoxin-δC—O-L3-target binding moiety or an amatoxin-δC—O-target binding moiety, more preferably an amatoxin-δ$CH_2$—O-L3-target binding moiety or an amatoxin-δ$CH_2$—O-target binding moiety; or a urethane linkage preferably in the form of an amatoxin-O—C(O)—NH-L3 or amatoxin-O—C(O)—NH-target-binding moiety, preferably an amatoxin-δC—O—C(O)—NH-L3-target-binding moiety or an amatoxin-δC—O—C(O)—NH-target-binding moiety, i.e. an amatoxin-δ$CH_2$—O—C(O)—NH-L3-target-binding moiety or an amatoxin-δ$CH_2$—O—C(O)—NH-target-binding moiety. In these embodiments, it is preferred that amino acid 3 is γ,δ-dihydroxy-isoleucine.

In preferred embodiments of the second aspect the linker L3 is present and the conjugate has one of the following structures: (i) amatoxin-δC—O—C(O)-L3-C(O)—NH-target-binding moiety; (ii) amatoxin-δC—O-L3-C(O)—NH-target-binding moiety; or (iii) amatoxin-δC—O—C(O)—NH-L3-C(O)—NH-target-binding moiety, i.e. (i) amatoxin-δ$CH_2$—O—C(O)-L3-C(O)—NH-target-binding moiety; (ii) amatoxin-δ$CH_2$—O-L3-C(O)—NH-target-binding moiety; or (iii) amatoxin-δ$CH_2$—O—C(O)—NH-L3-C(O)—NH-target-binding moiety.

In a third aspect the present invention is directed to a target-binding moiety toxin conjugate comprising: (i) a target-binding moiety; (ii) an amatoxin; and (iii) optionally a linker L1; wherein the amatoxin is connected to the target-binding moiety or, if present, to the linker L1 via the γ C-atom of amatoxin amino acid 1 (see FIG. 1). In preferred amatoxins usable in the third aspect said amino acid 1 is asparagine or aspartic acid.

In a preferred embodiment of the third aspect the amatoxin is connected to the target-binding moiety or, if present, to the linker L1 via a nitrogen atom bound to the γ C-atom of amatoxin amino acid 1. It is further preferred that the amatoxin is connected to the target-binding moiety or, if present, to the linker L1 via an amide linkage (i.e. amatoxin-C(O)—NH-L1 or amatoxin-C(O)—NH-target-binding moiety; the C-atom in the aforementioned C(O)-moiety is the γ C-atom of amatoxin amino acid 1). In these embodiments, it is preferred that amino acid 1 is asparagine.

In preferred embodiments of the third aspect the linker L1 is present and the conjugate has the following structure: amatoxin-γC(O)—NH-L1-C(O)—NH-target-binding moiety. In this context it is preferred that the amide on the target-binding moiety side of the conjugate is the product of a reaction with a free amino group that was present in the target-binding moiety.

In preferred embodiments of the first, the second, or the third aspect the target-binding moiety is connected to the amatoxin or, if present, to the linker L1, L2, or L3 via an amino group present in the target-binding moiety.

In preferred embodiments of the first, the second, or the third aspect the amatoxin is selected from α-amanitin, β-amanitin, γ-amanitin, ε-amanitin, amanin, amaninamide, amanullin, or amanullinic acid (all shown in FIG. 1), as well as salts, chemical derivatives, semisynthetic analogs, and synthetic analogs thereof. Particularly preferred amatoxins are α-amanitin, β-amanitin, and amaninamide, as well as salts, chemical derivatives, semisynthetic analogs, and synthetic analogs thereof.

The target binding moiety is in preferred embodiments a protein, in particular an antibody. Proteins and in particular antibodies will comprise several amino acids, which allow the coupling of amatoxins. Preferred amino acids have free amino, hydroxy, or carbonyl-groups, including Lys, Gln, Glu, Asp, Asn, Thr, and Ser. Accordingly, it is possible to couple more than one amatoxin molecules to one protein molecule. An increase of the number of amatoxins per molecule will also increase the toxicity. Accordingly, in a preferred embodiment the ratio of protein to amatoxin is between 1 protein molecule to between 1 and 15 amatoxin molecules, preferably 1, 2, 3, 4, 5, 6, 7, 8, 9, 10, 11, 12, 13, 14, or 15. For the purpose of the calculation of the ratio in case of dimmers like IgGs the dimmer is considered as one molecule. Similar ratios are preferred, if the target binding moiety is not a protein.

In preferred embodiments of the first, the second, or the third aspect the linker L1, L2, or L3 has above indicated meaning and preferred meanings. In further preferred embodiments of the first, the second, or the third aspect the linker L1, L2, or L3 comprises a disulfide bond.

In preferred embodiments of the first, the second, or the third aspect the linker L1, L2, or L3 has a length of 1 to 20 atoms, e.g. 1, 2, 3, 4, 5, 6, 7, 8, 9, 10, 11, 12, 13, 14, 15, 16, 17, 18, 19, or 20 atoms. The length of the linker is defined as the shortest connection—as measured by the number of atoms or bonds—between the toxin moiety and the target-binding moiety.

In preferred embodiments of the first, the second, or the third aspect the target-binding moiety specifically binds to an epitope that is present on a tumour cell. It is particularly preferred that the target-binding moiety specifically binds to an epitope of T-cell- or B-Cell-defined cancer-associated antigen belonging to unique gene products of mutated or recombined cellular genes, in particular cyclin-dependent kinases (e.g. CDC2, CDK2, CDK4), $p15^{Ink4b}$, p53, AFP, β-catenin, caspase 8, p53, Bcr-abl fusion product, MUM-1 MUM-2, MUM-3, ELF2M, HSP70-2M, HST-2, KIAA0205, RAGE, myosin/m, 707-AP, CDC27/m, ETV6/AML, TEL/Amll, Dekcain, LDLR/FUT, Pml-RARa, TEL/AMLI; Cancer-testis (CT) antigens, in particular NY-ESO-1, members of the MAGE-family (MAGE-A1, MAGE-A2, MAGE-A3, MAGE-A4, MAGE-A6, MAGE-10, MAGE-12), BAGE, DAM-6, DAM-10, members of the GAGE-family (GAGE-1, GAGE-2, GAGE-3, GAGE-4, GAGE-5, GAGE-6, GAGE-7B, GAGE-8), NY-ESO-1, NA-88A, CAG-3, RCC-associated antigen G250; Tumour virus antigens, in particular human papilloma virus (HPV)-derived E6 or E7 oncoproteins, Epstein Barr virus EBNA2-6, LMP-1, LMP-2; overexpressed or tissue-specific differentiation antigens, in particular gp77, gp100, MART-1/Melan-A, p53, tyrosinase, tyrosinase-related protein (TRP-1 and TPR-2), PSA, PSM, MC1R; widely expressed antigens, in particular ART4, CAMEL, CEA, CypB, EpCAM, HER2/neu, hTERT, hTRT, ICE, Muc1, Muc2, PRAME RU1, RU2, SART-1, SART-2, SART-3, and WT1; and fragments and derivatives thereof. Particular preferred tumour antigens are antigens derived from the HER-2 and EpCAM proteins.

In preferred embodiments of the first, the second, or the third aspect the target-binding moiety is selected from the group consisting of: (i) antibody or antigen-binding fragment thereof; (ii) antibody-like protein; and (iii) nucleic acid aptamer. In preferred embodiments the antibody or the antigen-binding fragment thereof is selected from a diabody, a tetrabody, a nanobody, a chimeric antibody, a deimmunized antibody, a humanized antibody or a human antibody. In preferred embodiments the antigen binding fragment is selected from the group consisting of Fab, $F(ab')_2$, Fd, Fv, single-chain Fv, and disulfide-linked Fvs (dsFv). In preferred embodiments the antibody or the antigen binding fragment thereof comprises (a) either the membrane-bound form of the heavy chain of huHEA125 (SEQ ID NO: 1) or the soluble form of the heavy chain of huHEA125 (SEQ ID NO: 2); and/or (b) the light chain of huHEA125 (SEQ ID NO: 11).

In preferred embodiments of the first, the second, or the third aspect the target-binding moiety toxin conjugate comprises (i) an antibody or an antigen binding fragment thereof specifically binding to epithelial cell adhesion molecule (EpCAM), wherein the antibody or an antigen binding fragment thereof comprises: (a) the heavy chain of huHEA125, wherein the heavy chain is selected from the group consisting of: (a1) the membrane-bound form of the heavy chain according to SEQ ID NO: 1, wherein the variable domain of the heavy chain VH as shown in SEQ ID NO: 3 comprises between 0 and 10 (e.g. 0, 1, 2, 3, 4, 5, 6, 7, 8, 9, or 10) amino acid exchanges, between 0 and 10 (e.g. 0, 1, 2, 3, 4, 5, 6, 7, 8, 9, or 10) amino acid deletions and/or between 0 and 10 (e.g. 0, 1, 2, 3, 4, 5, 6, 7, 8, 9, or 10) amino acid additions positioned in the framework regions of VH, and wherein the constant domain of the heavy chain as shown in SEQ ID NO: 26 comprises between 0 and 10 (e.g. 0, 1, 2, 3, 4, 5, 6, 7, 8, 9, or 10) amino acid exchanges, between 0 and 10 (e.g. 0, 1, 2, 3, 4, 5, 6, 7, 8, 9, or 10) amino acid deletions and/or between 0 and 10 (e.g. 0, 1, 2, 3, 4, 5, 6, 7, 8, 9, or 10) amino acid additions; and (a2) the soluble form of the heavy chain according to SEQ ID NO: 2, wherein the variable domain of the heavy chain VII as shown in SEQ ID NO: 3 comprises between 0 and 10 (e.g. 0, 1, 2, 3, 4, 5, 6, 7, 8, 9, or 10) amino acid exchanges, between 0 and 10 (e.g. 0, 1, 2, 3, 4, 5, 6, 7, 8, 9, or 10) amino acid deletions and/or between 0 and 10 (e.g. 0, 1, 2, 3, 4, 5, 6, 7, 8, 9, or 10) amino acid additions positioned in the framework regions of VH, and wherein the constant domain of the heavy chain as shown in SEQ ID NO: 27 comprises between 0 and 10 (e.g. 0, 1, 2, 3, 4, 5, 6, 7, 8, 9, or 10) amino acid exchanges, between 0 and 10 (e.g. 0, 1, 2, 3, 4, 5, 6, 7, 8, 9, or 10) amino acid deletions and/or between 0 and 10 (e.g. 0, 1, 2, 3, 4, 5, 6, 7, 8, 9, or 10) amino acid additions; and (b) the light chain of huHEA125 according to SEQ ID NO: 11, wherein the variable domain of the light chain VL as shown in SEQ ID NO: 12 comprises between 0 and 10 (e.g. 0, 1, 2, 3, 4, 5, 6, 7, 8, 9, or 10) amino acid exchanges, between 0 and 10 (e.g. 0, 1, 2, 3, 4, 5, 6, 7, 8, 9, or 10) amino acid deletions and/or between 0 and 10 (e.g. 0, 1, 2, 3, 4, 5, 6, 7, 8, 9, or 10) amino acid additions positioned in the framework regions of VL, and wherein the constant domain of the light chain CL as shown in SEQ ID NO: 28 comprises between 0 and 10 (e.g. 0, 1, 2, 3, 4, 5, 6, 7, 8, 9, or 10) amino acid exchanges, between 0 and 10 (e.g. 0, 1, 2, 3, 4, 5, 6, 7, 8, 9, or 10) amino acid deletions and/or between 0 and 10 (e.g. 0, 1, 2, 3, 4, 5, 6, 7, 8, 9, or 10) amino acid additions; (ii) an amatoxin; and (iii) optionally a linker L1, L2, or L3.

In preferred embodiments of the first, the second, or the third aspect the target-binding moiety toxin conjugate comprises: (a) the heavy chain of huHEA125, wherein the heavy chain is selected from the group consisting of: (a1) the membrane-bound form of the heavy chain according to SEQ ID NO: 1, wherein the variable domain of the heavy chain VH as shown in SEQ ID NO: 3 comprises between 0 and 10 (e.g. 0, 1, 2, 3, 4, 5, 6, 7, 8, 9, or 10) amino acid exchanges, between 0 and 10 (e.g. 0, 1, 2, 3, 4, 5, 6, 7, 8, 9, or 10) amino acid deletions and/or between 0 and 10 (e.g. 0, 1, 2, 3, 4, 5, 6, 7, 8, 9, or 10) amino acid additions positioned in the framework regions of VH; and (a2) the soluble form of the heavy chain according to SEQ ID NO: 2, wherein the variable domain of the heavy chain VH as shown in SEQ ID NO: 3 comprises between 0 and 10 (e.g. 0, 1, 2, 3, 4, 5, 6, 7, 8, 9, or 10) amino acid exchanges, between 0 and 10 (e.g. 0, 1, 2, 3, 4, 5, 6, 7, 8, 9, or 10) amino acid deletions and/or between 0 and 10 (e.g. 0, 1, 2, 3, 4, 5, 6, 7, 8, 9, or 10) amino acid additions positioned in the framework regions of VII; and (b) the light chain of huHEA125 according to SEQ ID NO: 11, wherein the variable domain of the light chain VL as shown in SEQ ID NO: 12 comprises between 0 and 10 (e.g. 0, 1, 2, 3, 4, 5, 6, 7, 8, 9, or 10) amino acid exchanges, between 0 and 10 (e.g. 0, 1, 2, 3, 4, 5, 6, 7, 8, 9, or 10) amino acid deletions and/or between 0 and 10 (e.g. 0, 1, 2, 3, 4, 5, 6, 7, 8, 9, or 10) amino acid additions positioned in the framework regions of VL.

In preferred embodiments of the first, the second, or the third aspect the target-binding moiety toxin conjugate comprises: (a) the heavy chain of huHEA125, wherein the heavy chain is selected from the group consisting of: (a1) the membrane-bound form of the heavy chain according to SEQ ID NO: 1, wherein the variable domain of the heavy chain VH as shown in SEQ ID NO: 3 comprises between 0 and 10 (e.g. 0, 1, 2, 3, 4, 5, 6, 7, 8, 9, or 10) amino acid exchanges, amino acid deletions and/or amino acid additions positioned in the framework regions of VH, and wherein the constant domain of the heavy chain as shown in SEQ ID NO: 26 comprises between 0 and 10 (e.g. 0, 1, 2, 3, 4, 5, 6, 7, 8, 9, or 10) amino acid exchanges, amino acid deletions and/or amino acid additions; and (a2) the soluble form of the heavy chain according to SEQ ID NO: 2, wherein the variable domain of the heavy chain VH as shown in SEQ ID NO: 3 comprises between 0 and 10 (e.g. 0, 1, 2, 3, 4, 5, 6, 7, 8, 9, or 10) amino acid exchanges, amino acid deletions and/or amino acid additions positioned in the framework regions of VH, and wherein the constant domain of the heavy chain as shown in SEQ ID NO: 27 comprises between 0 and 10 (e.g. 0, 1, 2, 3, 4, 5, 6, 7, 8, 9, or 10) amino acid exchanges, amino acid deletions and/or amino acid additions; and (b) the light chain of huHEA125 according to SEQ ID NO: 11, wherein the variable domain of the light chain VL as shown in SEQ ID NO: 12 comprises between 0 and 10 (e.g. 0, 1, 2, 3, 4, 5, 6, 7, 8, 9, or 10) amino acid exchanges, amino acid deletions and/or amino acid additions positioned in the framework regions of VL, and wherein the constant domain of the light chain CL as shown in SEQ ID NO: 28 comprises between 0 and 10 (e.g. 0, 1, 2, 3, 4, 5, 6, 7, 8, 9, or 10) amino acid exchanges, amino acid deletions and/or amino acid additions.

In preferred embodiments of the first, the second, or the third aspect the target-binding moiety toxin conjugate comprises: (a) the heavy chain of huHEA125, wherein the heavy chain is selected from the group consisting of: (a1) the membrane-bound form of the heavy chain according to SEQ ID NO: 1, wherein the variable domain of the heavy chain VH as shown in SEQ ID NO: 3 comprises between 0 and 10 (e.g. 0, 1, 2, 3, 4, 5, 6, 7, 8, 9, or 10) amino acid exchanges positioned in the framework regions of VH, and wherein the constant domain of the heavy chain as shown in SEQ ID NO: 26 comprises between 0 and 10 (e.g. 0, 1, 2, 3, 4, 5, 6, 7, 8, 9, or 10) amino acid exchanges; and (a2) the soluble form of the heavy chain according to SEQ ID NO: 2, wherein the variable domain of the heavy chain VH as shown in SEQ ID NO: 3 comprises between 0 and 10 (e.g. 0, 1, 2, 3, 4, 5, 6, 7, 8, 9, or 10) amino acid exchanges positioned in the framework regions of VH, and wherein the constant domain of the heavy chain as shown in SEQ ID NO: 27 comprises between 0 and 10 (e.g. 0, 1, 2, 3, 4, 5, 6, 7, 8, 9, or 10) amino acid exchanges; and (b) the light chain of huHEA125 according to SEQ ID NO: 11, wherein the variable domain of the light chain VL as shown in SEQ ID NO: 12 comprises between 0 and 10 (e.g. 0, 1, 2, 3, 4, 5, 6, 7, 8, 9, or 10) amino acid exchanges positioned in the framework regions of VL, and wherein the constant domain of the light chain CL as shown in SEQ ID NO: 28 comprises between 0 and 10 (e.g. 0, 1, 2, 3, 4, 5, 6, 7, 8, 9, or 10) amino acid exchanges.

Within further preferred embodiments of the first, the second, or the third aspect the target-binding moiety comprises the heavy chain of huHEA125 (membrane-bound form, SEQ ID NO: 1) and/or the light chain of huHEA125 (SEQ ID NO: 11). In one embodiment of the first, the second, or the third aspect, the heavy chain of huHEA125 and/or the light chain of huHEA125 each comprise independently from each other up to 20 (e.g. 1, 2, 3, 4, 5, 6, 7, 8, 9, 10, 11, 12, 13, 14, 15, 16, 17, 18, 19 or 20) amino acid exchanges, deletions, or additions, wherein these amino acid exchanges, deletions, or additions may be positioned in the constant domains of the heavy chain and/or in the constant domain of the light chain and/or in the framework regions of the variable domain of the heavy chain and/or in the framework regions of the variable domain of the light chain. In a particularly preferred embodiment of the first, the second, or the third aspect, the antibody is a complete IgG antibody comprising two heavy chains of huHEA125 (SEQ ID NO: 1)

and two light chains of huHEA125 (SEQ ID NO: 11), wherein one heavy chain is connected to one light chain via a disulfide linkage and wherein the heavy chains are connected to each other by one or two (preferably two) disulfide linkages.

Within further preferred embodiments of the first, the second, or the third aspect the target-binding moiety comprises the heavy chain of huHEA125 (soluble form, SEQ ID NO: 2) and/or the light chain of huHEA125 (SEQ ID NO: 11). In one embodiment of the first, the second, or the third aspect, the heavy chain of huHEA125 and/or the light chain of huHEA125 each comprise independently from each other up to 20 (e.g. 1, 2, 3, 4, 5, 6, 7, 8, 9, 10, 11, 12, 13, 14, 15, 16, 17, 18, 19 or 20) amino acid exchanges, deletions, or additions, wherein these amino acid exchanges, deletions, or additions may be positioned in the constant domains of the heavy chain and/or in the constant domain of the light chain and/or in the framework regions of the variable domain of the heavy chain and/or in the framework regions of the variable domain of the light chain. In a particularly preferred embodiment of the first, the second, or the third aspect, the antibody is a complete IgG antibody comprising two heavy chains of huHEA125 (SEQ ID NO: 2) and two light chains of huHEA125 (SEQ ID NO: 11), wherein one heavy chain is connected to one light chain via a disulfide linkage and wherein the heavy chains are connected to each other by one or two (preferably two) disulfide linkages.

In a fourth aspect the present invention is directed to the target-binding moiety toxin conjugate according to the first, the second, or the third aspect for use in medicine.

In a fifth aspect the present invention is directed to the target-binding moiety toxin conjugate according to the first, the second, the third or the fourth aspect for the treatment of cancer or an autoimmune disease in a patient, wherein the cancer is preferably selected from the group consisting of pancreatic cancer, cholangiocarcinoma, breast cancer, colorectal cancer, lung cancer, prostate cancer, ovarian cancer, stomach cancer, kidney cancer, head and neck cancer, brain tumors, childhood neoplasms, soft tissue sarcomas, epithelial skin cancer, malignant melanoma, leukemia, and malignant lymphoma and wherein the autoimmune disease is preferably selected from the group consisting of Ankylosing Spondylitis, Chagas disease, Crohns Disease, Dermatomyositis, Diabetes mellitus type 1, Goodpasture's syndrome, Graves' disease, Guillain-Barré syndrome (GBS), Hashimoto's disease, Hidradenitis suppurativa, Idiopathic thrombocytopenic purpura, Lupus erythematosus, Mixed Connective Tissue Disease, Myasthenia gravis, Narcolepsy, Pemphigus vulgaris, Pernicious anaemia, Psoriasis, Psoriatic Arthritis, Polymyositis, Primary biliary cirrhosis, Relapsing polychondritis, Rheumatoid arthritis, Schizophrenia, Sjögren's syndrome, Temporal arteritis, Ulcerative Colitis, and Vasculitis Wegener's granulomatosis, in particular Rheumatoid arthritis.

In a sixth aspect the present invention is directed to a pharmaceutical composition comprising at least one type of the target-binding moiety toxin conjugate according to the first, the second, or the third aspect and further comprising one or more pharmaceutically acceptable diluents, carriers, excipients, fillers, binders, lubricants, glidants, disintegrants, adsorbents; and/or preservatives. It is envisioned that the pharmaceutical composition may comprise two or more different target-binding moiety toxin conjugates. Preferably the target binding moieties bind to different targets. In particular in tumour therapy it has be recognized that it may be advantageous to administer two or more target-binding moieties directed against two different targets on the same tumour cell thereby increasing the likelihood that all tumour cells are killed by the administration of the therapeutic and decreasing the likelihood of development of resistance.

It is particularly preferred that the pharmaceutical composition of the seventh aspect or as prepared in the sixth aspect can be used in the form of systemically administered medicaments. These include parenterals, which comprise among others injectables and infusions. Injectables are formulated either in the form of ampoules or as so called ready-for-use injectables, e.g. ready-to-use syringes or single-use syringes and aside from this in puncturable flasks for multiple withdrawal. The administration of injectables can be in the form of subcutaneous (s.c.), intramuscular (i.m.), intravenous (i.v.) or intracutaneous (i.c.) application. In particular, it is possible to produce the respectively suitable injection formulations as a suspension of crystals, solutions, nanoparticular or a colloid dispersed systems like, e.g. hydrosols.

Injectable formulations can further be produced as concentrates, which can be dissolved or dispersed with aqueous isotonic diluents. The infusion can also be prepared in form of isotonic solutions, fatty emulsions, liposomal formulations and micro-emulsions. Similar to injectables, infusion formulations can also be prepared in the form of concentrates for dilution. Injectable formulations can also be applied in the form of permanent infusions both in in-patient and ambulant therapy, e.g. by way of mini-pumps.

It is possible to add to parenteral drug formulations, for example, albumin, plasma, expander, surface-active substances, organic diluents, pH-influencing substances, complexing substances or polymeric substances, in particular as substances to influence the adsorption of the target-binding moiety toxin conjugates of the invention to proteins or polymers or they can also be added with the aim to reduce the adsorption of the target-binding moiety toxin conjugates of the invention to materials like injection instruments or packaging-materials, for example, plastic or glass.

The target-binding moiety toxin conjugates of the invention can be bound to microcarriers or nanoparticles in parenterals like, for example, to finely dispersed particles based on poly(meth)acrylates, polylactates, polyglycolates, polyamino acids or polyether urethanes. Parenteral formulations can also be modified as depot preparations, e.g. based on the "multiple unit principle", if the target-binding moiety toxin conjugates of the invention are introduced in finely dispersed, dispersed and suspended form, respectively, or as a suspension of crystals in the medicament or based on the "single unit principle" if the target-binding moiety toxin conjugate of the invention is enclosed in a formulation, e.g. in a tablet or a rod which is subsequently implanted. These implants or depot medicaments in single unit and multiple unit formulations often consist of so called biodegradable polymers like e.g. polyesters of lactic acid and glycolic acid, polyether urethanes, polyamino acids, poly(meth)acrylates or polysaccharides.

Adjuvants and carriers added during the production of the pharmaceutical compositions of the present invention formulated as parenterals are preferably aqua sterilisata (sterilized water), pH value influencing substances like, e.g. organic or inorganic acids or bases as well as salts thereof, buffering substances for adjusting pH values, substances for isotonization like e.g. sodium chloride, sodium hydrogen carbonate, glucose and fructose, tensides and surfactants, respectively, and emulsifiers like, e.g. partial esters of fatty acids of polyoxyethylene sorbitans (for example, Tween®) or, e.g. fatty acid esters of polyoxyethylenes (for example, Cremophor®), fatty oils like, e.g. peanut oil, soybean oil or castor oil, synthetic esters of fatty acids like, e.g. ethyl oleate, isopropyl myristate and neutral oil (for example, Miglyol®) as well as polymeric adjuvants like, e.g. gelatine, dextran, polyvinylpyrrolidone, additives which increase the solubility of organic solvents like, e.g. propylene glycol, ethanol, N,N-dimethylacetamide, propylene glycol or complex forming substances like, e.g. citrate and urea, preservatives like, e.g. benzoic acid hydroxypropyl ester and methyl ester, benzyl alcohol, antioxidants like e.g. sodium sulfite and stabilizers like e.g. EDTA.

When formulating the pharmaceutical compositions of the present invention as suspensions in a preferred embodiment thickening agents to prevent the setting of the target-binding moiety toxin conjugates of the invention or, tensides and polyelectrolytes to assure the resuspendability of sediments and/or complex forming agents like, for example, EDTA are added. It is also possible to achieve complexes of the active ingredient with various polymers. Examples of such polymers are polyethylene glycol, polystyrol, carboxymethyl cellulose, Pluronics® or polyethylene glycol sorbit fatty acid ester. The target-binding moiety toxin conjugates of the invention can also be incorporated in liquid formulations in the form of inclusion compounds e.g. with cyclodextrins. In particular embodiments dispersing agents can be added as further adjuvants. For the production of lyophilisates scaffolding agents like mannite, dextran, saccharose, human albumin, lactose, PVP or varieties of gelatine can be used.

In a further aspect the present invention is directed to a method of treating cancer, or an autoimmune disease, wherein the cancer is preferably selected from pancreatic cancer, cholangiocarcinoma, breast cancer, colorectal cancer, lung cancer, prostate cancer, ovarian cancer, stomach cancer, kidney cancer, head and neck cancer, brain tumors, childhood neoplasms, soft tissue sarcomas, epithelial skin cancer, malignant melanoma, leukemia, or malignant lymphoma and wherein the autoimmune disease is preferably selected from the group consisting of Ankylosing Spondylitis, Chagas disease, Crohns Disease, Dermatomyositis, Diabetes mellitus type 1, Goodpasture's syndrome, Graves' disease, Guillain-Barré syndrome (GBS), Hashimoto's disease, Hidradenitis suppurativa, Idiopathic thrombocytopenic purpura, Lupus erythematosus, Mixed Connective Tissue Disease, Myasthenia gravis, Narcolepsy, Pemphigus vulgaris, Pernicious anaemia, Psoriasis, Psoriatic Arthritis, Polymyositis, Primary biliary cirrhosis, Relapsing polychondritis, Rheumatoid arthritis, Schizophrenia, Sjögren's syndrome, Temporal arteritis, Ulcerative Colitis, and Vasculitis Wegener's granulomatosis, in a patient in need thereof, comprising administering to the patient an effective amount of a target-binding moiety toxin conjugate as defined in the first, the second, or the third aspect.

EXAMPLES

In the following, the invention is explained in more detail by non-limiting examples:

Example 1

Materials and Methods 1.1 Chimeric Antibody huHEA125

Several years ago, the inventors have established a hybridoma cell line secreting the anti-EpCAM mouse monoclonal antibody HEA125 (Moldenhauer et al., 1987; Momburg et al., 1987). Using molecular biology techniques this hybridoma line was reconstructed to produce a chimeric version of the antibody consisting of the mouse variable domains hooked up to human kappa constant light chain and human IgG1 constant heavy chain. The resulting antibody huHEA125 binds to EpCAM-expressing cells with high affinity ($K_d$=2.2×$10^{-9}$ M) and high specificity. The gene sequences and the amino acid sequences of huHEA125 immunoglobulin are shown below:

huHEA125 Heavy Chain

Peptide sequence heavy chain, membrane bound form (IGHV/IGHD/IGHJ/IGHG1; IGHG1 is underlined) (SEQ ID NO: 1):

```
EVKLLESGGGLVQPGGSLKLSCAASGFDFSRFWMTWVRQAPGKGLEWIGE
INLDSSTINYTPSLKDKFIISRDNAKNTLFLQMSKVRSEDTALYYCSRGI
SMDYWGQGTSVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGLQLDET
CAEAQDGELDGLWTTITIFISLFLLSVCYSAAVTLFKVKWIFSSVVELKQ
TLVPEYKNMIGQAP
```

Peptide sequence heavy chain, secreted form (SEQ ID NO: 2):

```
EVKLLESGGGLVQPGGSLKLSCAASGFDFSRFWMTWVRQAPGKGLEWIGE
INLDSSTINYTPSLKDKFIISRDNAKNTLFLQMSKVRSEDTALYYCSRGI
SMDYWGQGTSVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK
```

Peptide sequence (IGHV/IGHD/IGHJ=VH domain; the framework regions FR1, FR2, FR3 and FR4 are underlined) (SEQ ID NO: 3):

```
EVKLLESGGGLVQPGGSLKLSCAASGFDFSRFWMTWVRQAPGKGLEWIGE
INLDSSTINYTPSLKDKFIISRDNAKNTLFLQMSKVRSEDTALYYCSRGI
SMDYWGQGTSVTVSS
```

Nucleic acid sequence (annotated according to the IMGT-nomenclature, IGHV/IGHD/IGHJ; IGHD underlined; IGHJ doubly underlined):

FR1 (SEQ ID NO: 4):
GAAGTGAAGCTTCTCGAGTCTGGAGGTGGCCTGGTGCAGCCTGGAGGATC

CCTGAAACTCTCCTGTGCAGCCTCA

CDR1 (SEQ ID NO: 5):
GGATTCGATTTTAGTAGATTCTGG

FR2 (SEQ ID NO: 6):
ATGACTTGGGTCCGGCAGGCTCCAGGGAAAGGGCTAGAATGGATTGGAGA

A

CDR2 (SEQ ID NO: 7):
ATTAATCTAGATAGCAGTACGATA

FR3 (SEQ ID NO: 8):
AACTATACGCCATCTCTAAAGGATAAATTCATCATCTCCAGGGACAACGC

CAAAAATACGCTGTTCCTGCAAATGAGCAAAGTGAGATCTGAGGACACAG

CCCTTTATTACTGT

CDR3 (SEQ ID NO: 9):
TCAAGAGGTATTTCTATGGACTAC

FR4 (SEQ ID NO: 10):
TGGGGTCAGGGAACCTCAGTCACCGTCTCCTCA huHEA125 Light Chain

Peptide sequence light chain (IGKV/IGKJ/IGKC; IGKC is underlined) (SEQ ID NO: 11):

DILLTQSPAILSVSPGERVSFSCRASQSIGISLHWYQQRPSDSPRLLIKY

ASESISGIPSRFSGSGSGTDFTLSINSVESEDIADYYCQQSNIWPTTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Peptide sequence (IGKV/IGKJ=VL domain; the framework regions FR1, FR2, FR3 and FR4 are underlined) (SEQ ID NO: 12):

DILLTQSPAILSVSPGERVSFSCRASQSIGISLHWYQQRPSDSPRLLIKY

ASESISGIPSRFSGSGSGTDFTLSINSVESEDIADYYCQQSNIWPTTFGA

GTKLELK

Nucleic acid sequence (annotated according to the IMGT-nomenclature, IGKV/IGKJ; IGKV is underlined; IGKJ is doubly underlined):

FR1 (SEQ ID NO: 13):
GACATCTTGCTGACTCAGTCTCCAGCCATCCTGTCTGTGAGTCCAGGAGA

AAGAGTCAGTTTCTCCTGCAGGGCCAGT

CDR1 (SEQ ID NO: 14):
CAGAGCATTGGCATAAGT

FR2 (SEQ ID NO: 15):
TTACACTGGTATCAGCAAAGACCAAGTGATTCTCCAAGGCTTCTCATAAA

G

CDR2 (SEQ ID NO: 16):
TATGCTTCT

-continued

FR3 (SEQ ID NO: 17):
GAGTCAATCTCTGGGATCCCTTCCAGGTTTAGTGGCAGTGGATCAGGGAC

AGATTTTACTCTTAGCATCAACAGTGTGGAGTCTGAAGATATTGCAGATT

ATTACTGT

CDR3 (SEQ ID NO: 18:
CAACAAAGTAATATCTGGCCAACCACG

FR4 (SEQ ID NO: 19):
TTCGGTGCTGGGACCAAGCTGGAGCTGAAA 1.2 Control Antibody Xolair®

The control antibody Xolair® (Omalizumab, human IgG1 antibody directed against human IgE immunoglobulin) was produced by Novartis, Germany.

1.3 Carcinoma Cell Lines

The following carcinoma cell lines were used for growth inhibition studies with huHEA125-amatoxin conjugates:

| | |
|---|---|
| Capan-1 | pancreatic adenocarcinoma |
| MCF-7 | human breast adenocarcinoma (derived from pleural effusion) |
| Colo205 | colon cancer metastasis |
| OZ | cholangiocarcinoma |

The following carcinoma cell lines were used for growth inhibition studies or mouse xenograft studies with HERCEPTIN-amatoxin conjugates:

| | |
|---|---|
| SKOV-3 | ovarian carcinoma |
| SK-BR-3 | breast adenocarcinoma |
| NCI-N87 | gastric carcinoma |
| MDA-MB231 | breast carcinoma |

Cells were obtained from the American Type Culture Collection (Manassas, USA).

1.4 Synthesis of Amanitin Derivatives with Linker at Amino Acid 1

1.4.1 Synthesis of Di-t-Butyloxycarbonyl-Hexamethylene-diamine

Thirty g of t-butyloxycarbonylazide was dissolved in 50 ml of 1.4-dioxan and added dropwise to 12 g of hexamethylenediamine dissolved in 60 ml of 1,4-dioxane at 0° C. After 20 h at RT diethylether was added and the precipitate isolated in a Büchner funnel. Recrystallized from methanol/water.

1.4.2 Synthesis of t-Butyloxycarbonyl-hexamethylenediamine hydrochloride 12.9 g of di-t-butyloxycarbonyl-hexamethylenediamine was suspended in 100 ml of diethylether containing HCl (2N) and stirred magnetically for 3 h at RT. The precipitate formed was isolated and thoroughly washed with diethylether yielding a first fraction of the product. Addition of another 100 ml of diethylether containing HCl (2N) yields another fraction of the product, which is pure after several washings with diethylether. Yield ca. 3 g.

1.4.3 Synthesis of β-Amanitin-(t-butyloxy-carbonyl)-hexamethylenediamide (I)

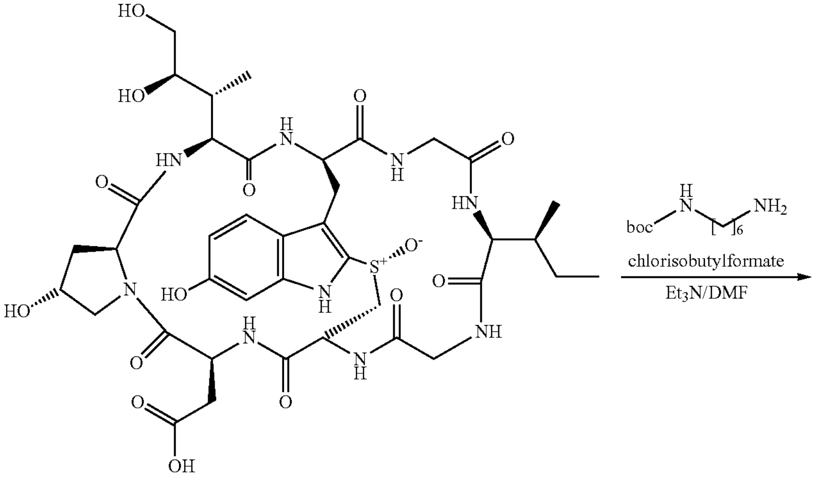

β-amanitin

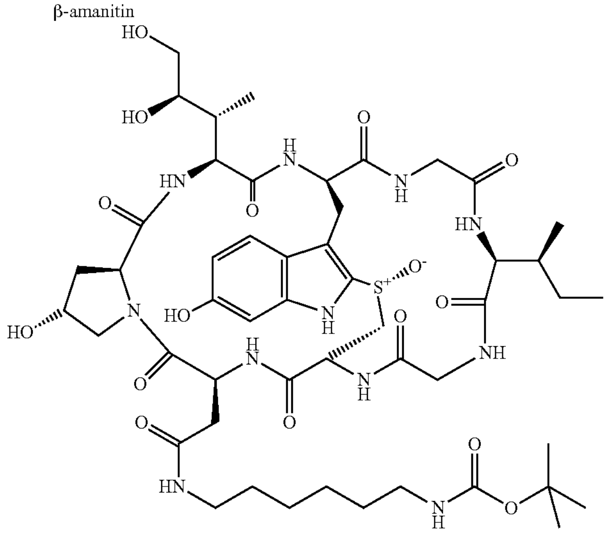

(I)

20 mg of dried β-amanitin (22 μmol) was dissolved in 0.3 ml of dried dimethylformamide (DMF), and 0.005 ml of triethylamine was added. Under magnetic stirring, the reaction mixture was cooled to −18° C. (ice/NaCl) and after 10 min 0.164 ml of a mixture of 0.1 ml of chloroisobutylformate and 1.0 ml of DMF (110 μmol, 5 eq.) was added. The reaction was allowed to proceed for 20 min at −18° C. Fifty-five mg (220 μmol, 10 eq.) of t-butyloxy-carbonyl-hexamethylenediamine hydrochloride and 0.005 ml of triethylamine were dissolved in 0.3 ml of DMF, added to the reaction and stirred for 1 h at RT.

The reaction mixture was applied to 4 tlc silica plates (20×20 cm) and developed in chloroform/methanol/water (65:25:5). The product was identified in the u.v. light ($R_F$=0.49), scraped off and extracted with methanol. Yield 11.5 mg. Recovery of β-amanitin by the same procedure was 7.5 mg.

1.4.4 Synthesis of β-Amanitin-hexamethylenediamide (II)

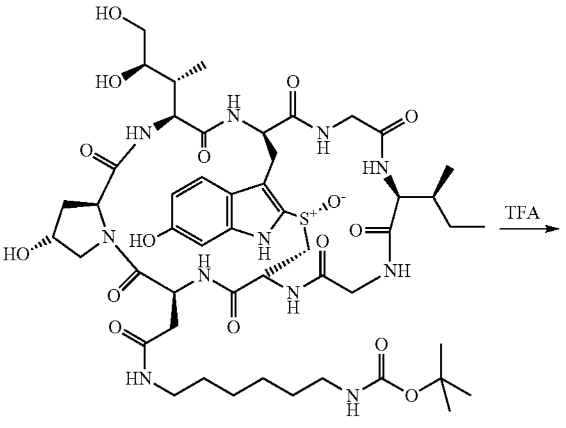

(I)

-continued

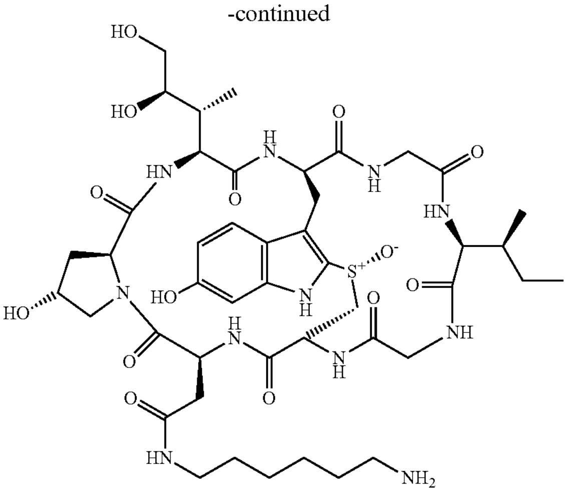

(II)

4.54 mg (4.05 μmol) β-Amanitin-(t-butyloxy-carbonyl)-hexamethylenediamide (I) was stirred at room temperature in 250 μl trifluoroacetic acid. After 2 minutes the excess TFA was evaporated at 20° C. and the remaining solid coevaporated 2 times with 1 ml acetonitrile and methanol. The crude amine was dissolved in 1000 μl dmso and prified on a LaPrep-HPLC: column: Kromasil 100-C18, 10 μm, 250×20 mm, with methanol/water (0.05% TFA), flow: 26 ml/min, detection at λ=295 nm. Solvent A: 95% water: 5% methanol 0.05% trifluoroacetic acid. Solvent B: 10% water: 90% methanol 0.05% trifluoroacetic acid. Gradient: 0-5 min 100% A; 5-20 25 min 0% A; 25-27 min 100% A; 27-35 min 100% A. The fractions with the same retention time were collected and the solvents evaporated.

4.0 mg (70% yield) of a white foam. MS: 1019 M+H;

1.4.5 Synthesis of β-Amanitin-hexamethylenediamido-suberoyl-HERCEPTIN and β-Amanitin-hexamethylenediamido-dithio[bis-propionate]-HERCEPTIN 1.33 mg of β-amanitin-hexamethylendiamide (II) was dissolved in 144 μl molecular sieve dried DMF. 16.0 μl solution of DSS (disuccinimidyl suberate; 3.7 mg DSS/100 μl DMF) or 16.0 μl solution of DSP (dithiobis(succinimidyl) propionate; 3.4 mg DSP/100 μl DMF) and 3.7 μl triethylamine have been added respectively. Reaction was performed over night at RT. Reaction products have been precipitated by 2×30 ml dried diethylether and resolubilized in 133 μl dried DMF. 133 μl of each DMF solution was added to 2.25 ml HERCEPTIN solution (2 mg/ml in PBS). Reaction was performed over night at RT on a rotating shaker. Isolation of the antibody-conjugates β-amanitin-hexamethylenediamido-suberoyl-HERCEPTIN and β-amanitin-hexamethylenediamido-suberoyl-HERCEPTIN was performed by separation of macromolecular components on a G25-gel filtration column.

1.4.6 Synthesis of β-Amanitin-hexamethylenediamido-suberoyl-Xolair

The β-amanitin conjugate with the control antibody Xolair (2 mg/ml) was prepared according to the huHEA125 conjugate. Ratio toxin:IgG was ca 1:1.

1.4.7 Synthesis of β-Amanitin-hexamethylenediamido-suberoyl-huHEA125

10 mg of (I) (9.0 μmol) were treated with 0.2 ml of trifluoroacetic acid for 2 min at RT. The acid was removed in vacuo, and the residue dissolved in 0.2 ml of DMF. After the addition of 0.010 ml of triethylamine, 9.0 mg of disuccinimidylsuberate (DSS) (27 μmol) in 0.1 ml of DMF was added and reacted for 2.5 h at RT. The reaction product was precipitated with dietylether, centrifuged, and the pellet dissolved in 0.2 ml of DMF. Half of this solution was added to 8 mg of huHEA125 in 4 ml of PBS. The mixture was rotated slowly for 16 h at 5° C., and the toxin-antibody conjugate was separated from unreacted amanitin and N-hydroxy-succinimide on a Sephadex G25 column (100×2 cm) developed with PBS.

1.4.8 Synthesis of β-Amanitin-N-hydroxysuccinimide ester (I)

10 mg of dried β-amanitin (11 μmol) was dissolved in 0.1 ml of dry dimethylformamide (DMF). To this solution 8 mg of N-hydroxysuccinimide (70 μmol) in 0.02 ml of DMF was added, followed by 4 mg of dicyclohexylcarbodiimide (20 μmol) in 0.02 ml of DMF. The mixture was allowed to react for 16 h at RT, and the solution separated from crystallized dicyclohexylurea. β-Amanitin-N-hydroxysuccinimide ester was precipitated by the addition of 10 ml of diethylether, and the precipitate isolated by centrifugation. The pellet was macerated with another 10 ml of ether and centrifuged again. Purification was not necessary, because the following step allowed separation and recovery of unreacted β-amanitin.

1.4.9 Synthesis of β-Amanitin-huHEA125 (huHEA125-Amanitin1)

The precipitate of (I) was dissolved in 0.2 ml of DMF, added to 4 ml of huHEA125 (2 mg/ml) in PBS and rotated slowly over night at 5° C. Applied to a Sephadex G25 column (100×2 cm) developed with PBS, the reaction product was separated from unreacted β-amanitin and N-hydroxysuccinimide. The toxin load was ca. 1 amanitin per IgG molecule.

1.5 Synthesis of Amanitin huHEA Conjugate with Linker at Amino Acid 4

1.5.1 Synthesis of α-Amanitin-6'-(t-butyl-acetate) (I)

Twenty mg of α-amanitin (22 μmol) was dissolved in 0.4 ml of dry dimethylformamide (DMF), and 1.5 eq. (33 μmol) of 0.5M sodium ethylate were added under magnetic stirring. Immediately, 18 μl (5.5 eq., 120 μmol, 23.4 mg, d=1.3) of t-butyl bromoacetate (mwt. 195) was added and allowed to react for 10 min. The reaction mixture was applied to 2 silica tlc plates (20 cm×20 cm, Merck HF254) and developed in chloroform/methanol/water (65:25:4). The product ($R_F$=0.41) was detected in u.v. light, scraped off and eluted with methanol. Yield: 55%.

1.5.2 Synthesis of α-Amanitin-6'-acetyl-(t-butyloxycarbonyl)-ethylene diamide (II)

Five mg (5 μmol) of (I) were reacted with 0.2 ml of trifluoroacetic acid for 2 min, and the acid was removed in vacuo. The residue was dissolved in 0.2 ml DMF, and 0.005 ml of triethylamine was added. Under magnetic stirring, the solution was brought to −18° C. (ice/NaCl) and 3.4 mg (25 μmol, 5 eq.) of isobutylchloroformate was added. The reaction was allowed to proceed at −18° C. for 20 min., and 9.8 mg (50 mol, 10 eq.) of t-butyloxycarbonyl-ethylenediamine hydrochloride dissolved in 0.1 ml DMF and 0.006 ml triethylamine were added. The reaction mixture was stirred for 1 h at RT. The product was precipitated with dry diethylether, and the residue developed on a silica tlc plate as described above. ($R_F$=0.28). Yield: 85%.

1.5.3 Synthesis of α-Amanitin-6'-acetylethylene-diamido-suberoyl-huHEA125 (huHEA125-Amanitin4)

Four mg (3.6 μmol) of (II) was dissolved in 0.2 ml of trifluoroacetic acid for 2 min and evaporated in vacuo. The residue was dissolved in 0.2 ml of dry DMF, 0.005 ml of triethylamine added, and reacted with 3 mg (8.2 μmol, 2.3 eq.) of disuccinimidyl suberate (DSS) under magnetic stirring for 2.5 h at RT. The amanitin derivative was precipitated with dry diethylether, centrifuged, macerated with ether again, and centrifuged. Dissolved in 0.15 ml of DMF it was added to 5 ml of huHEA125 (2 mg/ml) in PBS and rotated slowly over night at 5° C. Developed on a Sephadex G25 column (100×2 cm) with PBS the antibody amanitin conjugate was separated from unreacted amanitin derivative and by-products. The ratio toxin:antibody was 3.0.

1.6 Synthesis of Amanitin Herceptin Conjugates with Linker at Amino Acid 4

1.6.1 Synthesis of 6'O—(NH-boc-6-aminohexyl)-α-amanitin (1)

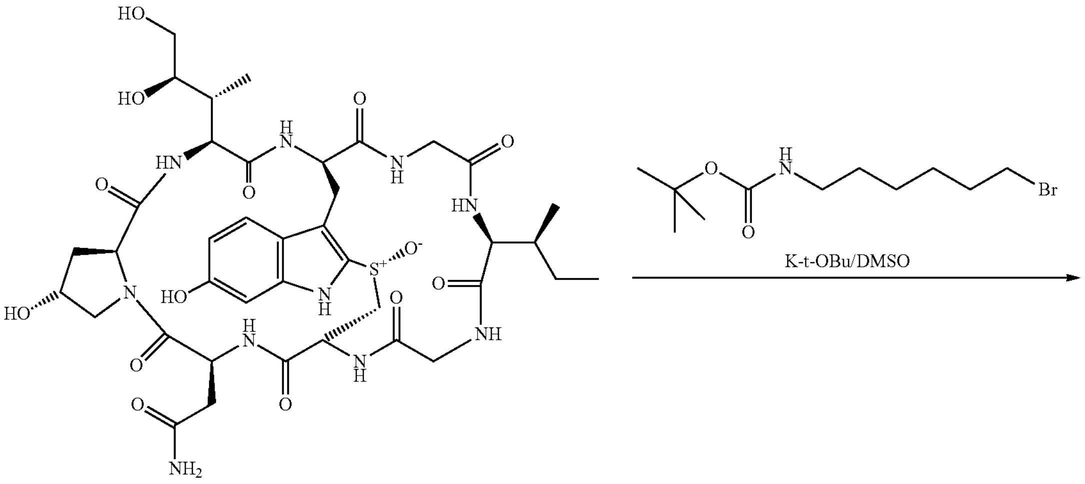

α-amanitin

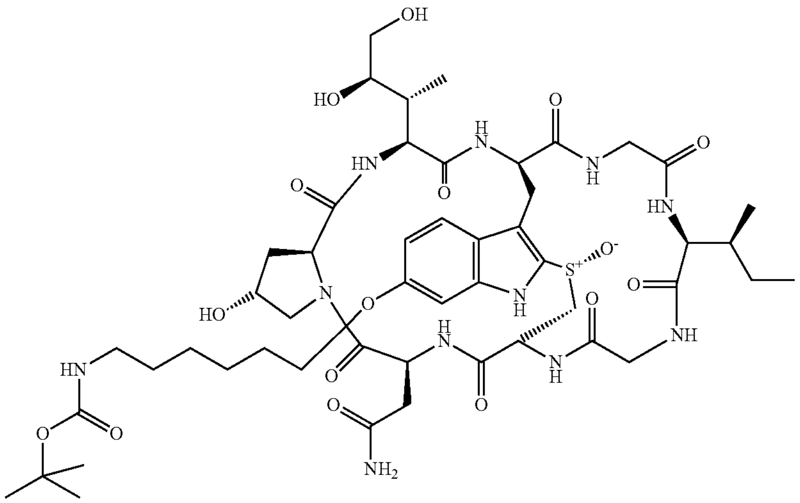

(1)

Under argon 30.00 mg (32.6 μmol) of vacuum dried α-amanitin was dissolved in 1000 μl dry dimethyl sulfoxide (DMSO). 73.18 mg (261.2 μl, 6 eq.) NH-boc-aminohexyl-bromide (Fluka 89171) and 3.66 mg (32.6 μmol) potassium tert-butylate was added. After 90 minutes at room temperature the reaction mixture was acidified to pH=4 with acetic acid and diluted with 40 ml diethylether. The solid was collected and taken up in 1000 ti methanol. The methanol solution was diluted with 10000 water. The solution was purified on a LaPrep-HPLC: column: Kromasil 100-C18, 10 μm, 250x20 mm, with methanol/water (0.05% TFA), flow: 26 ml/min, detection at λ=295 nm. Solvent A: 95% water: 5% methanol 0.05% trifluoroacetic acid. Solvent B: 10% water: 90% methanol 0.05% trifluoroacetic acid. Gradient: 0-5 min 100% A; 5-20 min 0% A; 20-25 min 0% A; 25-27 min 100% A; 27-30 min 100% A. The fractions with the same retention time were collected and the solvents evaporated.

9.9 mg (27% yield) of a white powder. MS: 1118 M+H; 1140 $M+Na^+$ 1.6.2 Synthesis of 6'-O-(-6-aminohexyl)-α-amanitin (2)

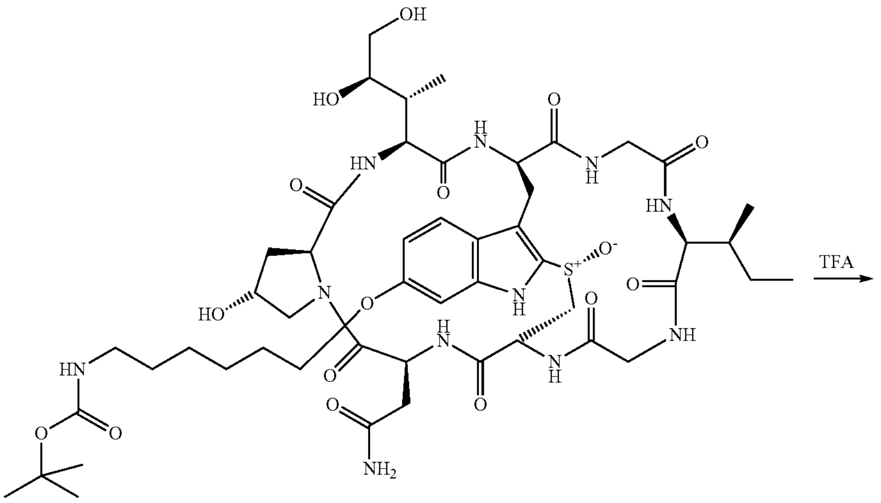

(1)

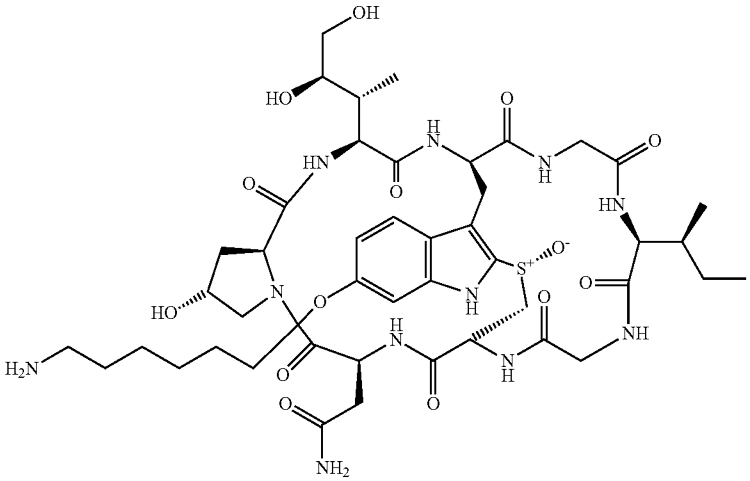

(2)

9.90 mg (8.85 μmol) 6'-(—NH-boc-6-aminohexyl-)-α-amanitin (compound (1)) was dissolved in 250 μl trifluoroacetic acid. The reaction mixture was stirred under argon at ambient temperature. After 2 minutes the acid was removed in vacuum at 20° C. and the residue dried. The crude α-amanitin ether was purified on a LaPrep-HPLC: column: Kromasil 100-C18, 10 μm, 250×20 mm, with methanol/water (0.05% TFA), flow: 26 ml/min, detection at λ=295 nm. Solvent A: 95% water: 5% methanol 0.05% trifluoroacetic acid. Solvent B: 10% water: 90% methanol 0.05% trifluoroacetic acid. Gradient: 0-5 min 100% A; 5-25 min 50% A; 25-30 min 0% A; 30-35 min 0% A; 35-40 min 100% A, 40-45 min 100% A. The fractions with the same retention time were collected and the solvents evaporated.

9.10 mg (99% yield) of a white powder. MS: 1019 M+H+; 1041 M+Na+

1.6.3 Synthesis of α-amanitin-Herceptin conjugates (3) and (4)

2.0 mg of compound (2) was dissolved in 113 μl molecular sieve dried DMF. 21.8 μl solution of DSS (disuccinimidyl suberate; 3.7 mg DSS/100 μl DMF) or 23.9 μl solution of DSP (dithiobis(succinimidyl) propionate; 3.7 mg DSP/100 μl DMF) and 5.7 μl triethylamine have been added respectively. Reaction was performed over night at RT. Reaction products have been precipitated by 2×30 ml dried diethylether and resolubilized in 200 μl dried DMF. 59 μl (DSS) or 173 μl (DSP) of the DMF solutions were added to 6.0 ml antibody solution (2 mg/ml in PBS). Reaction was performed over night at RT on a rotating shaker. Isolation of the antibody-conjugates (3) and (4) was performed by separation of macromolecular components on a G25-gel filtration column.

(3)
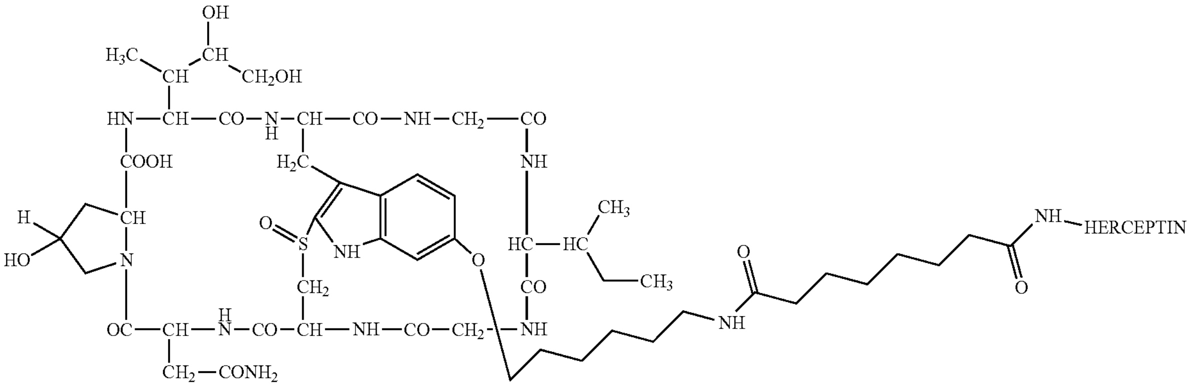
(4)
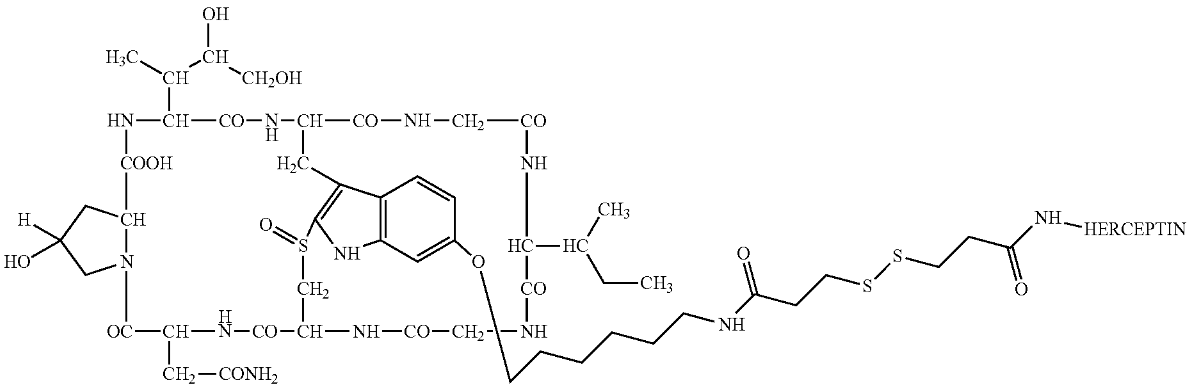
1.7 Synthesis of Amanitin Herceptin Conjugates with Linker at Amino Acid 4
1.7.1 Synthesis of 6'-O-(5-O-t-butyl-carboxypentyl)-α-amanitin (5)
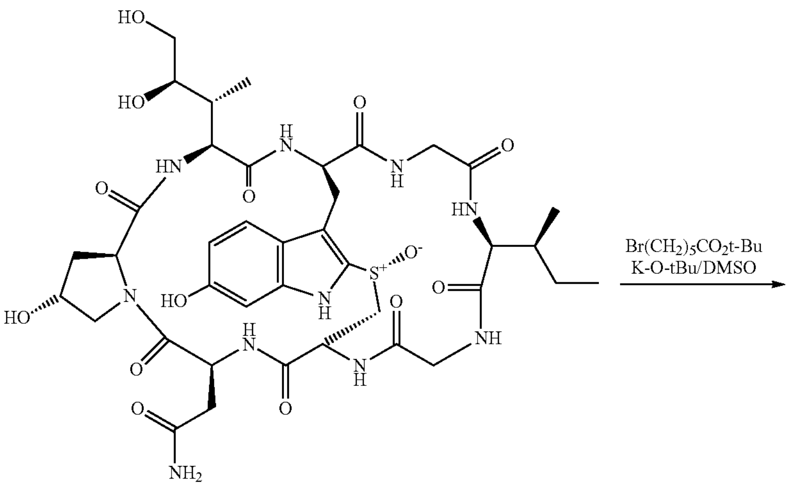
α-amanitin -continued

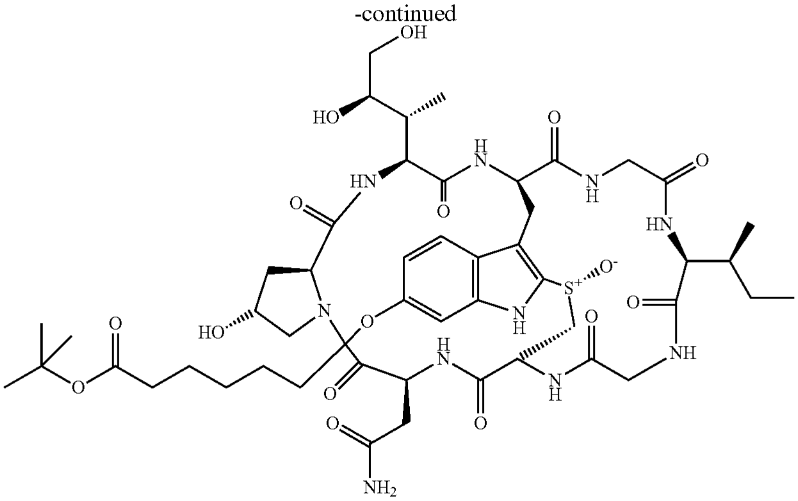

(5)

Under argon 17.07 mg (18.6 μmol) of vacuum dried α-amanitin was dissolved in 1000 μl dry dimethyl sulfoxide (DMSO). 60.1 μl (18.6 μmol, 1 eq.) potassium-tert-butanolate as a 3.09 M solution in DMSO was added at once. After the addition of the base 38 μl (148.6 μmol) of 6-bromoheptanoic acid-tert-butylester was added. The reaction mixture was stirred for 8 hours. After 8, 11, 23, 34, 50 and 52 h additional amounts of potassium-tert-butanolate (60.1 μl) and 6-bromoheptanoic acid-tert-butylester (38 μl) was added. After 56 h the reaction mixture was quenched with 100 μl of a 0.3M solution of acetic acid in DMSO. The volatiles of the reaction mixture were removed at 40° C. and 8 mbar. The crude amanitin ether was purified on a LaPrep-HPLC: column: Kromasil 100-$C_{18}$, 10 μm, 250×20 mm, with methanol/water (0.05% TFA), flow: 26 ml/min, detection at λ=295 nm. Solvent A: 95% water: 5% methanol 0.05% trifluoroacetic acid. Solvent B: 10% water: 90% methanol 0.05% trifluoroacetic acid. Gradient: 0-5 min 100% A; 5-20 min 0% A; 20-25 min 0% A; 25-27 min 100% A; 27-35 min 100% A. The fractions with the same retention time (20.2 min) were collected and the solvent evaporated.

17.88 mg (53% yield) of a white powder. MS: 1089 $M+H^+$; 1111 $M+Na^+$ 1.7.2 Synthesis of 6'-O-(carboxypentyl)-α-amanitin (6)

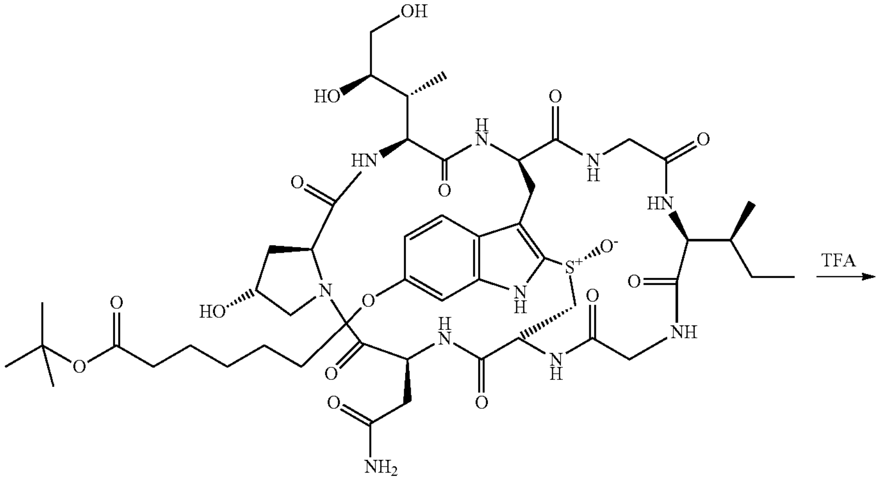

(5)

-continued

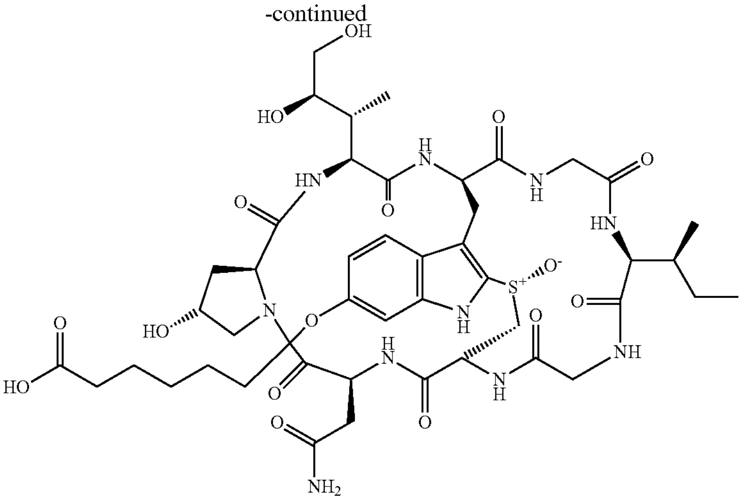

(6)

14.84 mg (13.64 mmol) 6'-(-carboxypentyl-)-α-amanitin (compound (5)) was dissolved under argon in 250 μl trifluoro acetic acid (TFA). The reaction mixture was stirred for 2 minutes and evaporated to dryness at 20° C. The residue was co-evaporated 2 times with 1 ml methanol. The remaining solid was purified on a LaPrep-HPLC: column: Kromasil 100-$C_{18}$, 10 μm, 250x20 mm, with methanol/water (0.05% TFA), flow: 26 ml/min, detection at λ=295 nm. Solvent A: 95% water: 5% methanol 0.05% trifluoroacetic acid. Solvent B: 10% water: 90% methanol 0.05% trifluoroacetic acid. Gradient: 0-5 min 100% A; 5-20 min 0% A; 20-40 min 0% A. The fractions with the same retention time were collected and evaporated.

7.05 mg (50% yield) of a white powder. MS: 1033 $M+H^+$; 1056 $M+Na^+$ 1.7.3 Synthesis of α-amanitin-Herceptin conjugate (7)

10.0 mg of compound (6) was dissolved in 100 μl molecular sieve dried DMF. 80.0 μl solution of N-hydroxysuccinimide (7.4 mg N—OH-Succ/80 μl DMF) and 80.0 μl solution of DCCi (N,N-dicyclohexylcarbodimide; 3.4 mg DCCi/80 μl DMF) was added. Reaction was performed over night at RT. Reaction product was precipitated by 2x30 ml dried diethylether and resolubilized in 800 μl dried DMF. 266 μl of the DMF solution was added to 5.0 ml antibody solution (6 mg/ml in PBS). Reaction was performed over night at RT on a rotating shaker. Isolation of the antibody-conjugate (7) was performed by separation of macromolecular components on a G25-gel filtration column.

(7)

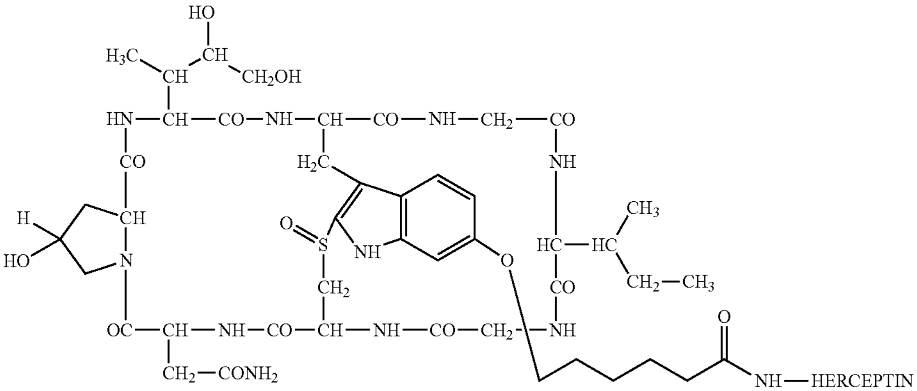

1.8 Synthesis of Amanitin huHEA Conjugate with Linker at Amino Acid 3

1.8.1 Synthesis of α-Amanitin-glutarate 3.0 mg (3.3 μmol) of α-amanitin, dried in vacuo over $P_4O_{10}$ was dissolved in 0.25 ml of dry pyridine and reacted with 0.9 mg (79 μmol) glutaric anhydride in 0.1 ml pyridine for 24 h at RT in the dark. The peptide was precipitated by addition of 7 ml of dry diethylether, centrifuged, and the solid washed a second time with diethylether and centrifuged.

By way of this reaction an α-amanitin derivative is obtained wherein $R_1$=—OH (in FIG. 1) is replaced by $R_1$=—O—C(O)—$(CH_2)_3$—COOH.

1.8.2 Synthesis of α-Amanitin-glutaric acid N-hydroxysuccinimidate 3.4 mg of α-amanitin glutarate (3.3 μmol) was dissolved in 0.05 ml of dry dimethylformamide (DMF), and 2.4 mg (7 eq.) of N-hydroxy-succinimide dissolved in 0.01 ml of DMF were added. After the addition of 1.2 mg of dicyclohexylcarbodiimide in 0.01 ml of DMF the reaction was allowed to proceed for 16 h at RT. The solution was separated from the crystals formed, and the peptide precipitated by the addition of 4 ml of dry diethylether. After centrifugation, the pellet was washed with another 4 ml of ether and centrifuged. The solid was dissolved in 0.1 ml of dimethylformamide and immediately used for the reaction with the antibody solution.

1.8.3 Synthesis of α-Amanitin-glutarate-huHEA125 (huHEA125-Amanitin3)

0.1 ml of the solution of 3.0 mg of α-amanitin-glutaric acid N-hydroxysuccinimidate was added to 10 mg of huHEA125 antibody in 5 ml of PBS and reacted under slow rotation at 5° C. in the dark. After 16 h the solution was applied to a Sephadex G25 column (120×1.5 cm) equilibrated with PBS, and the protein fraction collected. Amanitin load was determined spectrophotometrically from the absorption difference at 310 nm of the protein solution against a blank containing the same concentration of the native antibody, using the molar extinction coefficient for amatoxins of 13.500 $cm^{-1}$. $M^{-1}$. Ratio α-amanitin:IgG of this preparation was ca. 8.

1.9 Synthesis of Amanitin Herceptin Conjugates with Linker at Amino Acid 3

1.9.1 Synthesis of δ-O—(NH-boc-6-aminohexylcarbamoyl)-α-amanitin (8)

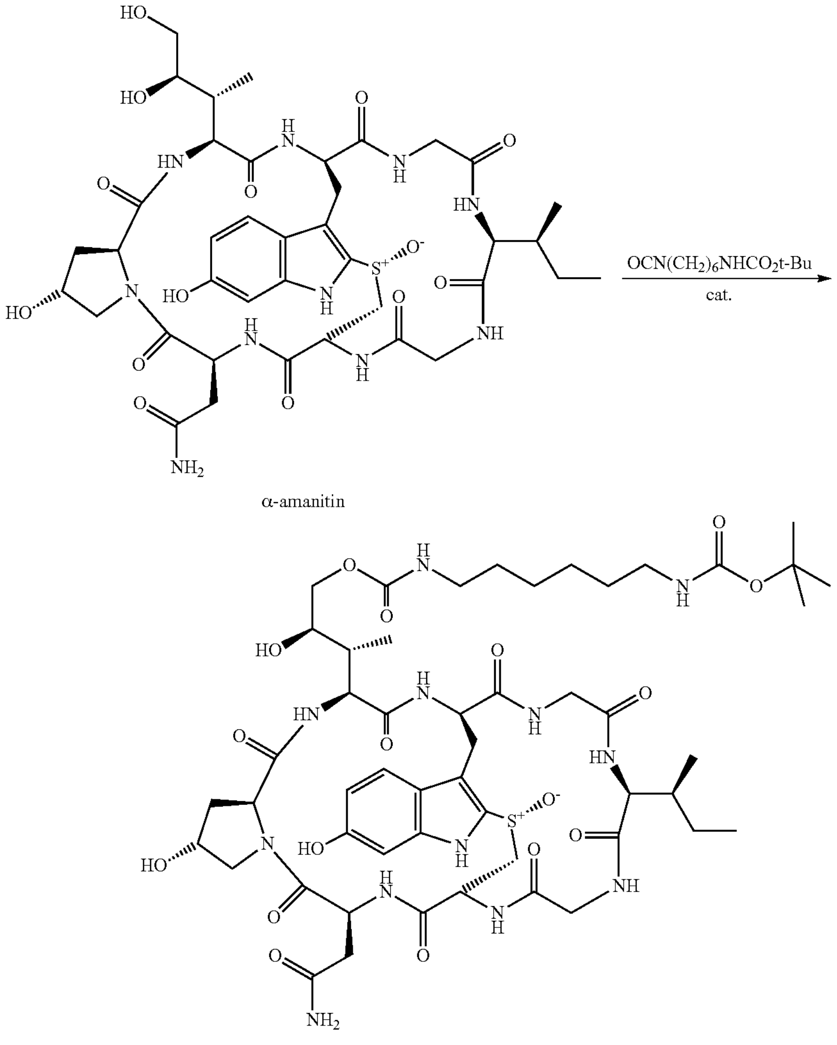

α-amanitin (8)

cat.: dibutyl dilaurylstannate n-$bu_2Sn[OCO(CH_2)_{10}CH_3]_2$

Under argon 13.43 mg (14.6 μmol) vacuum dried α-amanitin was dissolved in 1000 ml dry dimethyl formamide (DMF). 7.08 mg (29.2 mop NH-Boc-6-isocyanato aminohexane and 18.46 mg (29.2 μmol) di-Butyl dilauryl-stannate was added and the reaction mixture stirred at ambient temperature. After 23 hours additional 13.43 mg (14.6 mop NH-Boc-6-isocyanatoaminohexane was added. After 52 hours the reaction mixture was hydrolyzed with 200 μl methanol and evaporated to dryness. The residue was dissolved in 1200 μl DMSO and purified on a LaPrep-HPLC: column: Kromasil 100-C18, 10 μm, 250×20 mm, with methanol/water (0.05% TFA), flow: 26 ml/min, detection at λ=295 nm. Solvent A: 95% water:5% methanol. Solvent B: 5% water: 95% methanol. Gradient: 0-5 min 100% A; 5-20 min 0% A; 20-25 min 0% A; 25-27 min 100% A; 27-35 min 100% A. The fractions with the same retention time were collected and the solvents evaporated.

9.06 mg (53% yield) of a white solid. MS: 1161 $M+H^+$; 1183 M 1.9.2 Synthesis of δ-O-(6-aminohexylcarbamoyl)-α-amanitin (9)

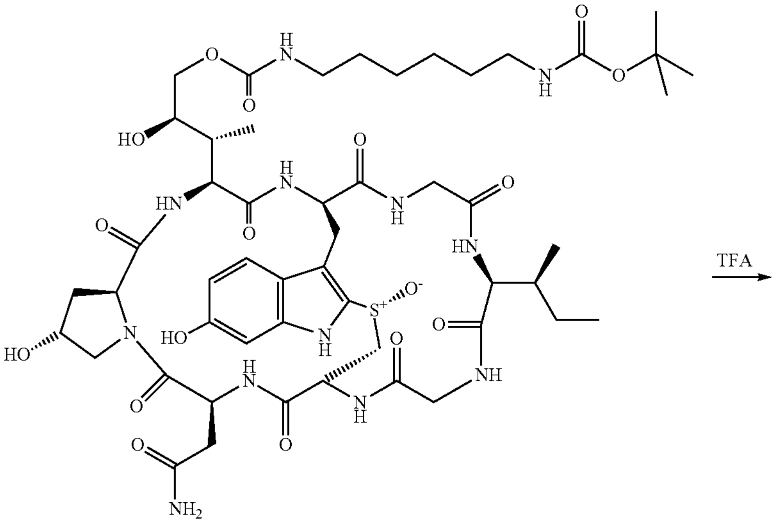

(8)

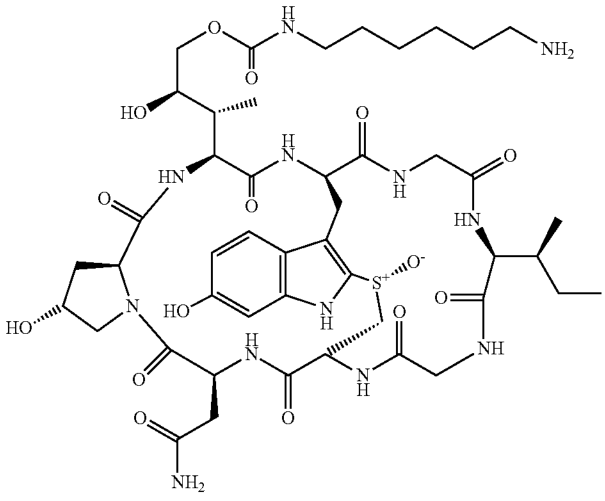

(9)

9.06 mg (7.8 μmol) compound (8) was dissolved in 250 μl trifluoroacetic acid and stirred for 2 minutes at ambient temperature. The reaction mixture was evaporated to dryness and the residue koevaporated 2 times with 1.5 ml acetonitrile. The solid was purified on a LaPrep-HPLC: column: Kromasil 100-C18, 10 250x20 mm, with acetonitrile/water, flow: 26 ml/min, detection at k=295 nm. Solvent A: 95% water: 5% acetonitrile. Solvent B: 5% water: 95% acetonitrile. Gradient: 0-5 min 100% A; 5-20 min 0% A; 20-25 min 0% A; 25-27 min 100% A; 27-35 min 100% A. The fractions with the retention time between 12-17 min were collected and evaporated to a white solid.

8.75 mg (95% yield). MS: 1061 $M+H^+$; 1083 $M+Na^+$ 1.9.3 Synthesis of α-amanitin-Herceptin conjugates 2.0 mg of compound (9) was dissolved in 113 μl ft molecular sieve dried DMF. 21.8 μl solution of DSS (disuccinimidyl suberate; 3.7 mg DSS/100 μl DMF) or 23.9 μl solution of DSP (dithiobis(succinimidyl) propionate; 3.7 mg DSP/100 μl DMF) and 5.7 μl triethylamine was added respectively. The reaction was performed over night at RT. Reaction products were precipitated by 2x30 ml dried diethylether and resolubilized in 200 μl dried DMF. 122 μl (DSS) or 176 μl (DSP) of the DMF solutions were added to 6.0 ml of a solution of Her-2 specific Herceptin antibody (2 mg/ml in PBS). The reaction was performed over night at RT on a rotating shaker. The isolation of the antibody-conjugate (10) and (11), respectively, was performed by separation of macromolecular components on a G25-gel filtration column.

(10)
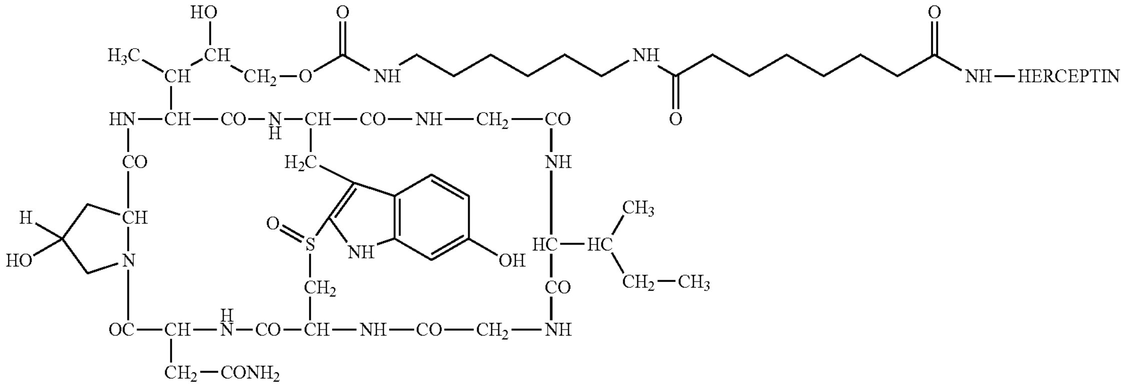
(11)
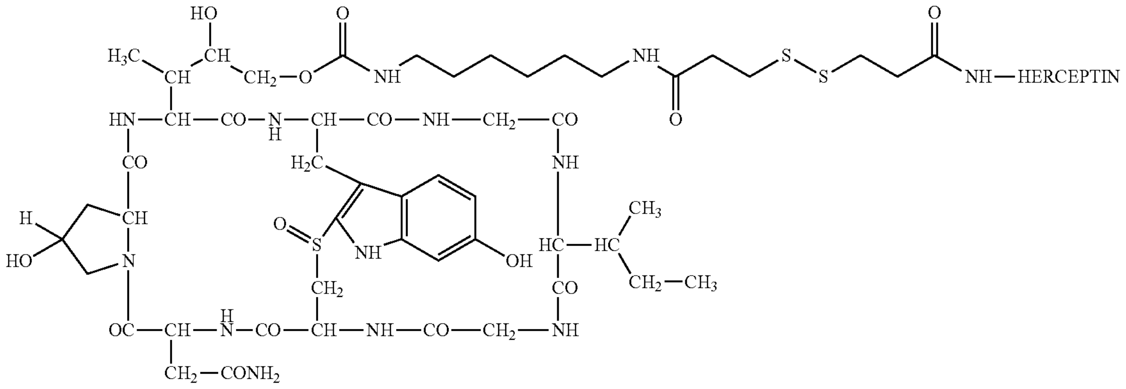
1.10 Synthesis of Amanitin Herceptin Conjugates with Linker at Amino Acid 3
1.10.1 Synthesis of δ-O-(5-O-t-butyl-carboxypentylcarbamoyl)-α-amanitin (12)
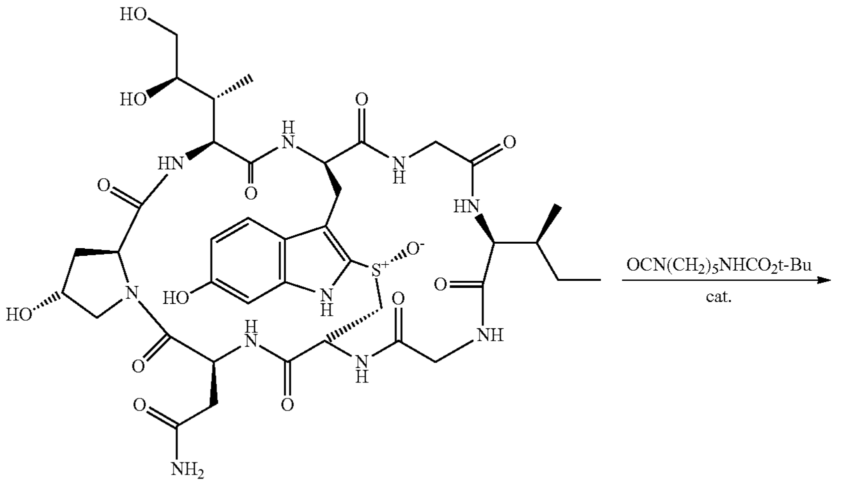
α-amanitin -continued

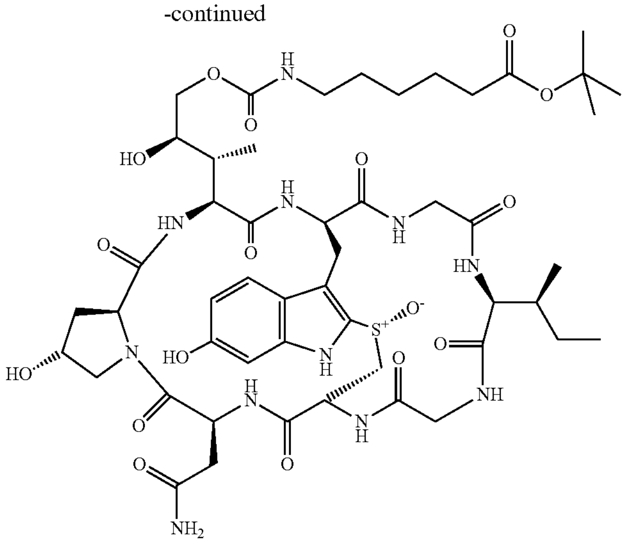

(12)

cat.: dibutyl dilaurylstannate n-$bu_2Sn[OCO(CH_2)_{10}CH_3]_2$

Under argon 30.76 mg (33.5 mop vacuum dried α-amanitin was dissolved in 1000 μl dry dimethyl formamide (DMF). 14.28 mg (13.83 μl, 66.9 μmol) isocyanatohexanoic acid-tert-butylester and 42.28 mg (40.26 μl, 66.9 μmol) dibutyll dilaurylstannate was added. After 23 hours stirring at room temperature additional isocyanato ester (13.83 μl) was added and the reaction mixture was quenched with methanol after 33 hours. The reaction mixture was evaporated to dryness and the remaining solid was dissolved in DMSO and purified on a LaPrep-HPLC: column: Kromasil 100-C18, 10 μm, 250×20 mm, with methanol/water (0.05% TFA), flow: 26 ml/min, detection at k=295 nm. Solvent A: 95% water: 5% methanol 0.05% trifluoroacetic acid. Solvent B: 10% water: 90% methanol 0.05% trifluoroacetic acid. Gradient: 0-5 min 100% A; 5-20 min 0% A; 20-25 min 0% A; 25-27 min 100% A; 27-35 min 100% A. The fractions with the same retention time were collected and the solvents evaporated.

17.95 mg (47% yield) of a powder. MS: 1133 $M+H^+$; 1155 $M+Na^+$ 1.10.2 Synthesis of δ-O-(carboxypentylcarbamoyl)-α-amanitin (13)

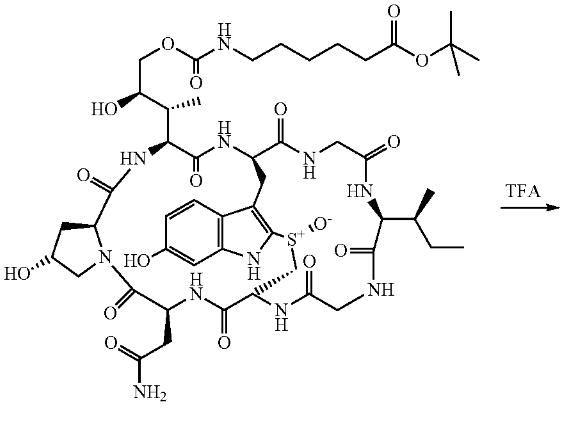

(12)

-continued

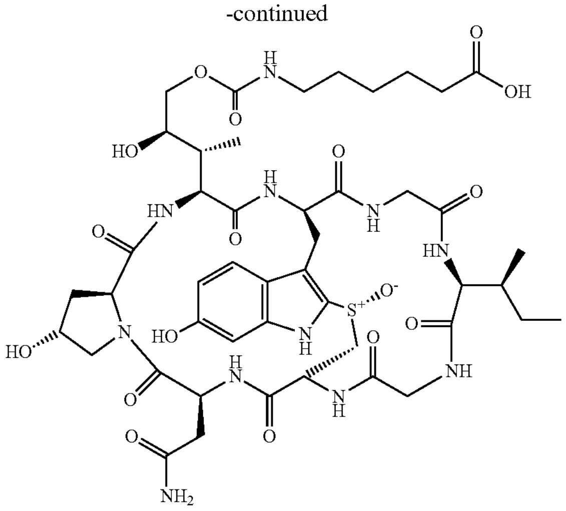

(13)

17.95 mg (15.9 mmol) tert-butylester (Compound (12)) was dissolved in 500 ml trifluoro acetic acid (TFA) and stirred for 2 minutes at ambient temperature. Excess trifluoro acetic acid was removed in vacuum and the remaining solid was coevaporated two times with 1.5 ml acetonitrile. The free carboxylic derivative (13) was purified on a LaPrep-HPLC: column: Kromasil 100-$C_{18}$, d=10 mm, 10 mm, 250×20 mm, with acetonitril/water, flow: 26 ml/min, detection at λ=295 nm. Solvent A: 95% water: 5% acetonitrile. Solvent B: 5% water: 95% acetonitrile. Gradient: 0-5 min 100% A; 5-20 min 0% A; 20-25 min 0% A; 25-27 min 100% A; 27-35 min 100% A. The fractions with the same retention time 12-17 min were collected and the solvents evaporated.

11.34 mg (66% yield) of a white slid. MS: 1076 $M+H^+$; 1098 $M+Na^+$ 1.10.3 Synthesis of Synthesis of Herceptin-α-amanitin conjugate 10.0 mg HDP compound (13) was dissolved in 100 ml molecular sieve dried DMF. 80.0 μl solution of N-hydroxysuccinimide (7.4 mg N—OH-Succ/80 μl DMF) and 80.0 μl solution of DCCi (N,N-dicyclohexylcarbodimide; 3.4 mg DCCi/80 μl DMF) were added. The reaction was performed over night at RT. The reaction product was precipitated by 2×30 ml dried diethylether and resolubilized in 800 ml dried DMF. 266 ml of the DMF solution was added to 5.0 ml antibody solution (6 mg/ml in PBS). Reaction was performed over night at RT on a rotating shaker. The isolation of the antibody-conjugate (14) was performed by separation of macromolecular components on a G25-gel filtration column.

ceptin antibody in 5 ml of PBS and reacted under slow rotation at 5° C. in the dark. After 16 h the solution was applied to a Sephadex G25 column (120×1.5 cm) equilibrated with PBS, and the protein fraction collected. Amanitin load was determined spectrophotometrically from the absorption difference at 310 nm of the protein solution against a blank containing the same concentration of the native antibody, using the molar extinction coefficient for amatoxins of 13.500 $cm^{-1}$. $M^{-1}$. Ratio α-amanitin:IgG of this preparation was about 4.

(14)

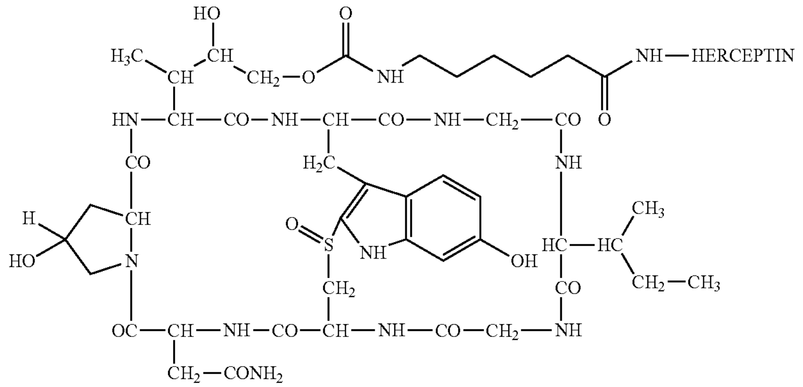

1.11 Synthesis of Amanitin Herceptin Conjugates with Linker at Amino Acid 3

1.11.1 Synthesis of α-Amanitin-glutarate 3.0 mg (3.3 μmol) of α-amanitin, dried in vacuo over $P_4O_{10}$ was dissolved in 0.25 ml of dry pyridine and reacted with 0.9 mg (79 μmol) glutaric anhydride in 0.1 ml pyridine for 24 h at RT in the dark. The peptide was precipitated by addition of 7 ml of dry diethylether, centrifuged, and the solid washed a second time with diethylether and centrifuged.

By way of this reaction an α-amanitin derivative is obtained wherein $R_1$=—OH (in FIG. 1) is replaced by $R_1$=—O—C(O)—$(CH_2)_3$—COOH.

1.11.2 Synthesis of α-Amanitin-glutaric acid N-hydroxysuccinimidate 3.4 mg of α-amanitin glutarate (3.3 μmol) was dissolved in 0.05 ml of dry dimethylformamide (DMF), and 2.4 mg (7 eq.) of N-hydroxy-succinimide dissolved in 0.01 ml of DMF were added. After the addition of 1.2 mg of dicyclohexylcarbodiimide in 0.01 ml of DMF the reaction was allowed to proceed for 16 h at RT. The solution was separated from the crystals formed, and the peptide precipitated by the addition of 4 ml of dry diethylether. After centrifugation, the pellet was washed with another 4 ml of ether and centrifuged. The solid was dissolved in 0.1 ml of dimethylformamide and immediately used for the reaction with the antibody solution.

1.11.3 Synthesis of α-Amanitin-glutarate-Herceptin (15)

0.1 ml of the solution of 3.0 mg of α-amanitin-glutaric acid N-hydroxysuccinimidate was added to 10 mg of Her- (15)

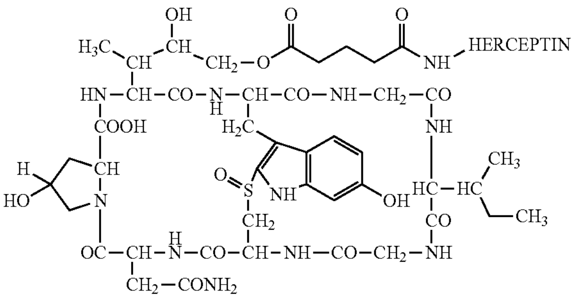

1.12. Synthesis of Aminophalloidin (APHD)-suberoyl-huHEA125

Aminophalloidin was prepared from mono-tosylphalloidin by reaction with methanolic ammonia. Conjugation of aminophalloidin with huHEA125 was performed in analogy to the reaction described in 1.5.3.

Example 2

Binding Studies 2.1 Binding Competition Analysis

Binding of conjugate huHEA125-amanitin3 vs. non-conjugated huHEA125 antibody was analyzed in a competition experiment by flow cytometry. The α-amanitin-huHEA125 conjugate was synthesized as described above in sections 1.6.1 to 1.6.3.

Colo205 target cells (colon cancer metastasis) were washed twice in FACS buffer (Dulbecco's PBS with 1% heat-inactivated fetal calf serum and 0.1% sodium azide) counted and adjusted to $2\times10^7$ cells per ml. Fifty µl of cell suspension was given to each well of a 96 well U-bottom microtiter plate to which 50 µl/well of FITC-labeled huHEA125 antibody was pipetted. Serial dilutions of amanitin-huHEA125 or huHEA125 ranging from 400 µg/ml to 10 ng/ml final dilution were added in triplicates in a volume of 50 µl/well and incubated for 1 h on ice. Subsequently, the plate was centrifuged (2 min at 2000 rpm) and the supernatant was removed from the cells. Cells were re-suspended in 150 µl of FACS buffer and centrifuged again. After two washing steps by centrifugation, cells were taken up in 100 µl/well of propidium iodide solution (1 µg/ml in FACS buffer) allowing discrimination of dead cells. Analysis was performed on a FACScan cytometer (Becton and Dickinson, Heidelberg, Germany) using CellQuest software.

Figure 2:
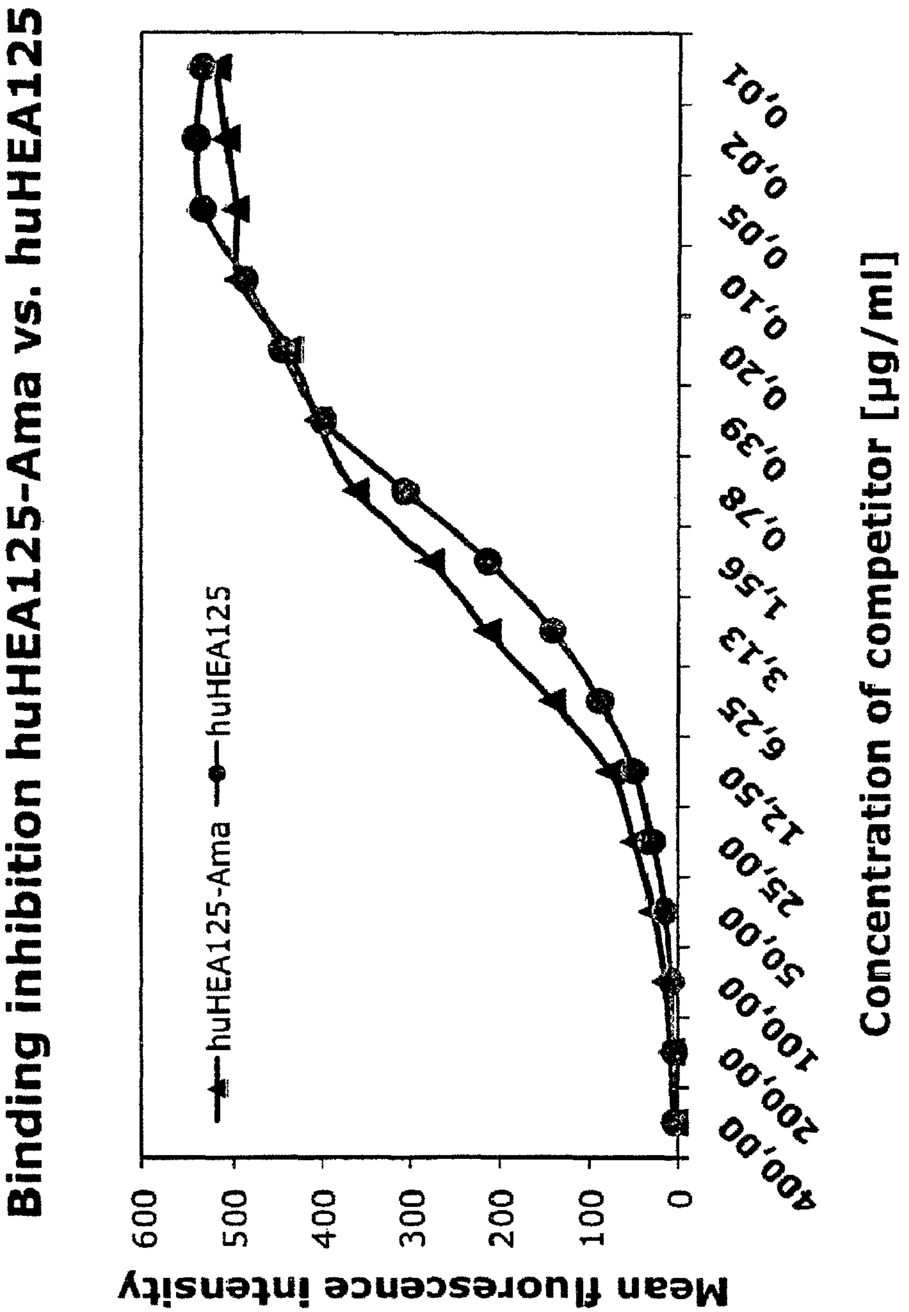
FIG. 2 shows a comparison of the binding affinities of huHEA125-Ama and huHEA125 to target cells by a binding competition analysis. EpCAM-expressing Colo205 cells were incubated with a fixed amount of directly FITC-labeled mouse HEA125 antibody. Binding to target cells was analyzed by flow cytometry. Competition of binding with increasing amounts of huHEA125-Ama or huHEA125 revealed a very similar affinity towards the target antigen.

As shown in FIG. 2 competition of binding to target cells with increasing amounts of huHEA125-amanitin conjugate or unmodified huHEA125 antibody revealed a comparable binding strength over the whole concentration range from 10 ng/ml to 400 µg/ml competing antibody or antibody conjugate. Therefore, the conjugation procedure did not significantly alter the affinity of huHEA125-amanitin to the target cells.

Figure 3A:
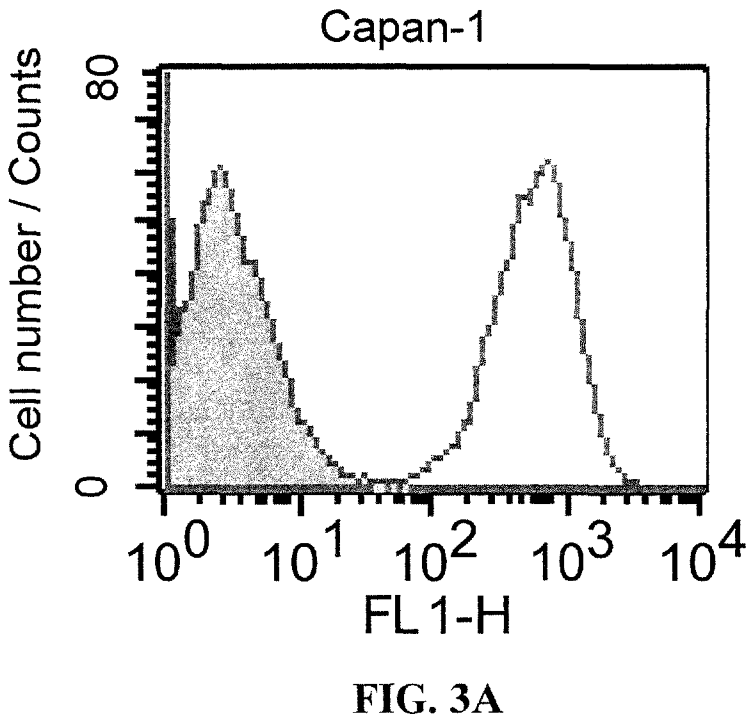
FIGS. 3A-3D show the surface expression of EpCAM antigen on various carcinoma cell lines detected by indirect immunofluorescence.
Figure 3B:
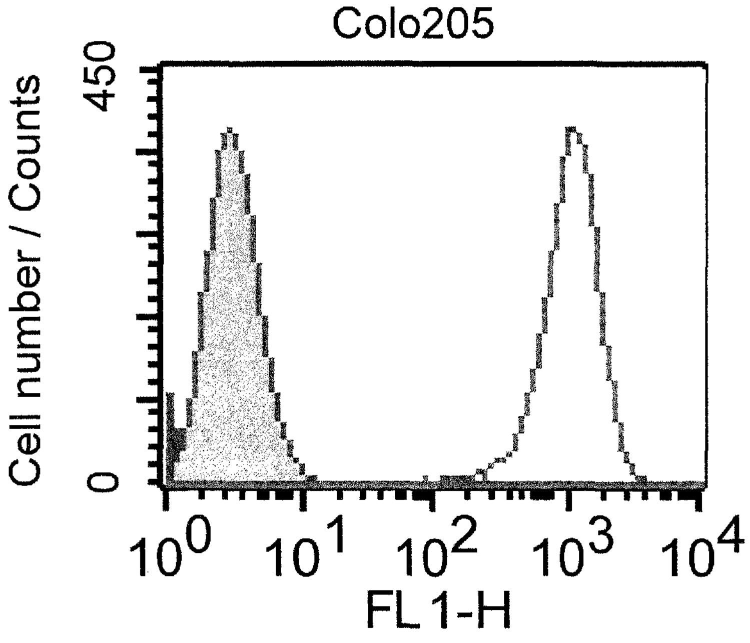
Figure 3C:
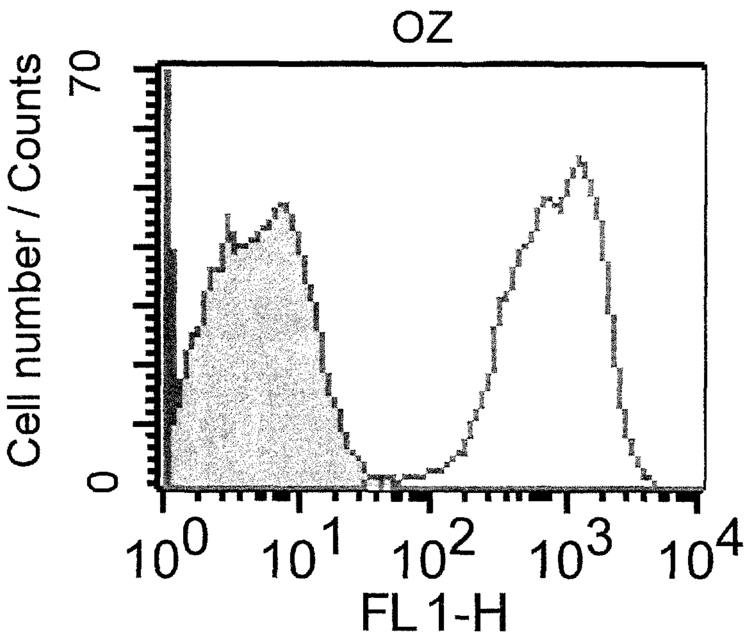
Figure 3D:
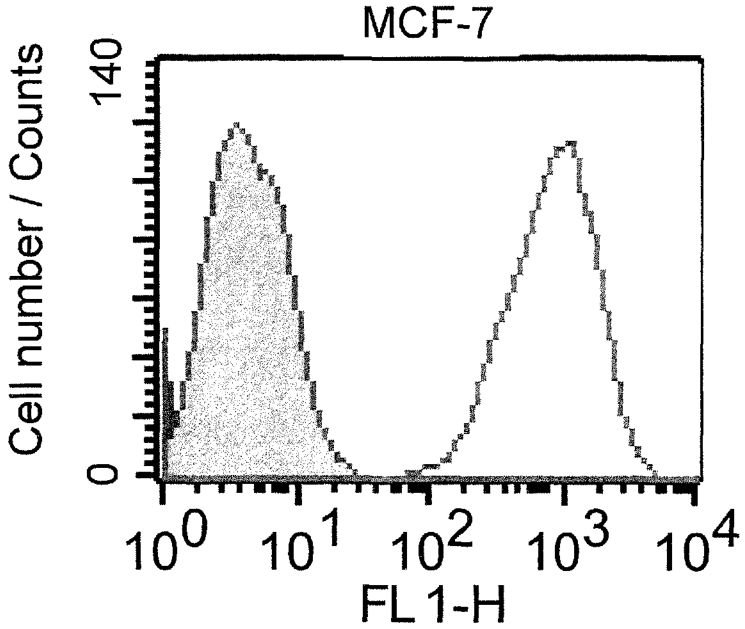

2.2 Surface Expression of EpCAM Antigen on Various Carcinoma Cell Lines Detected by Indirect Immunofluorescence Cell lines Capan-1, Colo205, OZ, and MCF-7 were first incubated with either huHEA125 or Xolair®. After washing, binding of the primary antibody was visualized by FITC-labelled $F(ab')_2$ goat anti-human IgG (H+L) as second step reagent. The results are shown in FIG. 3A (Capan-1), FIG. 3B (Colo205), FIG. 3C (OZ), and FIG. 3D (MCF-7). The grey-shaded histograms in the left side of each diagram show the results obtained with control antibody Xolair®; the histograms having a white area in the right side of each diagram show the results obtained with antibody huHEA125.

2.3 Binding of huHEA125-Amanitin and huHEA125-phalloidin Conjugates to MCF-7 Breast Cancer Cells Binding of huHEA125-amanitin and huHEA125-phalloidin conjugates versus non-conjugated huHEA125 antibody was analyzed by flow cytometry. MCF-7 target cells were washed twice in FACS buffer (Dulbecco's PBS with 1% heat-inactivated fetal calf serum and 0.1% sodium azide) counted and adjusted to $2\times10^7$ cells per ml. Fifty µl of cell suspension was given to each well of a 96 well U-bottom microtiter plate. Immunotoxins huHEA125-amanitin1, huHEA125-amanitin4 and huHEA125-phalloidin as well as unconjugated huHEA125 antibody were added at a concentration of 1 µg/ml in a volume of 100 µl per well and incubated for 1 h on ice. The plate was centrifuged (2 min at 2000 rpm) and the supernatant was removed from the cells. Cells were re-suspended in 150 µl of FACS buffer and centrifuged again. Subsequently, 100 µl of FITC-labeled $F(ab')_2$ goat anti-human IgG (H+L) secondary antibody was added per well and incubated again for 1 h on ice. After two washing steps by centrifugation, cells were taken up in 100 µl/well of propidium iodide solution (1 µg/ml in FACS buffer) allowing discrimination of dead cells. Analysis was performed on a FACScan cytometer (Becton and Dickinson, Heidelberg, Germany) using CellQuest software.

Figure 4:
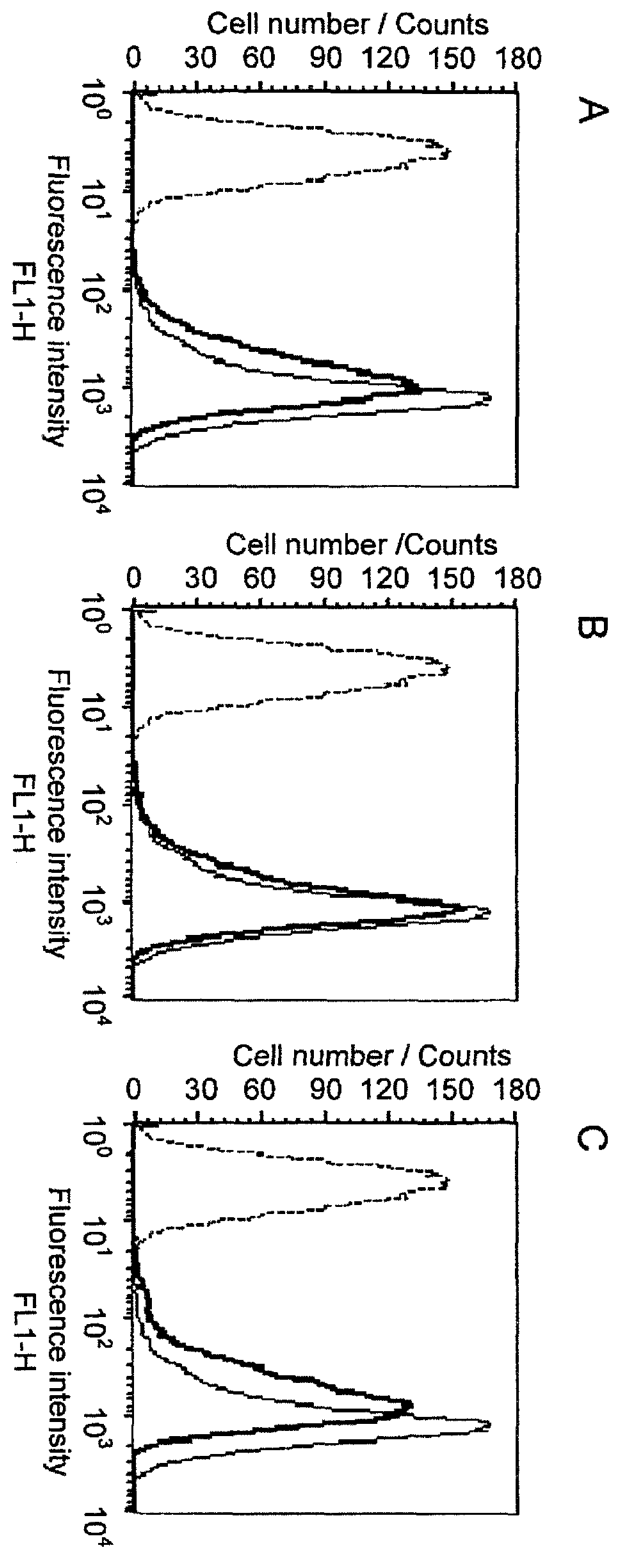
FIG. 4 shows the binding of huHEA125-Amanitin and huHEA125-Phalloidin conjugates to MCF-7 breast cancer cells analyzed by flow cytometry. The abbreviation FL1-H stands for "fluorescence 1 height" which means the intensity of fluorescence 1, i.e. the green channel for FITC.

As shown in FIG. 4 the binding capacity of immunotoxins to target cells was only moderately reduced by the conjugation procedure. When compared with the non-modified huHEA125 antibody showing a mean fluorescence intensity (MFI) of 1094, conjugation with amanitin1 decreased binding to MFI 730, conjugation with amanitin4 resulted in a MFI of 905, whereas coupling to alpha-phalloidin reduced MFI to 604. These values were obtained with identical antibody amounts of conjugates.

Example 3

Specific Growth Inhibition of Carcinoma Cells by Immunoconjugates Composed of huHEA125 Antibody and Amanitin at Different Binding Sites 3.1 Proliferation Assay Inhibition of cell growth by amanitin-IgG conjugates was determined by incorporation of [$^3$H]-thymidine. Serial dilutions of amanitin-huHEA125 and amanitin in complete medium (RPMI 1640 supplemented with 10% heat-inactivated FCS, 2 mM L-glutamine and 1 mM sodium pyruvate) ranging from $2\times10^{-5}$ M to $6\times10^{-13}$ M were prepared in triplicates in a volume of 100 µl in the wells of a 96 well flat-bottom tissue culture microtiter plate. In each well, cells were added in 50 µl at a density of $5\times10^4$ per ml in the experiments with huHEA125-Amanitin1 and huHEA125-Amanitin4 and at a density of $2\times10^4$ per ml in the experiments with huHEA125-Amanitin3. Plates were incubated in a humidified atmosphere at 37° C. and 5% $CO_2$ for 72 or 96 h. At 20 h before the end of the assay, 1 µCi of [$^3$H]-thymidine was added. Subsequently, plates were processed with a Tomtec cell harvester and the incorporated radioactivity was determined by liquid scintillation counting (Wallac Betaplate Liquid Scintillation Counter, PerkinElmer Life and Analytical Sciences) and given as cpm.

3.2 Comparison of Inhibition of Carcinoma Cell Proliferation Caused by Conjugates Using Different Linkage Sites in the Amanitin Moiety Three examples of growth inhibition induced by different amanitin-IgG conjugates are depicted in FIGS. 5, 6, and 9. In all three experiments MCF-7 cells were used. FIG. 5 shows a comparison of huHEA125-Amanitin1 with the non-binding control Xolair-Amanitin1 and with free Amanitin. In the experiment outlined in FIG. 6 huHEA125-Amanitin4 was compared with an alpha-phalloidin huHEA125 conjugate and with free Amanitin. FIG. 9 shows a comparison of huHEA125-Amanitin3 with Amanitin-armed control antibody Xolair and with free Amanitin.

The $IC_{50}$ of conjugates huHEA125-amanitin1 and huHEA125-amanitin4 were both approximately $5\times10^{-12}$ M (FIGS. 5 and 6) and the $IC_{50}$ of conjugate huHEA125-amanitin3 was approximately $2\times10^{-12}$ M (FIG. 9). In contrast, the phalloidin-huHEA125 preparation exhibited virtually no effect at least at the dose levels tested (FIG. 6). In accordance with our previous findings, the $IC_{50}$ of Amanitin alone is in the range of $10^{-7}$ M (FIGS. 5, 6, and 9).

3.3 Comparison of Inhibition of Carcinoma Cell Proliferation for Different Carcinoma Cell Lines Four examples of growth inhibition tested in four different carcinoma cell lines are depicted in FIGS. 7, 8, 9, and 10. In all four experiments, the conjugate huHEA125-Amanitin3 was used.

In case of the pancreatic carcinoma cell line Capan-1 the huHEA125-Amanitin3 immunotoxin induced growth arrest at amanitin concentrations of $1\times10^{-11}$ to $3\times10^{-10}$ M as depicted in FIG. 7.

In case of the colon cancer cell line Colo205 the huHEA125-Amanitin3 immunotoxin induced growth arrest at amanitin concentrations of $1\times10^{-12}$ to $4\times10^{-11}$ M as depicted in FIG. 8.

In case of the breast cancer cell line MCF-7 the huHEA125-Amanitin3 immunotoxin induced growth arrest at amanitin concentrations of $1\times10^{-12}$ to $1\times10^{-11}$ M as depicted in FIG. 9.

In case of the cholangiocarcinoma cell line OZ the huHEA125-Amanitin3 immunotoxin induced growth arrest at amanitin concentrations of $1\times10^{-11}$ to $6\times10^{-10}$ M as depicted in FIG. 10.

Example 4

Specific Growth Inhibition of Carcinoma Cells by Immunoconjugates Composed of Herceptin Antibody and Amanitin at Different Binding Sites and Using Different Linking Chemistry Inhibition of cell growth by amanitin-Herceptin conjugates was determined by in vitro BrdU incorporation as described in Current Protocols in Immunology 1 (see chapter 7.10. Coligan, J. E. et al., eds.) John-Wiley & Sons, New York). Compounds (3), (4), (7), (10), (11), (14), non-conjugated Herceptin and α-amanitin as such were incubated for 72 h and 120 h, respectively, with three tumor cell lines expressing Her2/neu in high concentration, namely, SKOV-3, SK-BR-3 and NCI-N87 and one Her2/neu negative cell line MDA-MB231. Non conjugated Herceptin showed no cytotoxicity on any cell line while the various amanitin conjugates showed a marked toxicity on the Her2/neu positive cell lines with an $EC_{50}$ in the pico- to nanomolar range, no significant toxicity was observed on the Her2/neu negative cell line. (See FIGS. 11A to 11D). The indicated molar concentration is indicated on the basis of the entire amanitin comprised in the respective conjugate.

Example 5

In Vivo Xenograft Tumor Model

A mouse tumor xenograft model, wherein $2.5\times10^{\&}$ SKOV-3 ovarial carcinoma cells are implanted sub-cutaneously (s.c.) into SCID mice and allowed to grow for 10 days. After 10 days a single dose of 30 µg/kg body weight (see FIG. 12A) or at 150 µg/kg body weight (see FIG. 12B) of various α-amanitin-Herceptin conjugates (Compounds (15), (3), (4), (10), (11), and (7)) and non-conjugated Herceptin (Control) were administered intravenously. A clear concentration dependent reduction of tumor growth was observed. Conjugates (7), (10) and (15) led to full tumor remission within the period of observation, i.e. 87 days from the initiation of the experiment.

REFERENCES

Al-Hajj M., Wicha M. S., Benito-Hernandez A., Morrison S. J., Clarke M. F. Prospective identification of tumorigenic breast cancer cells. Proc. Natl. Acad. Sci. USA 100(7), 3983-3988 (2003)

Allard W. J., Matera J., Miller M. C., Repollet M., Connelly M. C., Rao C., Tibbe A. G., Uhr J. W., Terstappen L. W. Tumor cells circulate in the peripheral blood of all major carcinomas but not in healthy subjects or patients with nonmalignant diseases. Clin. Cancer Res. 10(20), 6897-6904 (2004)

Baeuerle P. A. and Gires O. EpCAM (CD326) finding its role in cancer. Br. J. Cancer 96(3), 417-423 (2007)

Balzar M., Winter M. J., de Boer C. J., Litvinov S. V. The biology of the 17-1A antigen (Ep-CAM). J. Mol. Med. 77(10), 699-712 (1999)

Binz H. K., Amstutz P., Plückthun A. Engineering novel binding proteins from nonimmunoglobulin domains. Nat Biotechnol. 23(10):1257-1268 (2005)

Brody E. N. and Gold L., Aptamers as therapeutic and diagnostic agents. J. Biotechnol. 74(1):5-13 (2000)

Dalerba P., Dylla S. J., Park I. K., Liu R., Wang X., Cho R. W., Hoey T., Gurney A., Huang E. H., Simeone D. M., Shelton A. A., Parmiani G., Castelli C., Clarke M. F. Phenotypic characterization of human colorectal cancer stem cells. Proc. Natl. Acad. Sci. USA 104(24), 10158-10163 (2007)

Gastl G., Spizzo G., Obrist P., Dünser M., Mikuz G. Ep-CAM overexpression in breast cancer as a predictor of survival. Lancet 356(9246), 1981-1982 (2000)

Holliger P., Prospero T., Winter G. "Diabodies": small bivalent and bispecific antibody fragments. Proc. Natl. Acad. Sci. U.S.A. 90(14), 6444-6448 (1993)

Leuenberger, H. G. W, Nagel, B. and Kölbl, H. eds. "A multilingual glossary of biotechnological terms: (IUPAC Recommendations)", Helvetica Chimica Acta, CH-4010 Basel, Switzerland), 1995

Li C., Heidt D. G., Dalerba P., Burant C. F., Zhang L., Adsay V., Wicha M., Clarke M. F., Simeone D. M. Identification of pancreatic cancer stem cells. Cancer Res. 67(3), 1030-1037 (2007)

Moldenhauer G., Momburg F., Möller P., Schwartz R., Hämmerling G. J. Epithelium-specific surface glycoprotein of Mr 34,000 is a widely distributed human carcinoma marker. Br. J. Cancer 56(6), 714-721 (1987)

Momburg F., Moldenhauer G., Hämmerling G. J., Möller P. Immunohistochemical study of the expression of a Mr 34,000 human epithelium-specific surface glycoprotein in normal and malignant tissues. Cancer Res. 47(11), 2883-2891 (1987)

Nagrath S., Sequist L. V., Maheswaran S., Bell D. W., Irimia D., Ulkus L., Smith M. R., Kwak E. L., Digumarthy S., Muzikansky A., Ryan P., Balis U. J., Tompkins R. G., Haber D. A., Toner M. Isolation of rare circulating tumour cells in cancer patients by microchip technology. Nature 450(7173), 1235-1239 (2007)

Spizzo G., Obrist P., Ensinger C., Theurl I., Dtinser M., Ramoni A., Gunsilius E., Eibl G., Mikuz G., Gastl G. Prognostic significance of Ep-CAM AND Her-2/neu overexpression in invasive breast cancer. Int. J. Cancer 98(6), 883-888 (2002)

Spizzo G., Went P., Dirnhofer S., Obrist P., Simon R., Spichtin H., Maurer R., Metzger U., von Castelberg B., Bart R., Stopatschinskaya S., Köchli O. R., Haas P., Mross F., Zuber M., Dietrich H., Bischoff S., Mirlacher M., Sauter G., Gastl G. High Ep-CAM expression is associated with poor prognosis in node-positive breast cancer. Breast Cancer Res. Treat. 86(3), 207-213 (2004)

Trzpis M., McLaughlin P. M., de Leij L. M., Harmsen M. C. Epithelial cell adhesion molecule: more than a carcinoma marker and adhesion molecule. Am. J. Pathol. 171(2), 386-395 (2007)

Varga M., Obrist P., Schneeberger S., Mühlmann G., Felgel-Farnholz C., Fong D., Zitt M., Brunhuber T., Schäfer G., Gastl G., Spizzo G. Overexpression of epithelial cell adhesion molecule antigen in gallbladder carcinoma is an independent marker for poor survival. Clin. Cancer Res. 10(9), 3131-3136 (2004)

Went P. T., Lugli A., Meier S., Bundi M., Mirlacher M., Sauter G., Dirnhofer S. Frequent EpCam protein expression in human carcinomas. Hum. Pathol. 35(1), 122-128, 2004

Wieland, T. and Faulstich H. Amatoxins, phallotoxins, phallolysin, and antamanide: the biologically active components of poisonous *Amanita* mushrooms. CRC Crit. Rev. Biochem. 5(3), 185-260 (1978)

Winter M. J., Nagtegaal I. D., van Krieken J. H., Litvinov S. V. The epithelial cell adhesion molecule (Ep-CAM) as a morphoregulatory molecule is a tool in surgical pathology. Am. J. Pathol. 163(6), 2139-2148 (2003)

SEQUENCE LISTING-FREE TEXT INFORMATION

SEQ ID NO: 1: chimeric antibody huHEA125, heavy chain, membrane-bound form
SEQ ID NO: 2: chimeric antibody huHEA125, heavy chain, secreted form
SEQ ID NO: 3: chimeric antibody huHEA125, heavy chain, VH domain
SEQ ID NO: 4: chimeric antibody huHEA125, heavy chain, FR1 segment
SEQ ID NO: 5: chimeric antibody huHEA125, heavy chain, CDR1 segment
SEQ ID NO: 6: chimeric antibody huHEA125, heavy chain, FR2 segment
SEQ ID NO: 7: chimeric antibody huHEA125, heavy chain, CDR2 segment
SEQ ID NO: 8: chimeric antibody huHEA125, heavy chain, FR3 segment
SEQ ID NO: 9: chimeric antibody huHEA125, heavy chain, CDR3 segment
SEQ ID NO: 10: chimeric antibody huHEA125, heavy chain, FR4 segment
SEQ ID NO: 11: chimeric antibody huHEA125, light chain
SEQ ID NO: 12: chimeric antibody huHEA125, light chain, VL domain
SEQ ID NO: 13: chimeric antibody huHEA125, light chain, FR1 segment
SEQ ID NO: 14: chimeric antibody huHEA125, light chain, CDR1 segment
SEQ ID NO: 15: chimeric antibody huHEA125, light chain, FR2 segment
SEQ ID NO: 16: chimeric antibody huHEA125, light chain, CDR2 segment
SEQ ID NO: 17: chimeric antibody huHEA125, light chain, FR3 segment
SEQ ID NO: 18: chimeric antibody huHEA125, light chain, CDR3 segment
SEQ ID NO: 19: chimeric antibody huHEA125, light chain, FR4 segment
SEQ ID NO: 20: chimeric antibody huHEA125, heavy chain, CDR1 domain
SEQ ID NO: 21: chimeric antibody huHEA125, heavy chain, CDR2 domain
SEQ ID NO: 22: chimeric antibody huHEA125, heavy chain, CDR3 domain
SEQ ID NO: 23: chimeric antibody huHEA125, light chain, CDR1 domain
SEQ ID NO: 24: chimeric antibody huHEA125, light chain, CDR2 domain
SEQ ID NO: 25: chimeric antibody huHEA125, light chain, CDR3 domain
SEQ ID NO: 26: chimeric antibody huHEA125, heavy chain, constant domain, membrane bound form
SEQ ID NO: 27: chimeric antibody huHEA125, heavy chain, constant domain, secreted form
SEQ ID NO: 28: chimeric antibody huHEA125, light chain, constant domain

We claim:

1. A target-binding moiety toxin conjugate comprising:
(i) a target-binding moiety;
(ii) at least one amatoxin; and
(iii) optionally a linker L1;
wherein the at least one amatoxin is connected to said target-binding moiety via the γ' C-atom of amino acid 1 of said amatoxin or, if said optional linker is present, the at least one amatoxin is connected to the linker L1 via the γ' C-atom of amino acid 1 of said amatoxin and said linker is connected to said target binding moiety, wherein the target binding moiety is an antibody or antigen-binding fragment thereof, and
wherein the ratio of target-binding moiety to amatoxin is 1 target-binding moiety molecule to 1 amatoxin molecule.

2. The target-binding moiety toxin conjugate of claim 1, wherein the amatoxin is connected to the linker L1 via a nitrogen atom bound to the γ' C-atom of amatoxin acid 1.

3. The target-binding moiety toxin conjugate of claim 1, wherein the amatoxin is connected to the linker L1via an amide linkage.

4. The target-binding moiety toxin conjugate of claim 1, wherein the conjugate has the following structure: amatoxin-γ'C(O)—NH-L1-C(O)—NH-target-binding-moiety.

5. The target-binding moiety toxin conjugate of claim 1, wherein the target-binding moiety is connected to the amatoxin or, if present, to the linker L1 via an amino group present in the target-binding moiety.

6. The target-binding moiety toxin conjugate of claim 1, wherein the amatoxin is selected from α-amanitin, β-amanitin, γ-amanitin, ε-amanitin, amanin, amaninamide, amanullin, or amanullinic acid, or from salts or analogs thereof.

7. The target-binding moiety toxin conjugate of claim 1, wherein the linker L1is an optionally substituted alkyl, heteroalkyl, alkenyl, heteroalkenyl, alkynyl, heteroalkynyl, cycloalkyl, heterocycloalkyl, aryl, heteroaryl, aralkyl, or heteroaralkyl group.

8. The target-binding moiety toxin conjugate of claim 1, wherein the linker L1comprises a disulfide bond.

9. The target-binding moiety toxin conjugate of claim 1, wherein the target-binding moiety specifically binds to an epitope that is present on a tumor cell.

10. The target-binding moiety toxin conjugate of claim 9, wherein the epitope that is present on a tumour cell is a cyclin-dependent kinase, $p15^{Ink4b}$, p53, AFP, B-catenin, caspase 8, Bcr-abl fusion product, MUM-1 MUM-2, MUM-3, ELF2M, HSP70-2M, HST-2, KIAA0205, RAGE, myosin/m, 707-AP, CDC27/m, ETV6/AML, TEL/Amll, LDLR/FUT, Pml-RARa, TEL/AMLI; a Cancer-testis (CT) antigen, a member of the MAGE-family, BAGE, DAM-6, DAM-10, a member of the GAGE- family, NY-ESO-1,CAG-3, RCC-associated antigen G250, human papilloma virus (HPV)-derived E6 and E7oncoproteins, Epstein Barr virus EBNA2-6, LMP-1, LMP-2, gp100, MART-1/Melan-A, tyrosinase-related protein 1 and 2, PSA, PSM, MC1R, ART4, CAMEL, CEA, CypB, epithelial cell adhesion molecule (EpCAM), HER2/neu, HER-3, hTERT, hTRT, ICE, Muc1, Muc2, PRAME, RU1, RU2, SART-1, SART-2, SART-3, or WT1; or a fragment thereof.

11. The target-binding moiety toxin conjugate of claim 1, wherein the antibody or the antigen-binding fragment thereof is selected from a diabody, a tetrabody, a nanobody, a chimeric antibody, a deimmunized antibody, a humanized antibody or a human antibody.

12. The target-binding moiety toxin conjugate of claim 1, wherein the antigen binding fragment is selected from the group consisting of Fab, $F(ab')_2$, Fd, Fv, single-chain Fv, and disulfide-linked Fvs (dsFv).

13. The target-binding moiety toxin conjugate of claim 1, wherein the antibody or the antigen binding fragment thereof comprises:

(a) either the membrane-bound form of the heavy chain of huHEA125 (SEQ ID NO: 1) or the soluble form of the heavy chain of huHEA125 (SEQ ID NO: 2); and/or (b) the light chain of huHEA125 (SEQ ID NO: 11).

14. The target-binding moiety toxin conjugate of claim 1, wherein the target binding moiety is a tumor associated antibody or antigen-binding fragment thereof.

15. The target-binding moiety toxin conjugate of claim 14, wherein the target binding moiety is an antibody or antigen-binding fragment that targets HER2.

16. A method for the treatment of cancer or an autoimmune disease in a patient wherein said method comprises administering, to a patient in need of such treatment, a target-binding moiety toxin conjugate of claim 1.

17. The method, according to claim 16, wherein the cancer is selected from the group consisting of pancreatic cancer, cholangiocarcinoma, breast cancer, colorectal cancer, lung cancer, prostate cancer, ovarian cancer, stomach cancer, kidney cancer, head and neck cancer, a brain tumor, childhood neoplasm, soft tissue sarcoma, epithelial skin cancer, malignant melanoma, leukemia, and malignant lymphoma; and the autoimmune disease is selected from the group consisting of Ankylosing Spondylitis, Chagas disease, Crohns disease, Dermatomyositis, Diabetes mellitus type 1, Goodpasture's syndrome, Graves' disease, Guillain-Barrésyndrome (GBS), Hashimoto's disease, Hidradenitis suppurativa, Idiopathic thrombocytopenic purpura, Lupus erythematosus, Mixed Connective Tissue Disease, Myasthenia gravis, Narcolepsy, Pemphigus vulgaris, Pernicious anaemia, Psoriasis, Psoriatic Arthritis, Polymyositis, Primary biliary cirrhosis, Relapsing polychondritis, Rheumatoid arthritis, Schizophrenia, Sjögren's syndrome, Temporal arteritis, Ulcerative Colitis, and Vasculitis Wegener's granulomatosis.

18. A pharmaceutical composition comprising at least one target-binding moiety toxin conjugate according to claim 1 and further comprising one or more pharmaceutically acceptable diluents, carriers, excipients, fillers, binders, lubricants, glidants, disintegrants, adsorbents, and/or preservatives.

* * * * *

UNITED STATES PATENT AND TRADEMARK OFFICE

CERTIFICATE OF CORRECTION

PATENT NO. : 10,513,559 B2
APPLICATION NO. : 14/954266
DATED : December 24, 2019
INVENTOR(S) : Heinz Faulstich et al.

It is certified that error appears in the above-identified patent and that said Letters Patent is hereby corrected as shown below:

In the Specification

Column 15,
Line 47, "regions of VII;" should read --regions of VH;--.

Column 27,
Line 66, "10000 water." should read --1000μl water.--.

Column 38,
Line 50, "1000 ml" should read --1000μl--.
Line 56, "(14.6 mop" should read --(14.6 μmol)--.

Column 43,
Line 26, "(33.5 mop" should read --(33.5 μmol)--.

Column 44,
Line 47, "(15.9 mmol)" should read --(15.9 μmol)--.
Lines 54-55, "10 mm," should read --10 μm,--.
Line 66, "100 ml" should read --100 μl--.

Column 45,
Line 5, "800 ml" should read --800 μl--.

Signed and Sealed this
Second Day of June, 2020

Andrei Iancu
*Director of the United States Patent and Trademark Office*